(12) United States Patent
Riveiro et al.

(10) Patent No.: US 9,901,583 B2
(45) Date of Patent: Feb. 27, 2018

(54) METHOD OF TREATING NON-SMALL CELL LUNG CANCER AND/OR SMALL CELL LUNG CANCER USING THIENOTRIAZOLODIAZEPINE COMPOUNDS

(71) Applicant: ONCOETHIX GMBH, Lucerne (CH)

(72) Inventors: Maria Eugenia Riveiro, Clichy (FR); Eric Raymond, Noiseau (FR); Francesco Bertoni, Bellinzona (CH)

(73) Assignee: ONCOETHIX GMBH, Lucerne (CH)

( * ) Notice: Subject to any disclaimer, the term of this patent is extended or adjusted under 35 U.S.C. 154(b) by 0 days.

(21) Appl. No.: 15/318,484

(22) PCT Filed: Jun. 12, 2015

(86) PCT No.: PCT/IB2015/054457
§ 371 (c)(1),
(2) Date: Dec. 13, 2016

(87) PCT Pub. No.: WO2015/189814
PCT Pub. Date: Dec. 17, 2015

(65) Prior Publication Data
US 2017/0151255 A1    Jun. 1, 2017

Related U.S. Application Data

(60) Provisional application No. 62/012,042, filed on Jun. 13, 2014, provisional application No. 62/012,051, filed on Jun. 13, 2014, provisional application No. 62/080,760, filed on Nov. 17, 2014, provisional application No. 62/080,779, filed on Nov. 17, 2014, provisional application No. 62/086,466, filed on Dec. 2, 2014.

(51) Int. Cl.
| | |
|---|---|
| A61K 45/06 | (2006.01) |
| A61K 47/02 | (2006.01) |
| A61K 31/551 | (2006.01) |
| A61K 47/32 | (2006.01) |
| A61K 9/10 | (2006.01) |
| A61K 47/38 | (2006.01) |
| A61K 9/14 | (2006.01) |
| A61K 9/16 | (2006.01) |
| A61K 9/48 | (2006.01) |
| A61K 31/436 | (2006.01) |
| A61K 31/4545 | (2006.01) |
| A61K 9/00 | (2006.01) |
| A61K 9/08 | (2006.01) |

(52) U.S. Cl.
CPC ......... *A61K 31/551* (2013.01); *A61K 9/0019* (2013.01); *A61K 9/0053* (2013.01); *A61K 9/08* (2013.01); *A61K 9/10* (2013.01); *A61K 9/146* (2013.01); *A61K 9/1652* (2013.01); *A61K 9/48* (2013.01); *A61K 9/4858* (2013.01); *A61K 9/4866* (2013.01); *A61K 31/436* (2013.01); *A61K 31/4545* (2013.01); *A61K 45/06* (2013.01); *A61K 47/02* (2013.01); *A61K 47/32* (2013.01); *A61K 47/38* (2013.01)

(58) Field of Classification Search
CPC .................................................. A61K 31/551
See application file for complete search history.

(56) References Cited

FOREIGN PATENT DOCUMENTS

| | | |
|---|---|---|
| EP | 1297836 A1 | 4/2003 |
| EP | 2239264 A1 | 10/2010 |
| WO | 2011143669 A2 | 11/2011 |
| WO | 2011146945 A2 | 11/2011 |
| WO | 2012075456 A1 | 6/2012 |
| WO | 2013030150 A1 | 3/2013 |
| WO | 2013071056 A2 | 5/2013 |
| WO | 2620140 A1 | 7/2013 |
| WO | 2014001356 A1 | 1/2014 |
| WO | 2014068402 A2 | 5/2014 |
| WO | 2015078928 A1 | 6/2015 |

OTHER PUBLICATIONS

Song Dong et al., Everolimus synergizes with gefitinib in non-small-cell lung cancer cell lines resistant to epidermal growth factor receptor tyrosine kinase growth factor receptor tyrosine kinase inhibitors, Cancer Chemo Therapy and Pharmacology, Sep. 2, 2012, pp. 707-716, vol. 70., No. 5.

Taofeek Kunle Owonikoko, Window of opportunity preoperative interrogation of mTOR pathway in patients with resectable non-small cell lung cancer (NSCLC), 104th Annual meeting American Cancer Association for Cancer Research (AACR), Apr. 9, 2013, ABST LB-194 XP055164194, (Abstract).

Yuko Iwase et al., Preparation and in Vivo Evaluation of Liposomal Everolimus for Lung Carcinoma and Thyroid Carcinoma, Biological & Pharmaceutical Bulletin, Jan. 1, 2012, pp. 975-979, vol. 35, No. 6.

*Primary Examiner* — Shawquia Jackson
(74) *Attorney, Agent, or Firm* — Catherine D. Fitch; Richard S. Parr

(57) ABSTRACT

A method of treating non-small cell lung cancer and/or small cell lung cancer in a mammal comprises the step of administering to a patient a pharmaceutical acceptable amount of a compound being a thienotriazolodiazepine compound of the Formula (1).

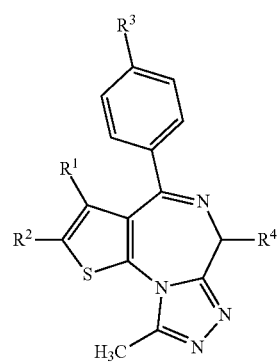

(1)

4 Claims, 38 Drawing Sheets

| Cell line | OTX015 | | Characterization of the mutational status of key proteins in NSCLC cell lines | | | | | |
|---|---|---|---|---|---|---|---|---|
| | GI$_{50}$ [µM] (95%IC) 72h | Emax (at 6 µM) | EML4-ALK fusion protein | KRAS Exon2 | LKB1 (*) | TP53 (*) | RB1 (*) | MYC Status (*) |
| HOP62 | 0.11 (0.08-0.17) | 54 | Negative | Heterozygous mutation c.34G>T | WT | Homozygous mutation c673-2A>G | WT | No MYC Amplification |
| HOP92 | 0.10 (0.06-0.46) | 58 | Negative | WT | WT | Homozygous Substitution Missense C126G>T | WT | MYC Amplification |
| H2228 | 0.63 (0.42-0.95) | 35 | Positive Variant 3 | WT | WT | Homozygous mutation 991C>T | Heterozygous deletion frameshift c510delG | NE |
| H3122 | 0.70 (0.52-0.93) | 41 | Positive Variant 1 | NE | NE | NE | NE | NE |
| A549 | >6 | 82 | Negative | Heterozygous mutation c.34G>A | Mutation Substitution nonsense c109 C>T | WT | WT | No MYC Amplification |

(*) http://www.sanger.ac.uk/perl/genetics/CGP/cosmic. NE = not evaluated

FIG. 13

| Cell line | CT#015 | | Characterisation of the mutational status of key proteins in SCLC cell lines | | | | |
|---|---|---|---|---|---|---|---|
| | GI50 [μM] 72h | Emax (at 6μM) | BRAF Exon2 | PIK3CA Exon20 | TP53 | RB1 | MYC Status |
| NCI-H69 | >6 | 77 | WT | Deletion in frame c.317_325del9 Substitution Missense c.1136G>T | Homozygous mutation Substitution Missense c.818G>T | Homozygous mutation Substitution Nonsense c.22C>G>T | N-MYC Amplification |
| NCI-H82 | >6 | 92 | WT | WT | Homozygous mutation c.375G>T | Homozygous mutation Substitution Missense c.646-3A>T | C-MYC Amplification |
| DMS79 | >6 | 84 | WT | WT | Homozygous mutation c.834_835TG>A | Homozygous mutation 891istopat504 | C-MYC and N-MYC Amplifications |
| DMS114 | 0.12 (0.08-0.2) | 50 | WT | WT | Homozygous mutation c.637C>T | WT | MYC Amplification |

FIG. 19

NE=not evaluated.

METHOD OF TREATING NON-SMALL CELL LUNG CANCER AND/OR SMALL CELL LUNG CANCER USING THIENOTRIAZOLODIAZEPINE COMPOUNDS

This application is a National Stage application of PCT/IB2015/054457, filed Jun. 12, 2015, which claims the benefit of U.S. Provisional Application Ser. No. 62/012,042, filed Jun. 13, 2014, 62/012,051, filed Jun. 13, 2014, 62/080,760, filed Nov. 17, 2014, 62/080,779, filed Nov. 17, 2014 and 62/086,466, filed on Dec. 2, 2014, all of which is incorporated herein by reference in its entirety.

FIELD OF INVENTION

The present disclosure describes methods of treating small cell lung cancer using thienotriazolodiazepine compounds which have improved solubility and bioavailability and may be provided in the form of solid dispersions.

BACKGROUND OF THE INVENTION

Standard chemotherapy for advanced small cell lung cancer ("SCLC") has not changed substantially in the last two decades. The challenge when identifying novel SCLC therapies is the prevalence of inactivating mutations in tumor suppressor genes (TP53, PTEN, RB1), and only infrequent gain-offunction mutations in oncogenes such as PIK3CA or MYC family members. Inhibitors of bromodomain and extraterminal (BET)-bromodomain (BRD) proteins can modulate the transcription of oncogenes, such as the MYC family, via inhibition ofBRD binding to acetylated lysines on histone proteins, preventing the assembly of transcriptional coregulators on target gene promoters.

The compound of Formula (1), described herein below, has been shown to inhibit the binding of acetylated histone H4 to the tandem bromodomain (BRD)-containing family of transcriptional regulators known as the BET (bromodomains and extraterminal) proteins, which include BRD2, BRD3, and BRD4. See U.S. Patent Application Publication No. 2010/0286127 A1, which is incorporated herein by reference in its entirety. The BET proteins have emerged as major epigenetic regulators of proliferation and differentiation and also have been associated with predisposition to dyslipidemia or improper regulation of adipogenesis, elevated inflammatory profile and risk for cardiovascular disease and type 2 diabetes, and increased susceptibility to autoimmune diseases such as rheumatoid arthritis and systemic lupus erythematosus as reported by Denis, G. V. "Bromodomain coactivators in cancer, obesity, type 2 diabetes, and inflammation," *Discov Med* 2010; 10:489-499, which is incorporated herein by reference in its entirety. Accordingly, the compound of formula (1) may be useful for treatment of various cancers, cardiovascular disease, type 2 diabetes, and autoimmune disorders such as rheumatoid arthritis and systemic lupus erythematosus.

BRIEF SUMMARY OF THE INVENTION

In some embodiments, the present disclosure provides for methods of treating small cell lung cancer using the compositions described herein. In some embodiments, the present disclosure provides for methods of treating non-small cell lung cancer using the compositions described herein.

In some embodiments, the present disclosure provides for methods of treating non-small cell lung cancer and/or small cell lung cancer in a mammal comprising: administering to a patient in need a pharmaceutically acceptable amount of a composition comprising any of the compositions described in Sections III, IV, V and VI described herein.

In some embodiments, the present disclosure provides for methods of treating non-small cell lung cancer and/or small cell lung cancer in a mammal comprising: administering to a patient in need a pharmaceutically acceptable amount of a composition comprising a solid dispersion according to any of the compositions described in Sections III, IV, V and VI described herein.

In some embodiments, the present disclosure provides for a compound of Formula (1), in particular of Formula (1A) for use in treating non-small cell lung cancer and/or small cell lung cancer.

In some embodiments, the present disclosure provides for a a solid dispersion according to any of the compositions described in Sections III, IV, V and VI described herein for use in treating non-small cell lung cancer and/or small cell lung cancer.

In some embodiments, the present disclosure provides for methods of treating non-small cell lung cancer and/or small cell lung cancer using thienotriazolodiazepine compound of the Formula (1)

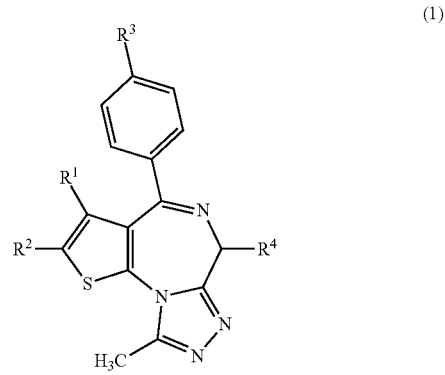

wherein
$R^1$ is alkyl having a carbon number of 1-4,
$R^2$ is a hydrogen atom; a halogen atom; or alkyl having a carbon number of 1-4 optionally substituted by a halogen atom or a hydroxyl group,
$R^3$ is a halogen atom; phenyl optionally substituted by a halogen atom, alkyl having a carbon number of 1-4, alkoxy having a carbon number of 1-4 or cyano; —$NR^5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—CO—$(CH_2)_n$—$R^8$ wherein $R^7$ is a hydrogen atom or alkyl having a carbon number of 1-4, n is an integer of 0-2, and $R^8$ is phenyl or pyridyl optionally substituted by a halogen atom, and
$R^4$ is —$(CH_2)_a$—CO—NH—$R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4, or a pharmaceutically acceptable salt thereof or a hydrate or solvate thereof.

In some embodiments, Formula (1) is selected from Formula (1A):

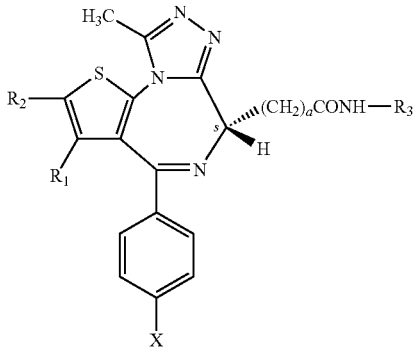

wherein X is a halogen, $R^1$ is $C_1$-$C_4$ alkyl, $R^2$ is $C_1$-$C_4$ alkyl, a is an integer of 1-4, $R^3$ is $C_1$-$C_4$ alkyl, $C_1$-$C_4$ hydroxyalkyl, $C_1$-$C_4$ alkoxy, phenyl optionally having substituent(s) as defined for $R^9$ in Formula (1), or heteroaryl optionally having substituent(s) as defined for $R^9$ in Formula (1), a pharmaceutically acceptable salt thereof or a hydrate thereof.

In one such embodiment, the thienotriazolodiazepine compound is formulated as a solid dispersion comprising an amorphous thienotriazolodiazepine compound and a pharmaceutically acceptable polymer.

In one embodiment, Formula (1) is selected from the group consisting of: (i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof; (ii) methyl (S)-{4-(3'-cyanobiphenyl-4-yl)-2,3,9-trimethyl-6H-thieno[3,2-f][1,2,4]triazolo[4,3-a][1,4]diazepin-6-yl}acetate, (iii) methyl (S)-{2,3,9-trimethyl-4-(4-phenylaminophenyl)-6H-thieno[3,2-f][1,2,4]triazolo[4,3-a][1,4]diazepin-6-yl}acetate; and (iv) methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate.

In one embodiment, the thienotriazolodiazepine compound represented by Formula (1) is (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide dihydrate.

In one embodiment, the thienotriazolodiazepine compound represented by Formula (1) is (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide.

In some embodiments the present disclosure provides for methods of treating non-small cell lung cancer and/or small cell lung cancer using thienotriazolodiazepine compound of the Formula (1) in combination with one or more chemotherapy drugs selected from the group consisting of m-TOR inhibitors and ALK inhibitors.

In some embodiments the present disclosure provides for methods of treating non-small cell lung cancer and/or small cell lung cancer using thienotriazolodiazepine compound of the Formula (1A) in combination with one or more chemotherapy drugs selected from the group consisting of m-TOR inhibitors and ALK inhibitors.

In some embodiments the method further comprises administering to the patient an mTOR inhibitor. In one such embodiment the mTOR inhibitor is selected from the group consisting of rapamycin, temsirolimus, ridaforolimus and everolimus. In one such embodiment the mTOR inhibitor is everolimus. The thienotriazolodiazepine compound and the mTOR inhibitor can be administered simultaneously or sequentially. In some embodiments such combination of thienotriazolodiazepine compound and mTOR inhibitor produces a synergistic effect.

In some embodiments the method further comprises administering to the patient an ALK inhibitor. In one such embodiment the ALK inhibitor is selected from the group consisting of ceritinib and crizotinib. In one such embodiment the ALK inhibitor is crizotinib. The thienotriazolodiazepine compound and the ALK inhibitor can be administered simultaneously or sequentially. In some embodiments such combination of thienotrizolodiazepine compound and ALK inhibitor produces a synergistic effect.

In one embodiment, the non-small cell lung cancer is EML4-ALk positive. In one such embodiment, the non-small cell lung cancer exhibited down regulation of N-MYC mRNA levels after treatment. In another such embodiment, the non-small cell lung cancer expressed BRD4/3/2, c-MYC, BCL-2, p21 and Cyclin D1. In still another embodiment, the treatment induced a transient upregulation of STAT3 with a subsequent down-regulation after 24 hour and up to 72 hour exposure.

In still another embodiment, the non-small cell lung cancer is EML4-ALk negative. In one such embodiment, the non-small cell lung cancer expressed BRD4/3/2, c-MYC, BCL-2, p21 and Cyclin D1. In another such embodiment, the treatment induced a transient up-regulation of STAT3 with a subsequent down-regulation after 24 hour and up to 72 hour exposure.

In one embodiment NMYC is downregulated. In one embodiment HEXIM is upregulated.

in some embodiments of a method of treating non-small cell lung cancer and/or small cell lung cancer, the EFR3B gene is upregulated. In some embodiments of a method of treating non-small cell lung cancer and/or small cell lung cancer, the FOS gene is upregulated. In some embodiments of a method of treating non-small cell lung cancer and/or small cell lung cancer, the IL7R gene is downregulated. In some embodiments of a method of treating non-small cell lung cancer and/or small cell lung cancer, the IL6-related gene is down regulated. In some embodiments, EFR3B and FOS genes are upregulated and IL7R and IL6-related genes are downregulated.

In one embodiment, the thienotriazolodiazepine compound of the Formula (1) is formed as a solid dispersion. In one embodiment, the solid dispersion comprises an amorphous thienotriazolodiazepine compound of Formula (1) or a pharmaceutically acceptable salt thereof or a hydrate thereof; and a pharmaceutically acceptable polymer. In one embodiment, the solid dispersion exhibits an X-ray powder diffraction pattern substantially free of diffraction lines associated with crystalline thienotriazolodiazepine compound of Formula (1). In one embodiment, the pharmaceutically acceptable polymer is hydroxypropylmethylcellulose acetate succinate having a thienotriazolodiazepine compound to hydroxypropylmethylcellulose acetate succinate (HPMCAS) weight ratio of 1:3 to 1:1. In one embodiment, the solid dispersion exhibits a single glass transition temperature (Tg) inflection point ranging from about 130° C. to about 140° C.

In one embodiment, a solid dispersion comprises an amorphous thienotriazolodiazepine compound of (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide dihydrate or a pharmaceutically acceptable salt thereof or a hydrate thereof; and a pharmaceutically acceptable polymer. In one embodiment, the solid dispersion exhibits an X-ray powder diffraction pattern substantially free of diffraction lines associated with crystalline thienotriazolodiazepine compound of (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide dihydrate. In one embodiment, the pharmaceutically acceptable polymer is hydroxypropylmethylcellulose acetate succinate having a thienotriazolodiazepine compound to hydroxypropylmethylcellulose acetate succinate (HPMCAS) weight ratio of 1:3 to 1:1. In one embodiment, the solid dispersion exhibits a single glass transition temperature (Tg) inflection point ranging from about 130° C. to about 140° C.

It should be understood that any embodiment of the compounds according to Formula (1) described herein may be used in any embodiment of a pharmaceutical composition described herein, unless indicated otherwise. Moreover, any compound or pharmaceutical composition described herein as embodiment of the invention may be used as a medicament, in particular for treating non-small cell lung cancer and/or small cell lung cancer as described in embodiments herein, unless indicated otherwise.

BRIEF DESCRIPTION OF THE DRAWINGS

The foregoing summary, as well as the following detailed description of embodiments of the pharmaceutical compositions including thienotriazolodiazepine formulations and methods of the present invention, will be better understood when read in conjunction with the appended drawings of exemplary embodiments. It should be understood, however, that the invention is not limited to the precise arrangements and instrumentalities shown.

In the drawings:

FIG. 13 illustrates the compound (1-1) antiproliferative effects after 72 h and characterization of common mutations found in NSCLC cells;

FIG. 19 illustrates compound (1-1) (OTX015) antiproliferative effects after 72 hours in NCI-H69, NCI-H82, DMS79 and DMS114 cell lines and characterization of common mutations found in such cell lines;

DETAILED DESCRIPTION OF THE INVENTION

Figure 1A:
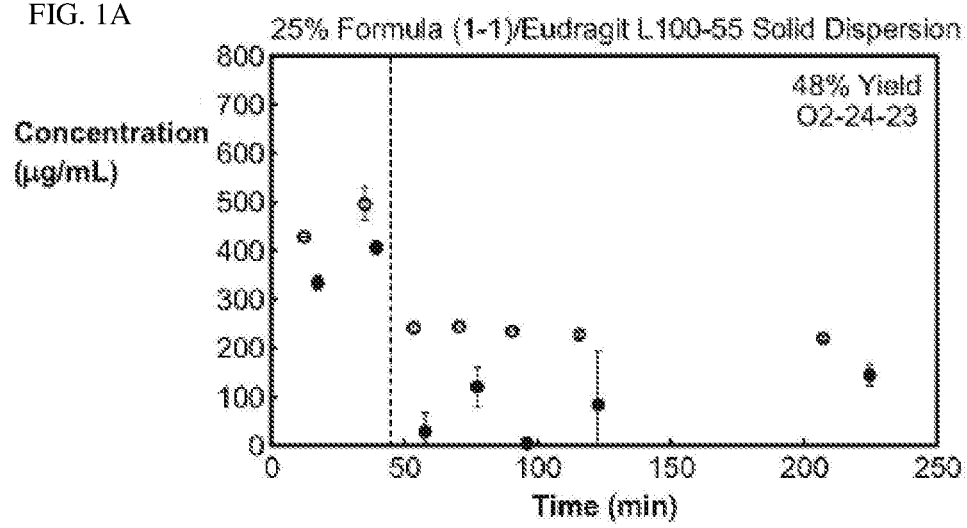
FIG. 1A illustrates dissolution profile of a comparator formulation comprising a solid dispersion comprising 25% compound (1-1) and Eudragit L100-55.
Figure 1B:
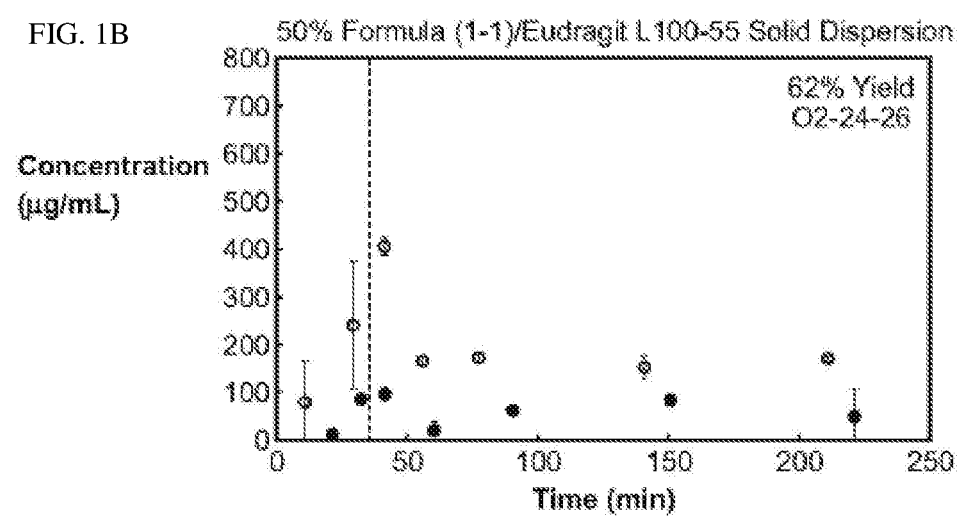
FIG. 1B illustrates dissolution profile of a comparator formulation comprising a solid dispersion comprising 50% compound (1-1) and Eudragit L100-55.
Figure 1C:
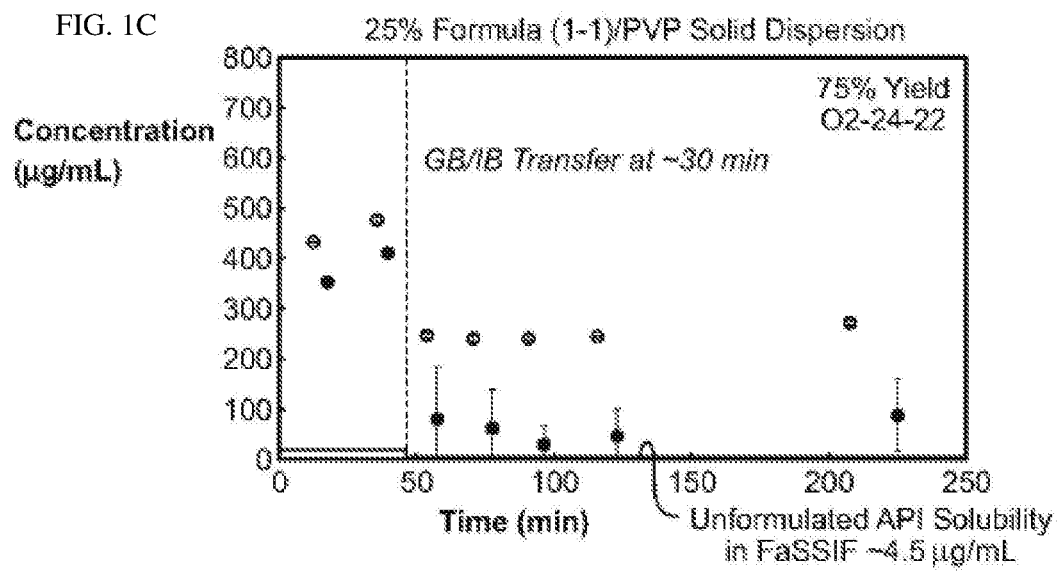
FIG. 1C illustrates dissolution profile of an exemplary formulation comprising a solid dispersion comprising 25% compound (1-1) and polyvinylpyrrolidone (PVP)
Figure 1D:
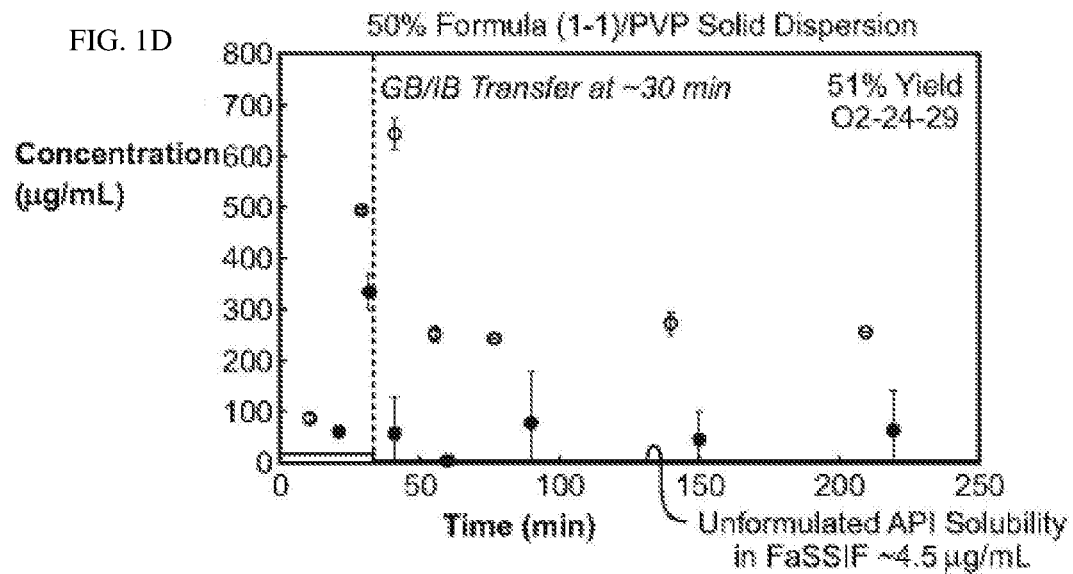
FIG. 1D illustrates dissolution profile of an exemplary formulation comprising a solid dispersion comprising 50% compound (1-1) and PVP.
Figure 1E:
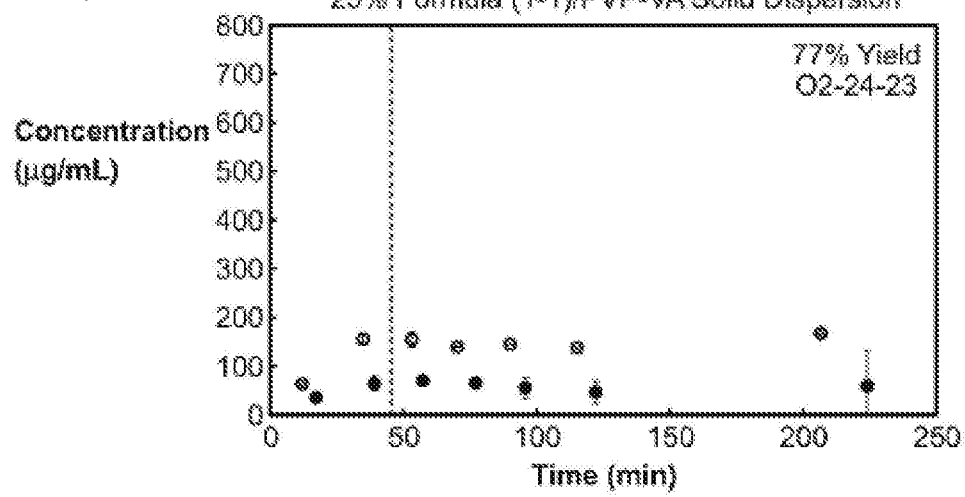
FIG. 1E illustrates dissolution profile of an exemplary formulation comprising a solid dispersion comprising 25% compound (1-1) and PVP-vinyl acetate (PVP-VA)
Figure 1F:
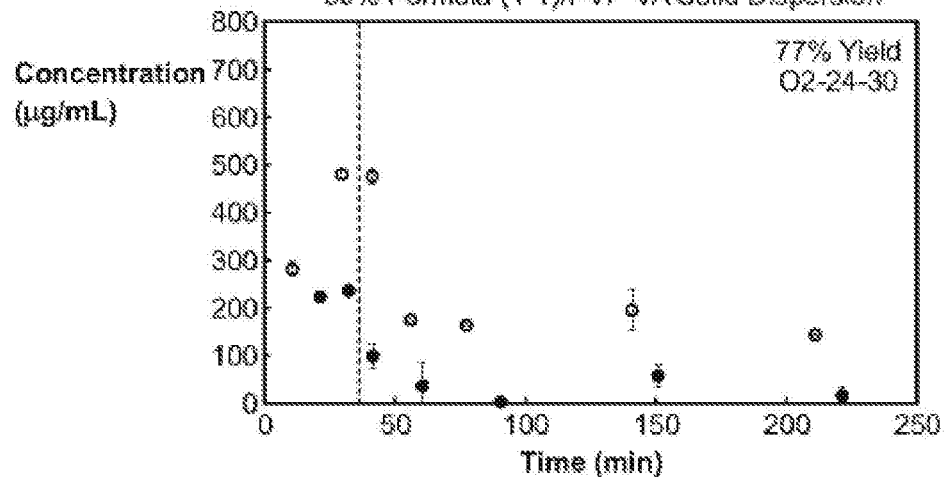
FIG. 1F illustrates dissolution profile of an exemplary formulation comprising a solid dispersion comprising 50% compound (1-1) and PVP-VA.
Figure 1G:
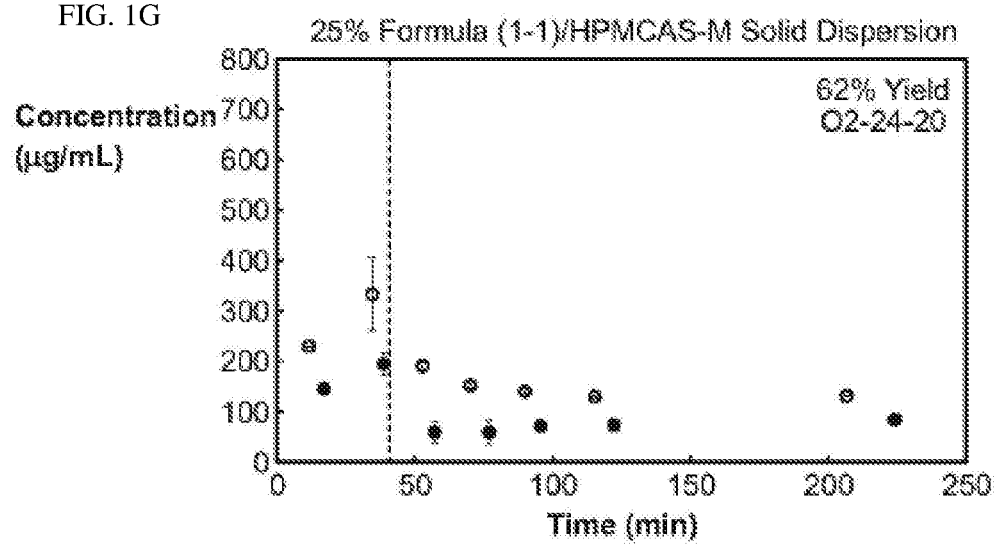
FIG. 1G illustrates dissolution profile of an exemplary formulation comprising a solid dispersion comprising 25% compound (1-1) and hypromellose acetate succinate (HPMCAS-M)
Figure 1H:
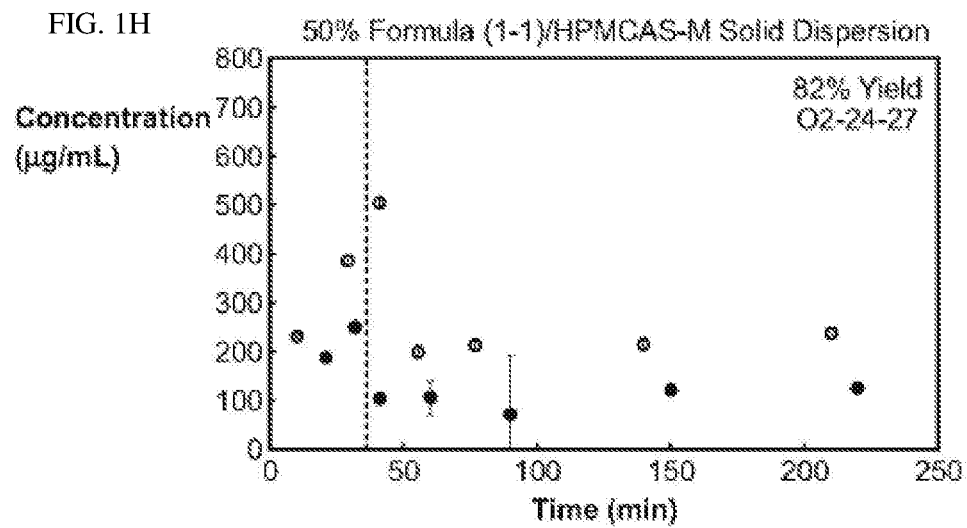
FIG. 1H illustrates dissolution profile of an exemplary formulation comprising a solid dispersion comprising 50% compound (1-1) and HPMCAS-M.
Figure 1I:
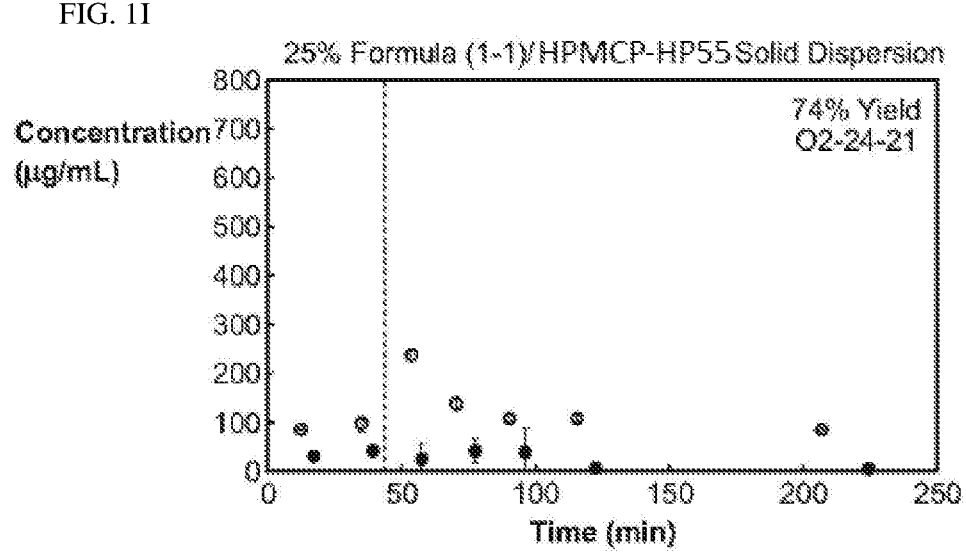
FIG. 1I illustrates dissolution profile of an exemplary formulation comprising a solid dispersion comprising 25% compound (1-1) and hypromellose phthalate (HPMCP-HP55)
Figure 1J:
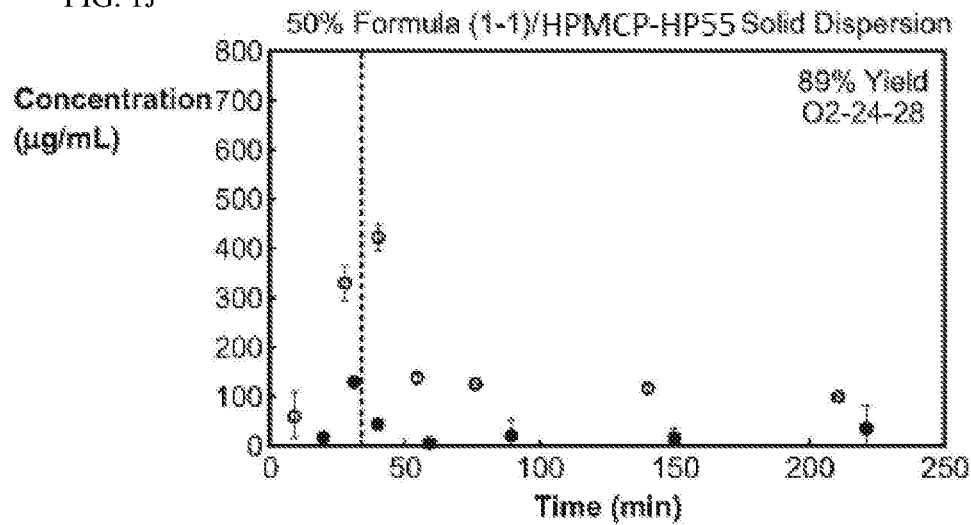
FIG. 1J illustrates dissolution profile of an exemplary formulation comprising a solid dispersion comprising 50% compound (1-1) and HPMCP-HP55.

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entireties.

I. Definitions:

The term "alkyl group" as used herein refers to a saturated straight or branched hydrocarbon.

The term "substituted alkyl group" refers to an alkyl moiety having one or more substituents replacing a hydrogen or one or more carbons of the hydrocarbon backbone.

The term "alkenyl group" whether used alone or as part of a substituent group, for example, "$C_{1-4}$alkenyl(aryl)," refers to a partially unsaturated branched or straight chain monovalent hydrocarbon radical having at least one carbon—carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl(2-propenyl), butenyl and the like. Examples include $C_{2-8}$alkenyl or $C_{2-4}$alkenyl groups.

The term "$C_{(j-k)}$" (where j and k are integers referring to a designated number of carbon atoms) refers to an alkyl, alkenyl, alkynyl, alkoxy or cycloalkyl radical or to the alkyl portion of a radical in which alkyl appears as the prefix root containing from j to k carbon atoms inclusive. For example, $C_{(1-4)}$ denotes a radical containing 1, 2, 3 or 4 carbon atoms.

The terms "halo" or "halogen" as used herein refer to F, Cl, Br, or I.

The term "pharmaceutically acceptable salts" is art-recognized and refers to the relatively non-toxic, inorganic and organic acid addition salts, or inorganic or organic base addition salts of compounds, including, for example, those contained in compositions of the present invention.

The term "solid dispersion" as used herein refers to a group of solid products consisting of at least two different components, generally a hydrophilic carrier and a hydrophobic drug (active ingredient).

The term "chiral" is art-recognized and refers to molecules That have the property of non-superimposability of the mirror image partner, while the term "achiral" refers to molecules which are superimposable on their mirror image partner. A "prochiral molecule" is a molecule that has the potential to be converted to a chiral molecule in a particular process.

The symbol "=====" is used to denote a bond that may be a single, a double or a triple bond.

The term "enantiomer" as it used herein, and structural formulas depicting an enantiomer are meant to include the "pure" enantiomer free from its optical isomer as well as mixtures of the enantiomer and its optical isomer in which the enantiomer is present in an enantiomeric excess, e.g., at least 10%, 25%, 50%, 75%, 90%, 95%, 98%, or 99% enantiomeric excess.

The term "stereoisomers" when used herein consist of all geometric isomers, enantiomers or diastereomers. The present invention encompasses various stereoisomers of these compounds and mixtures thereof. Conformational isomers and rotamers of disclosed compounds are also contemplated.

The term "stereoselective synthesis" as it is used herein denotes a chemical or enzymatic reaction in which a single reactant forms an unequal mixture of stereoisomers during the creation of a new stereocenter or during the transformation of a pre-existing one, and are well known in the art. Stereoselective syntheses encompass both enantioselective and diastereoselective transformations. For examples, see Carreira, E. M. and Kvaerno, L., *Classics in Stereoselective Synthesis*, Wiley-VCH: Weinheim, 2009.

The term "spray drying" refers to processes which involve the atomization of the feed suspension or solution into small droplets and rapidly removing solvent from the mixture in a processor chamber where there is a strong driving force for the evaporation (e.g., hot dry gas or partial vacuum or combinations thereof).

The term "therapeutically effective amount" as used herein refers to any amount of a thienotriazolodiazepine of the present invention or any other pharmaceutically active agent which, as compared to a corresponding patient who has not received such an amount of the thienotriazolodiazepine or the other pharmaceutically active agent, results in improved treatment, healing, prevention, or amelioration of a disease, disorder, or side effect, or a decrease in the rate of advancement of a disease or disorder.

The term "about" means+/−10%. In one embodiment, it means+/−5%.

Throughout this application and in the claims that follow, unless the context requires otherwise, the word "comprise", or variations such as "comprises" or "comprising", should be understood to imply the inclusion of a stated integer step or group of integers or steps but not the exclusion of any other integer or step or group of integers or steps. Moreover, the word "comprise" should be understood to imply "consist of".

It has now been found that thienotriazolodiazepine compound of Formula (1), described herein below, can be formulated as a solid dispersion with a pharmaceutically acceptable polymers, to provide an oral formulation that provides high absorption of the pharmaceutical ingredient into the circulation from the gastrointestinal tract. In one embodiment, the pharmaceutically acceptable polymer is hypromellose acetate succinate (also called hydroxypropylmethylcellulose acetate succinate or HPMCAS). In one embodiment, the pharmaceutically acceptable polymer is polyvinylpyrrolidone (PVP).

In some embodiments, the hydroxypropylmethyl cellulose acetate succinates (HPMCAS), may include M grade having 9% acetyl/11% succinoyl (e.g., HPMCAS having a mean particle size of 5 μm (i.e., HPMCAS-MF, fine powder grade) or having a mean particle size of 1 mm (i.e., HPMCAS-MG, granular grade)), H grade having 12% acetyl/6% succinoyl (e.g., HPMCAS having a mean particle size of 5 μm (i.e., HPMCAS-HF, fine powder grade) or having a mean particle size of 1 mm (i.e., HPMCAS-HG, granular grade)), and L grade having 8% acetyl/15% succinoyl (e.g., HPMCAS having a mean particle size of 5 μm (i.e., HPMCAS-LF, fine powder grade) or having a mean particle size of 1 mm (i.e., HPMCAS-LG, granular grade).

In some embodiments, the polyvinyl pyrrolidones may have molecular weights of about 2,500 (KOLLIDON®12 PF, weight-average molecular weight between 2,000 to 3,000), about 9,000 (KOLLIDON® 17 PF, weight-average molecular weight between 7,000 to 11,000), about 25,000 (KOLLIDON® 25, weight-average molecular weight between 28,000 to 34,000), about 50,000 (KOLLIDON® 30, weight-average molecular weight between 44,000 to 54,000), or about 1,250,000 (KOLLIDON® 90 or KOLLIDON® 90F, weight-average molecular weight between 1,000,000 to 1,500,000).

II. Methods Of Treatment

In some embodiments, the present disclosure provides for methods of treating small cell lung cancer (SCLC) using the compositions described herein. In some embodiments, the present disclosure provides for methods of treating non-small cell lung cancer (NSCLC) using the composition described herein.

In some embodiments the present disclosure provides for methods of treating non-small cell lung cancer and/or small cell lung cancer using the composition described herein. With regard to the method of the invention, the term "and/or" means the method treats a condition in which 1) non-small cell lung cancer and small cell lung cancer are both present in the patient, or 2) either non-small cell lung cancer or small cell lung cancer, but not both, are present in the patient.

In some embodiments, the present disclosure provides for methods of treating non-small cell lung cancer and/or small cell lung cancer in a mammal comprising: administering to a patient in need a pharmaceutically acceptable amount of a composition comprising a solid dispersion according to any of the compositions described in Sections III, IV, V and VI described herein.

In some embodiments, the present disclosure provides for methods of treating non-small cell lung cancer and/or small cell lung cancer in a mammal comprising: administering to a patient in need a pharmaceutically acceptable amount of a composition comprising a pharmaceutical formulation according to any of the compositions described in Sections III, IV, V and VI described herein.

In some embodiments, the present disclosure provides for a compound of Formula (1), in particular of Formula (1A) for use in treating non-small cell lung cancer and/or small cell lung cancer.

In some embodiments, the present disclosure provides for a a solid dispersion according to any of the compositions described in Sections III, IV, V and VI described herein for use in treating non-small cell lung cancer and/or small cell lung cancer.

In some embodiments, methods of treating non-small cell lung cancer and/or small cell lung cancer use thienotriazolodiazepine compound of the Formula (1)

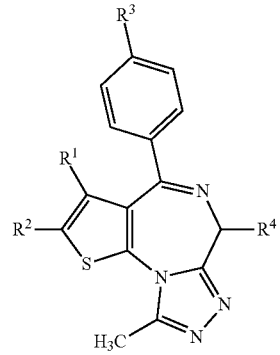

wherein
$R^1$ is alkyl having a carbon number of 1-4,
$R^2$ is a hydrogen atom; a halogen atom; or alkyl having a carbon number of 1-4 optionally substituted by a halogen atom or a hydroxyl group, $R^3$ is a halogen atom; phenyl optionally substituted by a halogen atom, alkyl having a carbon number of 1-4, alkoxy having a carbon number of 1-4 or cyano; —$NR^5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—CO—$(CH_2)_n$—$R^8$ wherein $R^7$ is a hydrogen atom or alkyl having a carbon number of 1-4, n is an integer of 0-2, and $R^8$ is phenyl or pyridyl optionally substituted by a halogen atom, and $R^4$ is —$(CH_2)_a$—CO—NH—$R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4, including any salts, isomers, enantiomers, racemates, hydrates, solvates, metabolites, and polymorphs thereof.

In some embodiments, Formula (1) is selected from Formula (1A):

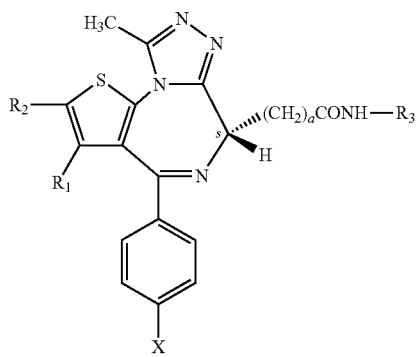

wherein X is a halogen, $R^1$ is $C_1$-$C_4$ alkyl, $R^2$ is $C_1$-$C_4$ alkyl, a is an integer of 1-4, $R^3$ is $C_1$-$C_4$ alkyl, $C_1$-$C_4$ hydroxyalkyl, $C_1$-$C_4$ alkoxy, phenyl optionally having substituent(s) as defined for $R^9$ in Formula (1), or heteroaryl optionally having substituent(s) as defined for $R^9$ in Formula (1), a pharmaceutically acceptable salt thereof or a hydrate thereof.

In one such embodiment, the thienotriazolodiazepine compound is formulated as a solid dispersion comprising an amorphous thienotriazolodiazepine compound and a pharmaceutically acceptable polymer.

In some embodiments the small cell lung cancer is combined small cell carcinoma. Combined small cell carcinoma can refer to small-cell carcinoma plus one or more differentiated forms of lung cancer, such as squamous cell carcinoma or adenocarcinoma. In other embodiments the small cell lung cancer is small cell carcinoma (also referred to as oat cell cancer).

In some embodiments of the methods of the present invention, the small cell lung cancer harbors a homozygous mutation C637C>T. In some embodiments of the methods of the present invention, treatment induces upregulation of HEXIM the small cell lung cancer.

In some embodiment, the non-small cell lung cancer is EML4-ALk positive. In one embodiment, the non-small cell lung cancer exhibits down regulation of N-MYC mRNA levels after treatment. In another embodiment, the non-small cell lung cancer expresses BRD4/3/2, c-MYC, BCL-2, p21, Cyclin D1, or a combination thereof. In still another embodiment, the treatment induces a transient up-regulation of STAT3 with a subsequent down-regulation between about 24 hours and about 72 hours after exposure.

In still another embodiment, the non-small cell lung cancer is EML4-ALk negative. In one embodiment, the non-small cell lung cancer expresses BRD4/3/2, c-MYC, BCL-2, p21, Cyclin D1, or a combination thereof. In another embodiment, the treatment induces a transient up-regulation of STAT3 with a subsequent down-regulation after 24 hour and up to 72 hour exposure.

In some embodiments, the non-small-cell lung cancer has a mutation in the KRAS gene. In some embodiment the non-small-cell lung cancer has a mutation in the LKB1 gene. In some embodiments the non-small-cell lung cancer has a mutation in both the KRAS and LKB1 genes.

In some embodiments, treatment induces downregulation of N-MYC (e.g. in some embodiments the non-small cell lung cancer exhibits down regulation of N-MYC mRNA levels during or after treatment). In some embodiments, treatment induces downregulation of IL7R. In some embodiments, treatment induces downregulation of IL6-related gene. In some embodiments, treatment induces upregulation of HEXIM. In some embodiments, treatment induces upregulation of FOS. In some embodiments, treatment induces upregulation of EFR3B.

In some embodiments the present disclosure provides for methods of treating non-small cell lung cancer and/or small cell lung cancer using thienotriazolodiazepine compound of the Formula (1) in combination with a drug selected from the group consisting of m-TOR inhibitors and ALK inhibitors.

In some embodiments the present disclosure provides for methods of treating non-small cell lung cancer and/or small cell lung cancer using thienotriazolodiazepine compound of the Formula (1A) in combination with a drug selected from the group consisting of m-TOR inhibitors and ALK inhibitors.

In some embodiments the method further comprises administering to the patient an mTOR inhibitor. In one such embodiment the mTOR inhibitor is selected from the group consisting of rapamycin, temsirolimus, ridaforolimus and everolimus. In one such embodiment the mTOR inhibitor is everolimus. The thienotriazolodiazepine compound and the mTOR inhibitor can be administered simultaneously or sequentially. In some embodiments such combination of thienotrizolodiazepine compound and mTOR inhibitor produces a synergistic effect.

Example mammalian target of rapamycin (mTOR) inhibitors for use in combination with the thienotriazolodiazepine of Formula (1) in the methods of the present invention include, but are not limited to, the mTOR inhibitors listed in the below Table A.

TABLE A

Exemplary mTOR inhibitor compounds which may be used in combination with thienotriazolodiazepine of Formula (1):

| No. | Inhibitor Name | Description | Literature Citations |
|---|---|---|---|
| 1 | BEZ235 (NVP-BEZ235) | BEZ235 (NVP-BEZ235) is a dual ATP-competitive PI3K and mTOR inhibitor of p110α, p110γ, p110δ and p110β with IC50 of 4 nM, 5 nM, 7 nM and 75 nM, respectively, and also inhibits ATR with IC50 of 21 nM. | Nature, 2012, 487(7408): 505-9; Blood, 2011, 118(14), 3911-3921; Cancer Res, 2011, 71(15), 5067-5074. |
| 2 | Everolimus (RAD001) | Everolimus (RAD001) is an mTOR inhibitor of FKBP12 with IC50 of 1.6-2.4 nM. | Cell, 2012, 149(3): 656-70;; Cancer Cell, 2012, 21(2), 155-167; Clin Cancer Res, 2013, 19(3): 598-609. |
| 3 | Rapamycin (Sirolimus, AY22989, NSC226080) | Rapamycin (Sirolimus, AY-22989, WY-090217) is a specific mTOR inhibitor with IC50 of ~0.1 nM. | Cancer Cell, 2011, 19(6), 792-804;; Cancer Res, 2013, ; Cell Res, 2012, 22(6): 1003-21. |
| 4 | AZD8055 | AZD8055 is a novel ATP-competitive inhibitor of mTOR with IC50 of 0.8 nM. | Autophagy, 2012, Am J Transplant, 2013, ; Biochem Pharmacol, 2012, 83(9), 1183-1194 |
| 5 | PI-103 <br> 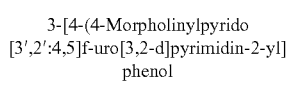 <br> 3-[4-(4-Morpholinylpyrido[3',2':4,5]f-uro[3,2-d]pyrimidin-2-yl] phenol | PI-103 is a potent, ATP-competitive PI3K inhibitor of DNA-PK, p110α, mTORC1, PI3KC2β, p110δ, mTORC2, p110β, and p110γ with IC50 of 2 nM, 8 nM, 20 nM, 26 nM, 48 nM, 83 nM, 88 nM and 150 nM, respectively. | Leukemia, 2013, 27(3): 650-60; Leukemia, 2012, 26(5): 927-33; Biochem Pharmacol, 2012, 83(9), 1183-1194. |
| 6 | Temsirolimus (CCI-779, NSC-683864) | Temsirolimus (CCI-779, Torisel) is a specific mTOR inhibitor with IC50 of 1.76 μM. | Autophagy, 2011, 7(2), 176-187; Tuberc Respir Dis (Seoul), 2012, 72(4), 343-351; PLoS One, 2013, 8(5): e62104. |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 7 | Ku-0063794 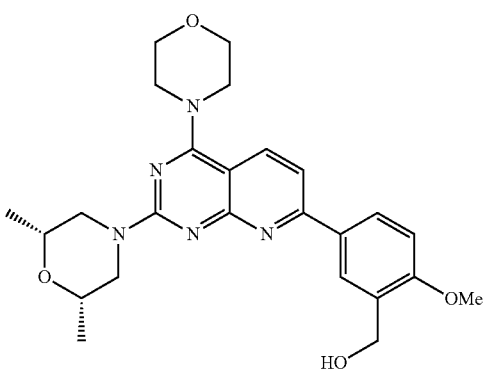<br>rel-5-[2-[(2R,6S)-2,6-dimethyl-4-mo-rpholinyl]-4-(4-morpholinyl)pyrido[2,3-d]pyrimidin--7-yl]-2-methoxybenzenemethanol | KU-0063794 is a potent and highly specific mTOR inhibitor for both mTORC1 and mTORC2 with IC50 ~10 nM. | Cell Stem Cell, 2012, 10(2): 210-7; Circ Res, 2010, 107(10), 1265-1274; J Immunol, 2013, 190(7), 3246-55. |
| 8 | GDC-0349 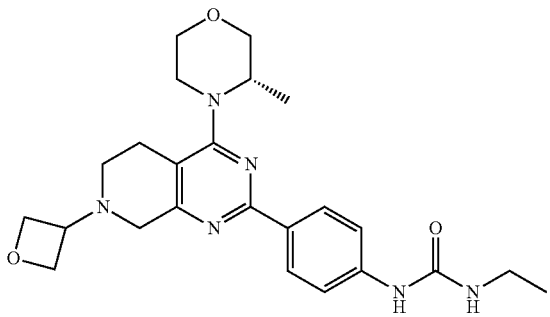 | GDC-0349, is a potent and selective ATP-competitive inhibitor of mTOR with Ki of 3.8 nM. | |
| 9 | Torin 2 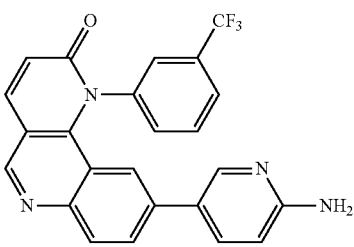<br>9-(6-Amino-3-pyridinyl)-1-[3-(trifl-uoromethyl)phenyl]-benzo[h]-1,6-naphthyridin-2(1H)--one | Torin 2 is a highly potent and selective mTOR inhibitor with IC50 of 0.25 nM, and also exhibits potent cellular activity against ATM/ATR/DNA-PK with EC50 of 28 nM, 35 nM and 118 nM, respectively. | |

TABLE A-continued

Exemplary mTOR inhibitor compounds which may be used in combination with thienotriazolodiazepine of Formula (1):

| No. | Inhibitor Name | | Description | Literature Citations |
|---|---|---|---|---|
| 10 | INK 128 (MLN-0128) 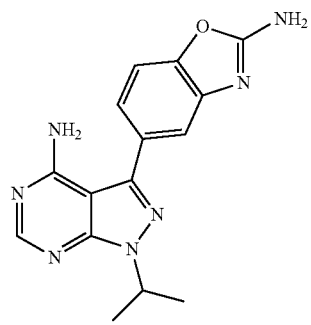 | | INK 128 is a potent and selective mTOR inhibitor with IC50 of 1 nM. | |
| 11 | AZD2014 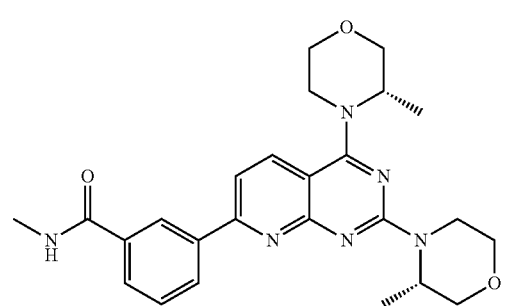 | | AZD2014 is a novel dual mTORC1 and mTORC2 inhibitor with potential antineoplastic activity. | |
| 12 | NVP-BGT226(BGT226) 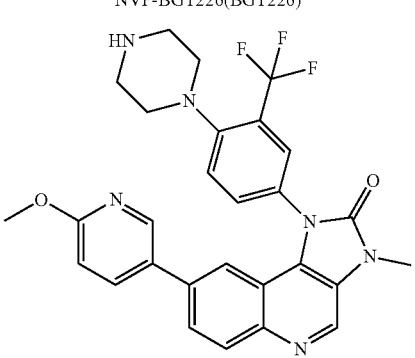 | | NVP-BGT226 is a novel dual PI3K/mTOR inhibitor with IC50 of 1 nM. | |
| 13 | PF-04691502 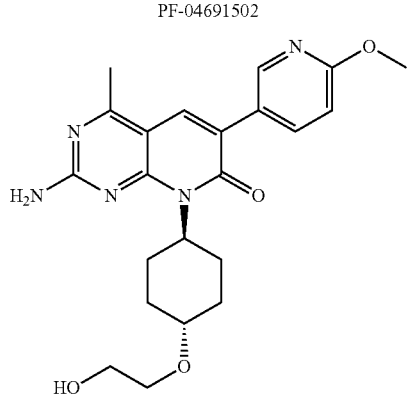 [SMILES: COc1ccc(-c2cc3c(C)nc(N)nc3n([C@H]3CC[C@H](OCCO)CC3)c2=O)cn1] | | PF-04691502 is an ATP-competitive, selective inhibitor of PI3K($\alpha/\beta/\delta/\gamma$)/mTOR with Ki of 1.8 nM/2.1 nM/ 1.6 nM/1.9 nM and 16 nM, also inhibits Akt phosphorylation on T308/S473 with IC50 of 7.5 nM/3.8 nM. | |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 14 | CH5132799 | CH5132799 exhibits a strong inhibitory activity especially against PI3Kα with IC50 of 14 nM and also inhibits mTOR with IC50 of 1.6 μM. | |
| 15 | GDC-0980 (RG7422) | GDC-0980 (RG7422) is a potent, selective inhibitor of PI3Kα, PI3Kβ, PI3Kδ and PI3Kγ with IC50 of 5 nM, 27 nM, 7 nM, and 14 nM, and also a mTOR inhibitor with Ki of 17 nM. | |
| 16 | Torin 1<br>1-[4-[4-(1-Oxopropyl)-1-piperazinyl-]-3-(trifluoromethyl)phenyl]-9-(3-quinolinyl)-benz-o[h]-1,6-naphthyridin-2(1H)-one | Torin1 is a potent inhibitor of mTOR with IC50 of 2-10 nM. | |

TABLE A-continued

Exemplary mTOR inhibitor compounds which may be used in combination with
thienotriazolodiazepine of Formula (1):

| No. | Inhibitor Name | Description | Literature Citations |
|---|---|---|---|
| 17 | WAY-600 | WAY-600 is a potent, ATP-competitive and selective inhibitor of mTOR with IC50 of 9 nM. | |
| 18 | WYE-125132(WYE-132) | WYE-125132 is a highly potent, ATP-competitive and specific mTOR inhibitor with IC50 of 0.19 nM. | |
| 19 | WYE-687 | WYE-687 is an ATP-competitive and selective inhibitor of mTOR with IC50 of 7 nM. | |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 20 | GSK2126458(GSK458) 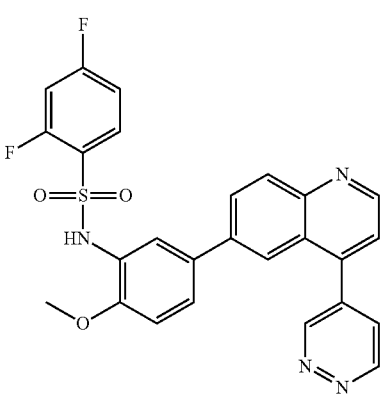 | GSK2126458 is a highly selective and potent inhibitor of p110α, p110β, p110γ, p110δ, mTORC1 and mTORC2 with Ki of 0.019 nM, 0.13 nM, 0.024 nM, 0.06 nM, 0.18 nM and 0.3 nM, respectively. | |
| 21 | PF-05212384 (PKI-587) 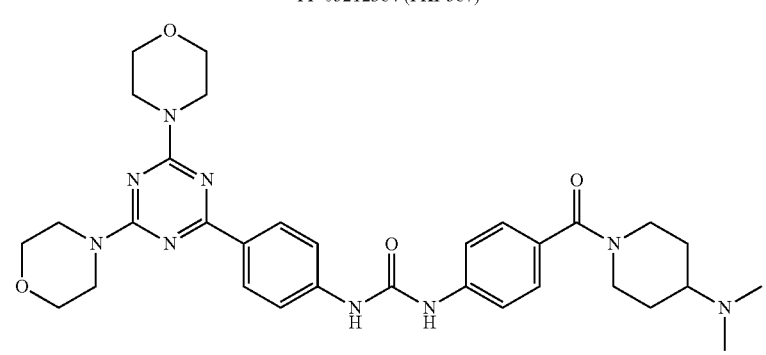 | PKI-587 is a highly potent dual inhibitor of PI3Kα, PI3Kγ and mTOR with IC50 of 0.4 nM, 5.4 nM and 1.6 nM, respectively. | |
| 22 | PP-121 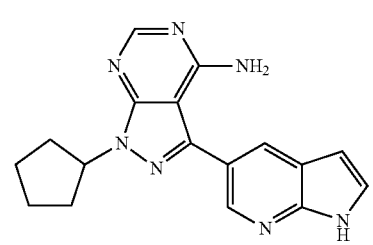<br>1-Cyclopentyl-3-(1H-pyrrolo[2,3-b]p-yridin-5-yl)-1H-pyrazolo[3,4-d]pyrimidin-4-amine | PP-121 is a multi-target inhibitor of PDGFR, Hck, mTOR, VEGFR2, Src and Abl with IC50 of 2 nM, 8 nM, 10 nM, 12 nM, 14 nM and 18 nM, respectively, and also inhibits DNA-PK with IC50 of 60 nM. | |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 23 | OSI-027(ASP4786) | OSI-027 is a selective and potent dual inhibitor of mTORC1 and mTORC2 with IC50 of 22 nM and 65 nM, respectively. | Exp Eye Res, 2013, 113C, 9-18 |
| 24 | Palomid 529(P529) | Palomid 529 inhibits both the mTORC1 and mTORC2 complexes, reduces phosphorylation of pAktS473, pGSK3βS9, and pS6 but neither pMAPK nor pAktT308. Phase 1. | |
| 25 | PP242<br><br>2-[4-Amino-1-(1-methylethyl)-1H-pyr-azolo[3,4-d]pyrimidin-3-yl]-1H-indol-5-ol | PP242 is a selective mTOR inhibitor with IC50 of 8 nM. | Autophagy, 2012, 8(6), 903-914 |
| 26 | XL765(SAR245409) | XL765 is a dual inhibitor of mTOR/PI3k for mTOR, p110α, p110β, p110γ and p110δ with IC50 of 157 nM, 39 nM, 113 nM, 9 nM and 43 nM, respectively. | Endocrinology, 2013, 154(3): 1247-59 |

TABLE A-continued

Exemplary mTOR inhibitor compounds which may be used in combination with thienotriazolodiazepine of Formula (1):

| No. | Inhibitor Name | Description | Literature Citations |
|---|---|---|---|
| 27 | GSK1059615<br><br>5-[[4-(4-Pyridinyl)-6-quinolinyl]me-thylene]-2,4-thiazolidenedione | GSK1059615 is a novel and dual inhibitor of PI3Kα, PI3Kβ, PI3Kδ, PI3Kγ and mTOR with IC50 of 0.4 nM, 0.6 nM, 2 nM, 5 nM and 12 nM, respectively. | Nature, 2012, 486(7404), 532-536 |
| 28 | WYE-354 | WYE-354 is a potent, specific and ATP-competitive inhibitor of mTOR with IC50 of 5 nM. | Mol Cancer Res, 2012, 10(6), 821-833. |
| 29 | Deforolimus (Ridaforolimus, MK-8669) | Deforolimus (Ridaforolimus; AP23573; MK-8669; 42-(Dimethylphosphinate) rapamycin; Ridaforolimus) is a selective mTOR inhibitor with IC50 of 0.2 nM. | Mol Genet Meta, 2010, 100(4), 309-315. |

In some embodiments the method further comprises administering to the patient an ALK inhibitor. In one such embodiment the ALK inhibitor is selected from the group consisting of ceritinib and crizotinib. In one such embodiment the ALK inhibitor is crizotinib. The thienotriazolodiazepine compound and the ALK inhibitor can be administered simultaneously or sequentially. In some embodiments such combination of thienotrizolodiazepine compound and ALK inhibitor produces a synergistic effect.

Example ALK inhibitors for use in combination with the thienotriazolodiazepine of Formula (1) in the methods of the present invention include, but are not limited to, the ALK inhibitors listed in the below Table B.

TABLE B

Exemplary ALK inhibitor compounds which may be used in combination with thienotriazolodiazepine of Formula (1):

| No. | Inhibitor Name | Description |
|---|---|---|
| 30 | Crizotinib | Xalkori; 3-[(1R)-1-(2,6-dichloro-3-fluorophenyl)ethoxy]-5-(1-piperidin-4-ylpyrazol-4-yl)pyridin-2-amine |
| 31 | Ceritinib | Zykadia; 5-Chloro-N2-[2-isopropoxy-5-methyl-4-(4-piperidinyl)phenyl]-N4-[2-(isopropylsulfonyl)phenyl]-2,4-pyrimidinediamine |
| 32 | Alectinib | |

TABLE B-continued
Exemplary ALK inhibitor compounds which may be used in combination with thienotriazolodiazepine of Formula (1):
| No. | Inhibitor Name | Description |
|---|---|---|
| 33 | Brigantinib | |
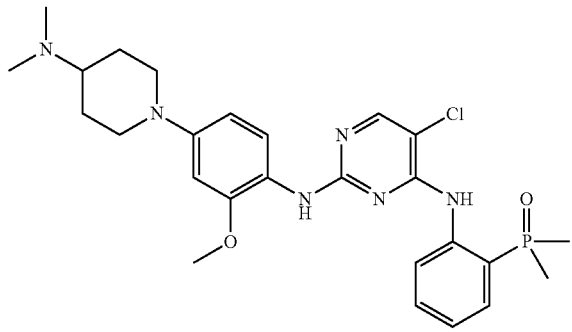
| 34 | Entrectinib | |
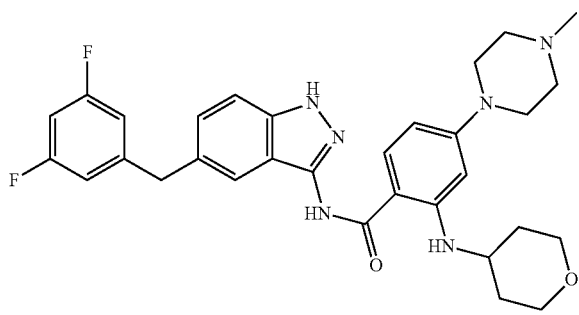
| 35 | PF-06463922 | |
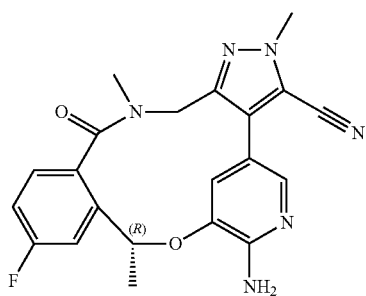

TABLE B-continued

Exemplary ALK inhibitor compounds which may be used in combination with thienotriazolodiazepine of Formula (1):

| No. | Inhibitor Name | | Description |
|---|---|---|---|
| 36 | CEP-37440 | 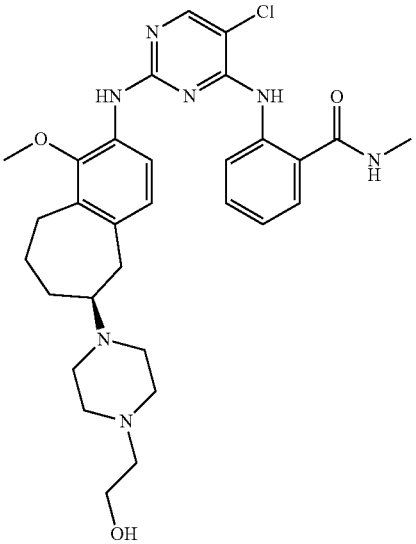 | 2-[[5-Chloro-2-[[(6S)-6-[4-(2-hydroxyethyl)piperazin-1-yl]-1-methoxy-6,7,8,9-tetrahydro-5H-benzo[7]annulen-2-yl]amino]pyrimidin-4-yl]amino]-N-methyl-benzamide |

In one embodiment, the thienotriazolodiazepine compound of the Formula (1) is formed as a solid dispersion. In one embodiment, the solid dispersion comprises an amorphous In the present invention, "treatment" or "treat" refers to an act or the action of administration of the active ingredient of the present invention to a person diagnosed by a doctor to have small cell lung cancer or be at risk of developing small cell lung cancer (patient), which aims, for example, to alleviate small cell lung cancer or symptom, prevent the onset of small cell lung cancer or symptom, or restore the state before onset of the small cell lung cancer.

III. Thienotriazolodiazepine Compounds:

In one embodiment, the thienotriazolodiazepine compounds, used in the formulations of the present invention, are represented by Formula (1):

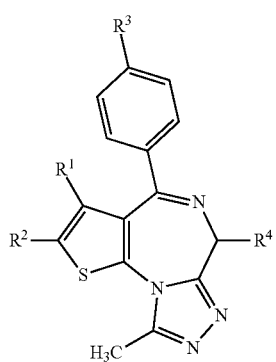

(1)

wherein
$R^1$ is alkyl having a carbon number of 1-4,
$R^2$ is a hydrogen atom; a halogen atom; or alkyl having a carbon number of 1-4 optionally substituted by a halogen atom or a hydroxyl group,
$R^3$ is a halogen atom; phenyl optionally substituted by a halogen atom, alkyl having a carbon number of 1-4, alkoxy having a carbon number of 1-4 or cyano; —$NR^5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—CO—$(CH_2)_n$—$R^8$ wherein $R^7$ is a hydrogen atom or alkyl having a carbon number of 1-4, n is an integer of 0-2, and $R^8$ is phenyl or pyridyl optionally substituted by a halogen atom, and
$R^4$ is —$(CH_2)_a$—CO—NH—$R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4, including any salts, isomers, enantiomers, racemates, hydrates, solvates, metabolites, and polymorphs thereof.

In one embodiment, a suitable alkyl group includes linear or branched akyl radicals including from 1 carbon atom up to 4 carbon atoms. In one embodiment, a suitable alkyl group includes linear or branched akyl radicals including from 1 carbon atom up to 3 carbon atoms. In one embodiment, a suitable alkyl group includes linear or branched akyl radicals include from 1 carbon atom up to 2 carbon atoms. In one embodiment, exemplary alkyl radicals include, but are not limited to, methyl, ethyl, propyl, isopropyl, n-butyl, isobutyl, sec-butyl, tert-butyl. In one embodiment, exemplary alkyl groups include, but are not limited to, methyl, ethyl, propyl, isopropyl, 2-methyl-1-propyl, and 2-methyl-2-propyl.

In some embodiments, the present invention provides pharmaceutically acceptable salts, solvates, including hydrates, and isotopically-labeled forms of the thienotriazolodiazepine compounds described herein. In one embodiment, pharmaceutically acceptable salts of the thienotriazolodiazepine compounds include acid addition salts formed with inorganic acids. In one embodiment, pharmaceutically acceptable inorganic acid addition salts of the thienotriazolodiazepine include salts of hydrochloric, hydrobromic, hydroiodic, phosphoric, metaphosphoric, nitric and sulfuric acids. In one embodiment, pharmaceutically acceptable salts of the thienotriazolodiazepine compounds include acid addition salts formed with organic acids. In one embodiment, pharmaceutically acceptable organic acid addition salts of the thienotriazolodiazepine include salts of tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and 4-methyl benzenesulfonic acids.

The present invention provides pharmaceutically acceptable isotopically-labeled forms of the thienotriazolodiazepine compounds, described herein, wherein one or more atoms are replaced by atoms having the same atomic number, but an atomic mass or mass number different from the atomic mass or mass number usually found in nature. Examples of isotopes suitable for inclusion in the thienotriazolodiazepine compounds include isotopes of hydrogen, e.g., $^{2}$H and $^{3}$H, carbon, e.g., $^{11}$C, $^{13}$C and $^{14}$C, chlorine, e.g., $^{36}$Cl, fluorine, e.g., $^{18}$F, iodine, e.g., $^{123}$I and $^{125}$I, nitrogen, e.g., $^{13}$N and $^{15}$N, oxygen, e.g., $^{15}$O, $^{17}$O and $^{18}$O, and sulfur, e.g., $^{35}$S. Isotopically-labeled forms of the thienotriazolodiazepine compounds generally can be prepared by conventional techniques known to those skilled in the art.

Certain isotopically-labeled forms of the compound of Formula (1), for example those incorporating a radioactive isotope, are useful in drug and/or substrate tissue distribution studies. The radioactive isotopes tritium ($^{3}$H) and carbon-14 ($^{14}$C) are particularly useful for this purpose in view of their ease of incorporation and ready means of detection. Substitution with heavier isotopes such as deuterium ($^{2}$H) may afford certain therapeutic advantages that result from greater metabolic stability, for example increased in vivo half-life or reduced dosage requirements, and hence may be preferred in some circumstances. Substitution with positron emitting isotopes, such as $^{11}$C, $^{18}$F, $^{15}$O, and $^{13}$N can be used in Positron Emission Tomography (PET) studies for examining substrate receptor occupancy.

In some embodiments, the thienotriazolodiazepine compounds disclosed herein can exist in solvated as well as unsolvated forms with pharmaceutically acceptable solvents. It will be understood by those skilled-in the art that a solvate is a complex of variable stoichiometry formed by a solute (in this case, the thienotriazolodiazepine compounds described herein) and a solvent. It is preferred that such solvents not interfere with the biological activity of the solute (the thienotriazolodiazepine compounds). Examples of suitable solvents for solvate formation include, but are not limited to, water, methanol, dimethyl sulfoxide, ethanol and acetic acid. Suitably the solvent used is a pharmaceutically acceptable solvent. Suitably the solvent used is water. In one embodiment, pharmaceutically acceptable solvates of the thienotriazolodiazepine compounds, described herein, include ethanol solvate, a isopropanol solvate, a dioxolane solvate, a tetrahydrofuran solvate, a dimethyl sulfoxide solvate, tert-butanol solvate, 2-butanol solvate, dioxolane solvate, 1,3-Dimethyl-3,4,5,6-tetrahydro-2(1H)-pyrimidinone ("DMPU") solvate, 1,3-dimethylimidazolidinone ("DMI") solvate, and 1,3-dimethylimidazolidinone ("DMP") solvate, or mixtures thereof.

In some embodiments, the thienotriazolodiazepine compounds, described herein, may contain one or more chiral centers and/or double bonds and, therefore, may exist as geometric isomers, enantiomers or diastereomers. The enantiomer and diastereomers of the thienotriazolodiazepine compounds may be designated in accordance with the Cahn-Ingold-Prelog convention, which assigns an "R" or "S" descriptor to each stereocenter (also sometimes referred to as a chiral center) and an E or Z descriptor to each carbon-carbon double bond (to designate geometric isomers) so that the configuration of the entire molecule can be specified uniquely by including the descriptors in its systematic name.

In some embodiments, the thienotriazolodiazepine compounds, described herein, may exist as a racemic mixture, or racemate, which includes equal amounts of left- and right-handed enantiomers of a chiral molecule. Such a racemic mixture may be denoted by the prefix (±)- or dl-, indicating an equal (1:1) mixture of dextro and levo isomers. Also, the prefix rac- (or racem-) or the symbols RS and SR may be used to designate the racemic mixture.

Geometric isomers, resulting from the arrangement of substituents around a carbon-carbon double bond or arrangement of substituents around a cycloalkyl or heterocyclic ring, can also exist in the compounds of the present invention. In some embodiments, the symbol ===== may be used to denote a bond that may be a single, double or triple bond. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of a plane of a ring are designated "cis/trans" or "Z/E."

In some embodiments, thienotriazolodiazepine compounds disclosed herein may exist in single or multiple crystalline forms or polymorphs. In one embodiment, a thienotriazolodiazepine compound disclosed herein comprises an amorphous form thereof. In one embodiment, a thienotriazolodiazepine compound disclosed herein comprises a single polymorph thereof. In another embodiment, a thienotriazolodiazepine compound disclosed herein comprises a mixture of polymorphs thereof. In another embodiment, the compound is in a crystalline form.

In some embodiments, thienotriazolodiazepine compounds disclosed herein may exist as a single enantiomers or in enatiomerically enriched forms. In one embodiment, a thienotriazolodiazepine compound disclosed herein exists in an entiomeric excess of more than 80%. In one embodiment, a thienotriazolodiazepine compound disclosed herein exists in an entiomeric excess of more than 90%. In one embodiment, a thienotriazolodiazepine compound disclosed herein exists in an entiomeric excess of more than 98%. In one embodiment, a thienotriazolodiazepine compound disclosed herein exists in an entiomeric excess of more than 99%. In some embodiments, a thienotriazolodiazepine compound disclosed herein exists in an entiomeric excess selected from the group consisting of at least 10%, at least 25%, at least 50%, at least 75%, at least 90%, at least 95%, at least 98%, at least and at least 99% enantiomeric excess.

For a pair of enantiomers, enantiomeric excess (ee) of enantiomer E1 in relation to enantiomer E2 can be calculated using the following equation eq. (1):

$$\% \text{ enantiomeric excess of } E1 = \frac{(E1 - E2) \times 100\%}{(E1 + E2)} \qquad \text{eq. (1)}$$

Relative amounts of E1 and E2 can be determined by chiral high performance liquid chromatography (HPLC), nuclear magnetic resonance (NMR) or any other suitable methods. In some embodiments, purity of an entiormeric compound may refer to the amount of the enantiomers E1 and E2, relative to the amount of other materials, which may notably include by-products and/or unreacted reactants or reagents.

In some embodiments, thienotriazolodiazepine compounds of Formula (1) include, but are not limited to, the thienotriazolodiazepine compounds (1-1) to (1-18), which are listed in the following Table C.

Compound (1-1) of Table C will be referred to herein as OTX-015, OTX015, or Y803.

TABLE C

Exemplary compounds which may be used in the formulations described herein:

(1-1)

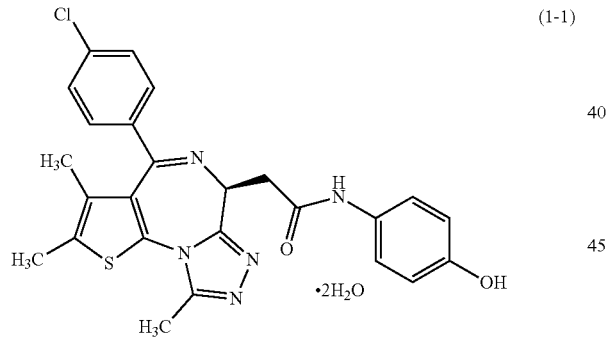

(1-2)

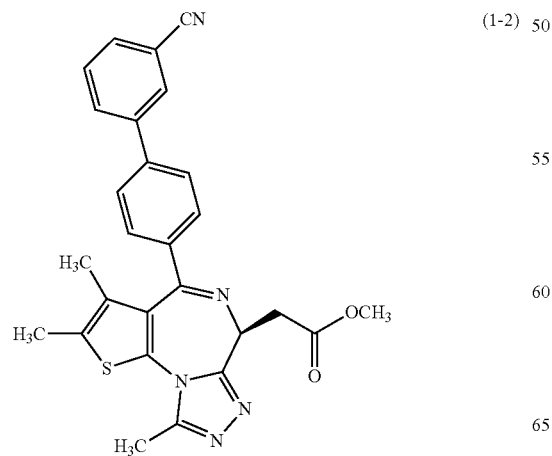

TABLE C-continued

Exemplary compounds which may be used in the formulations described herein:

(1-3)

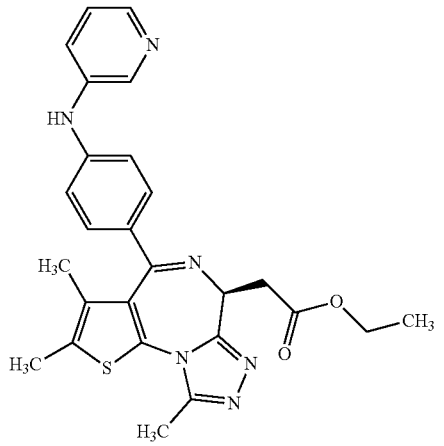 [SMILES: CCOC(=O)C[C@@H]1N=C(c2ccc(Nc3cccnc3)cc2)c2c(sc(C)c2C)-n2c(C)nnc21]

(1-4)

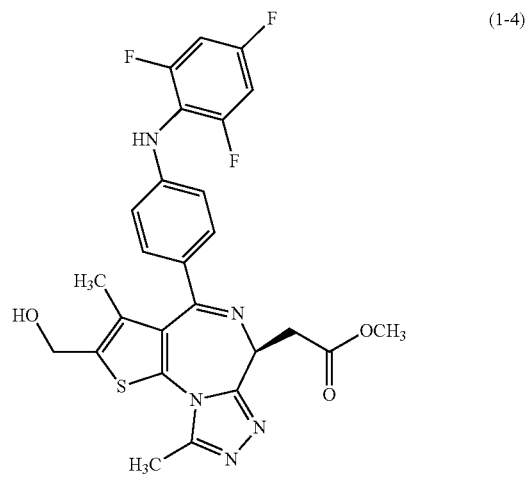

(1-5)

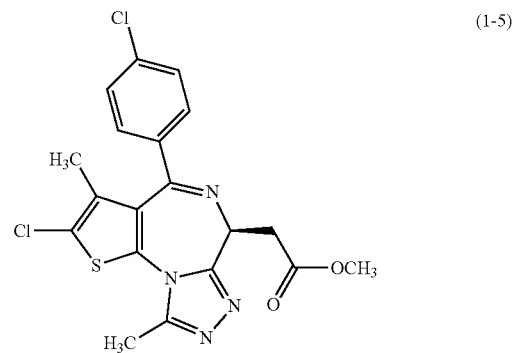

TABLE C-continued
Exemplary compounds which may be used in the formulations described herein:
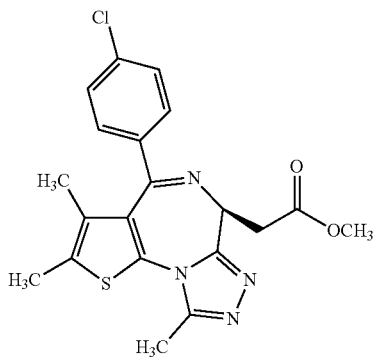 [SMILES: COC(=O)C[C@@H]1N=C(c2ccc(Cl)cc2)c2c(sc(C)c2C)-n2c(C)nnc21]
(1-6)
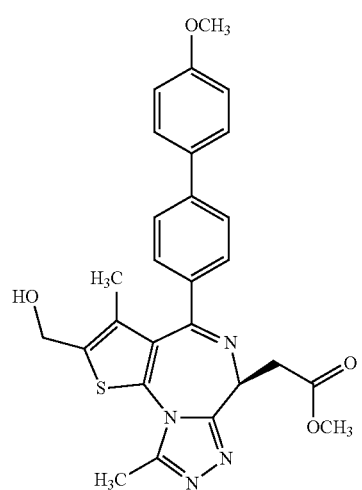 [SMILES: COC(=O)C[C@@H]1N=C(c2ccc(-c3ccc(OC)cc3)cc2)c2c(sc(CO)c2C)-n2c(C)nnc21]
(1-7)
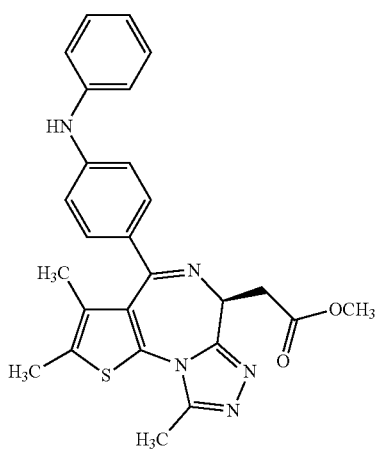 [SMILES: COC(=O)C[C@@H]1N=C(c2ccc(Nc3ccccc3)cc2)c2c(sc(C)c2C)-n2c(C)nnc21]
(1-8)
TABLE C-continued
Exemplary compounds which may be used in the formulations described herein:
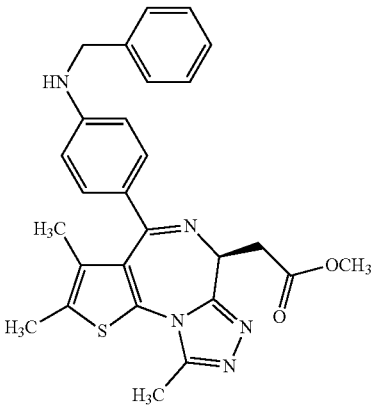 [SMILES: COC(=O)C[C@@H]1N=C(c2ccc(NCc3ccccc3)cc2)c2c(sc(C)c2C)-n2c(C)nnc21]
(1-9)
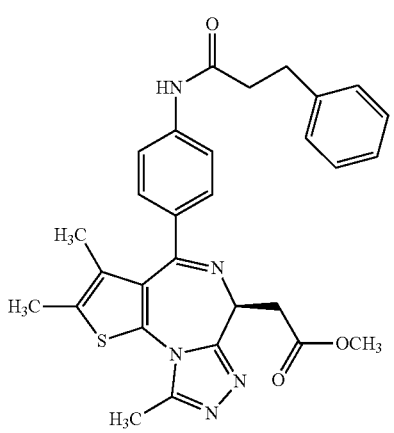 [SMILES: COC(=O)C[C@@H]1N=C(c2ccc(NC(=O)CCc3ccccc3)cc2)c2c(sc(C)c2C)-n2c(C)nnc21]
(1-10)
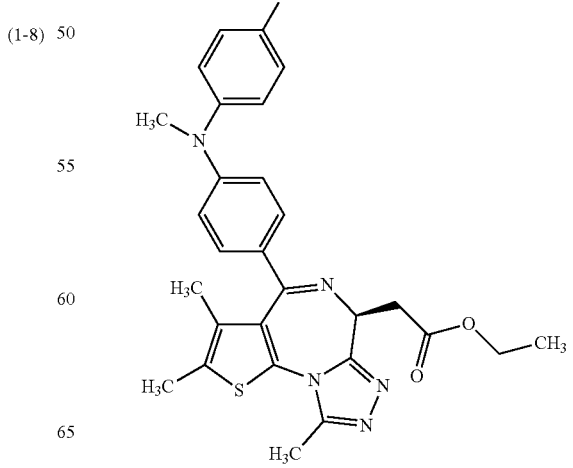
(1-11)

TABLE C-continued

Exemplary compounds which may be used in the formulations described herein:

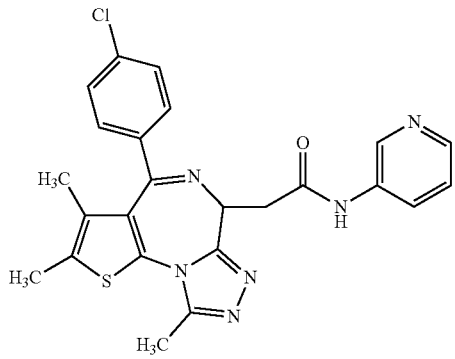 [SMILES: Cc1sc2c(c1C)C(c1ccc(Cl)cc1)=NC(CC(=O)Nc1cccnc1)c1nnc(C)n1-2]
(1-12)

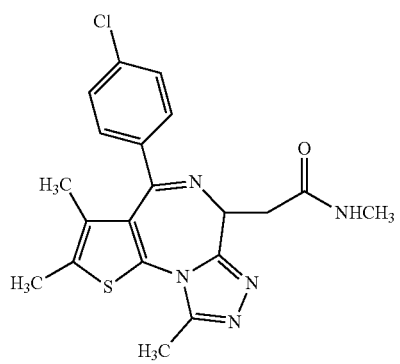 [SMILES: CNC(=O)CC1N=C(c2ccc(Cl)cc2)c2c(sc(C)c2C)-n2c(C)nnc21]
(1-13)

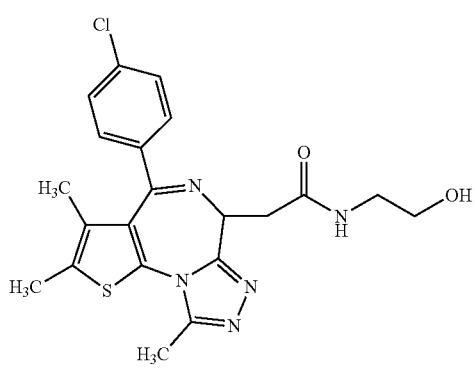 [SMILES: Cc1sc2c(c1C)C(c1ccc(Cl)cc1)=NC(CC(=O)NCCO)c1nnc(C)n1-2]
(1-14)

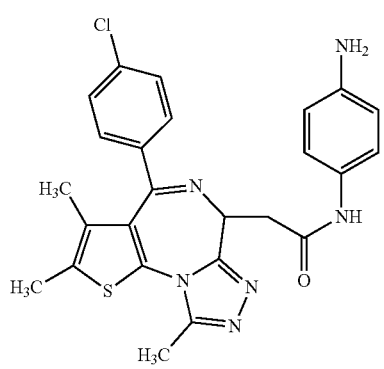 [SMILES: Cc1sc2c(c1C)C(c1ccc(Cl)cc1)=NC(CC(=O)Nc1ccc(N)cc1)c1nnc(C)n1-2]
(1-15)

TABLE C-continued

Exemplary compounds which may be used in the formulations described herein:

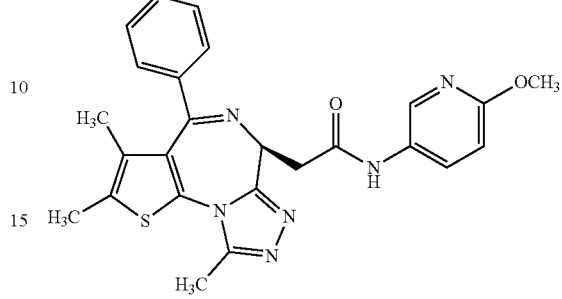
(1-16)

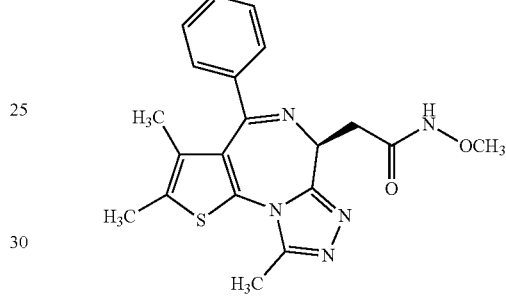
(1-17)

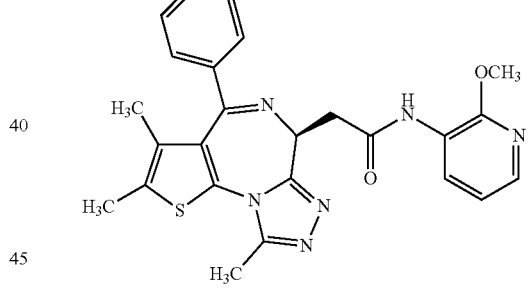
(1-18)

In some embodiments, thienotriazolodiazepine compounds of Formula (1) include (i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, (ii) methyl (S)-{4-(3'-cyanobiphenyl-4-yl)-2,3,9-trimethyl-6H-thieno[3,2-f][1,2,4]triazolo[4,3-a][1,4]diazepin-6-yl}acetate, (iii) methyl (S)-{2,3,9-trimethyl-4-(4-phenylaminophenyl)-6H-thieno[3,2-f][1,2,4]triazolo[4,3-a][1,4]diazepin-6-yl}acetate; and (iv) methyl (S)-{2,3,9-trimethyl-4-[4-(3-phenylpropionylamino)phenyl]-6H-thieno[3,2-f][1,2,4]triazolo[4,3-a][1,4]diazepin-6-yl}acetate.

In some embodiments, thienotriazolodiazepine compounds of Formula (1) include (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide.

In some embodiments, thienotriazolodiazepine compounds of Formula (1) include (S)-2-[4-(4-chlorophenyl)-2,3,9-trimethyl-6H-thieno[3,2-f][1,2,4]triazolo[4,3-a][1,4]diazepin-6-yl]-N-(4-hydroxyphenyl)acetamide dihydrate.

IV. Formulations:

The compound of Formula (1) presents highly specific difficulties in relation to administration generally and the preparation of galenic compositions in particular, including the particular problems of drug bioavailability and variability in inter- and intra-patient dose response, necessitating development of a non-conventional dosage form with respect to the practically water-insoluble properties of the compound.

Previously, it had been found that the compound of Formula (1) could be formulated as a solid dispersion with the carrier ethyl acrylate-methyl methacrylate-trimethylammonioethyl methacrylate chloride copolymer (Eudragit RS, manufactured by Rohm) to provide an oral formulation that preferentially released the pharmaceutical ingredient in the lower intestine for treatment of inflammatory bowel diseases such as ulcerative colitis and Crohn's disease (US Patent Application 20090012064 A1, published Jan. 8, 2009). It was found, through various experiments, including animal tests, that in inflammatory bowel diseases drug release in a lesion and a direct action thereof on the inflammatory lesion were more important than the absorption of the drug into circulation from the gastrointestinal tract.

It has now been unexpectedly found that thienotriazolodiazepine compounds, according to Formula (1), pharmaceutically acceptable salts, solvates, including hydrates, racemates, enantiomers isomers, and isotopically-labeled forms thereof, can be formulated as a solid dispersion with pharmaceutically acceptable polymers to provide an oral formulation that provides high absorption of the pharmaceutical ingredient into the circulation from the gastrointestinal tract for treatment of diseases other than inflammatory bowel diseases. Studies in both dogs and humans have confirmed high oral bioavailability of these solid dispersions compared with the Eudragit solid dispersion formulation previously developed for the treatment of inflammatory bowel disease.

Solid dispersions are a strategy to improve the oral bioavailability of poorly water soluble drugs.

The term "solid dispersion" as used herein refers to a group of solid products including at least two different components, generally a hydrophilic carrier and a hydrophobic drug, the thienotriazolodiazepine compounds, according to Formula (1). Based on the drug's molecular arrangement within the dispersion, six different types of solid dispersions can be distinguished. Commonly, solid dispersions are classified as simple eutectic mixtures, solid solutions, glass solution and suspension, and amorphous precipitations in a crystalline carrier. Moreover, certain combinations can be encountered, for example, in the same sample some molecules may be present in clusters while some are molecularly dispersed.

In one embodiment, the thienotriazolodiazepine compounds, according to Formula (1) can be dispersed molecularly, in amorphous particles (clusters). In another embodiment, the thienotriazolodiazepine compounds, according to Formula (1) can be dispersed as crystalline particles. In one embodiment, the carrier can be crystalline. In another embodiment, the carrier can be amorphous.

In one embodiment, the present invention provides a pharmaceutical composition comprising a solid dispersion of a thienotriazolodiazepine compound, in accordance with Formula (1), or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is hypromellose acetate succinate (also called hydroxypropylmethylcellulose acetate succinate or HPMCAS). In one embodiment, the dispersion has a thienotriazolodiazepine compound to hydroxypropylmethylcellulose acetate succinate (HPMCAS) weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, the present invention provides a pharmaceutical composition comprising a solid dispersion of a thienotriazolodiazepine compound of Formula (1) or a pharmaceutically acceptable salt, a solvate, including a hydrate, a racemate, an enantiomer, an isomer, or an isotopically-labeled form thereof in a pharmaceutically acceptable polymer. In one embodiment, the pharmaceutically acceptable polymer is polyvinylpyrrolidone (also called povidone or PVP). In one embodiment, the dispersion has a thienotriazolodiazepine compound to PVP weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to about 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to about 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1.

In one embodiment, a pharmaceutical composition of the present invention comprises a solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1.

In some embodiments, a pharmaceutical composition comprising a solid dispersion is prepared by spray drying.

In one embodiment, a pharmaceutical composition of the present invention comprises a spray dried solid dispersion of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of compound (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21°2-theta associated with crystalline thienotriazolodiazepine compound of Formula (1).

In one embodiment, a pharmaceutical composition of the present invention comprises a spray dried solid dispersion of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of compound (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In some such embodiments, the solid dispersion was exposed to a relative humidity of 75% at 40° C. for at least one month. In other such embodiments, the single Tg occurs at about 135° C. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1.

In one embodiment, a pharmaceutical composition of the present invention comprises a spray dried solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1.

In one preferred embodiment, the present invention provides a pharmaceutical composition comprising a solid dispersion of 2-[(6S)-4-(4-chlorophenyl)-2,3,9-trimethyl-6H-thienol[3,2-f]-[1,2,4]triazolo[4,3-a][1,4]diazepin-6-yl]-N-(4-hydroxyphenyl)acetamide dihydrate, compound (1-1):

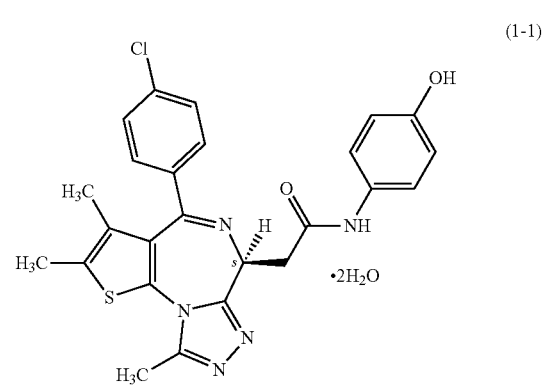 [SMILES: Cc1sc2c(c1C)C(c1ccc(Cl)cc1)=N[C@@H](CC(=O)Nc1ccc(O)cc1)c1nnc(C)n1-2]

(1-1)

or a pharmaceutically acceptable salt, a solvate, including a hydrate, a racemate, an enantiomer, an isomer, or an isotopically-labeled form and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In another embodiment, the pharmaceutical composition comprises a solid dispersion compound (1-1) or a pharmaceutically acceptable salt, a solvate, including a hydrate, a racemate, an enantiomer, an isomer, or an isotopically-labeled form; and a pharmaceutically acceptable polymer. In one embodiment, the pharmaceutically acceptable polymer is PVP. In one embodiment, the dispersion has compound (1-1) and PVP in weight ratio 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of an amorphous form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of an amorphous form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is PVP. In one embodiment, the dispersion has compound (1-1) and PVP in weight ratio 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 175° C. to 185° C. In other such embodiments, the single Tg occurs at about 189° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of a crystalline form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, the solid dispersion is spray dried.

In one embodiment, a pharmaceutical composition of the present invention comprises a solid dispersion of a crystalline form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is PVP. In one embodiment, the dispersion has compound (1-1) and PVP in weight ratio 1:3 to 1:1. In one embodiment, the solid dispersion is spray dried.

The solid dispersions of the invention, described herein, exhibit especially advantageous properties when administered orally. Examples of advantageous properties of the solid dispersions include, but are not limited to, consistent and high level of bioavailability when administered in standard bioavailability trials in animals or humans. The solid dispersions of the invention can include a solid dispersion comprising thienotriazolodiazepine compound of Formula (1) and a polymer and additives. In some embodiments, the solid dispersions can achieve absorption of the thienotriazolodiazepine compound of Formula (1) into the bloodstream that cannot be obtained by merely admixing the thienotriazolodiazepine compound of Formula (1) with additives since the thienotriazolodiazepine compound of Formula (1) drug has negligible solubility in water and most aqueous media. The bioavailability, of thienotriazolodiazepine compound of Formula (1) or of thienotriazolodiazepine compound (1-1) may be measured using a variety of in vitro and/or in vivo studies. The in vivo studies may be performed, for example, using rats, dogs or humans.

The bioavailability may be measured by the area under the curve (AUC) value obtained by plotting a serum or plasma concentration, of the thienotriazolodiazepine compound of Formula (1) or thienotriazolodiazepine compound (1-1), along the ordinate (Y-axis) against time along the abscissa (X-axis). The AUC value of the thienotriazolodiazepine compound of Formula (1) or thienotriazolodiazepine compound (1-1) from the solid dispersion, is then compared to the AUC value of an equivalent concentration of crystalline thienotriazolodiazepine compound of Formula (1) or crystalline thienotriazolodiazepine compound (1-1) without polymer. In some embodiments, the solid dispersion provides an area under the curve (AUC) value, when administered orally to a dog, that is selected from: at least 0.4 times, 0.5 times, 0.6 times, 0.8 times, 1.0 times, a corresponding AUC value provided by a control composition administered intravenously to a dog, wherein the control composition comprises an equivalent quantity of a crystalline thienotriazolodiazepine compound of Formula (1).

The bioavailability may be measured by in vitro tests simulating the pH values of a gastric environment and an intestine environment. The measurements may be made by suspending a solid dispersion of the thienotriazolodiazepine compound of Formula (1) or thienotriazolodiazepine compound (1-1), in an aqueous in vitro test medium having a pH between 1.0 to 2.0, and the pH is then adjusted to a pH between 5.0 and 7.0, in a control in vitro test medium. The concentration of the amorphous thienotriazolodiazepine compound of Formula (1) or amorphous thienotriazolodiazepine compound (1-1) may be measured at any time during the first two hours following the pH adjustment. In some embodiments, the solid dispersion provides a concentration, of the amorphous thienotriazolodiazepine compound of Formula (1) or amorphous thienotriazolodiazepine compound (1-1), in an aqueous in vitro test medium at pH between 5.0 to 7.0 that is selected from: at least 5-fold greater, at least 6 fold greater, at least 7 fold greater, at least 8 fold greater, at least 9 fold greater or at least 10 fold greater, compared to a concentration of a crystalline thienotriazolodiazepine compound of Formula (1) or crystalline thienotriazolodiazepine compound (1-1), without polymer.

In other embodiments, the concentration of the amorphous thienotriazolodiazepine compound of Formula (1) or amorphous thienotriazolodiazepine compound (1-1), from the solid dispersion placed in an aqueous in vitro test medium having a pH of 1.0 to 2.0, is: at least 40%, at least 50%, at least 60%, at least 70%; at least 80%, higher than a concentration of a crystalline thienotriazolodiazepine compound of Formula (1) without polymer. In some such embodiments, the polymer of the solid dispersion is HPMCAS. In some such embodiments, the polymer of the solid dispersion is PVP.

In other embodiments, a concentration of the amorphous thienotriazolodiazepine compound of Formula (1) or amorphous thienotriazolodiazepine compound (1-1), from the solid dispersion, is: at least 40%, at least 50%, at least 60%, at least 70%; at least 80%, higher compared to a concentration of thienotriazolodiazepine compound of Formula (1), from a solid dispersion of thienotriazolodiazepine compound of the Formula (1) and a pharmaceutically acceptable polymer selected from the group consisting of: hypromellose phthalate and ethyl acrylate-methyl methacrylate-trimethylammonioethyl methacrylate chloride copolymer, wherein each solid dispersion was placed in an aqueous in vitro test medium having a pH of 1.0 to 2.0. In some such embodiments, the polymer of the solid dispersion is HPMCAS. In some such embodiments, the polymer of the solid dispersion is PVP.

In some embodiments, the solid dispersions, described herein, exhibit stability against recrystallization of the thienotriazolodiazepine compound of the Formula (1) or the thienotriazolodiazepine compound (1-1) when exposed to humidity and temperature over time. In one embodiment, the concentration of the amorphous thienotriazolodiazepine compound of the Formula (1) or the thienotriazolodiazepine compound (1-1) which remains amorphous is selected from: at least 90%, at least 91%, at least 92%, at least 93%, at least 94%, at least 95%, at least 96%, at least 97%, at least 98% and at least 99%.

V. Dosage Forms:

Suitable dosage forms that can be used with the solid dispersions of the present invention include, but are not limited to, capsules, tablets, mini-tablets, beads, beadlets, pellets, granules, granulates, and powder. Suitable dosage forms may be coated, for example using an enteric coating. Suitable coatings may comprise but are not limited to cellulose acetate phthalate, hydroxypropylmethylcellulose (HPMC), hydroxypropylmethylcellulose phthalate, a polymethylacrylic acid copolymer, or hydroxylpropylmethylcellulose acetate succinate (HPMCAS). In some embodiments, certain combinations can be encountered, for example, in the same sample some molecules of the thienotriazolodiazepine of the present invention may be present in clusters while some are molecularly dispersed with a carrier.

In some embodiments, the solid dispersions of the invention may be formulated as tablets, caplets, or capsules. In one some embodiments, the solid dispersions of the invention may be formulated as mini-tablets or pour-into-mouth granules, or oral powders for constitution. In some embodiments, the solid dispersions of the invention are dispersed in a suitable diluent in combination with other excipients (e.g., re-crystallization/precipitation inhibiting polymers, taste-masking components, etc.) to give a ready-to-use suspension formulation. In some embodiments, the solid dispersions of the invention may be formulated for pediatric treatment.

In one embodiment, the pharmaceutical composition of the present invention is formulated for oral administration. In one embodiment, the pharmaceutical composition comprises a solid dispersion, according to the various embodiments described herein, comprising a thienotriazolodiazepine compound of Formula (1) or a pharmaceutically acceptable salt, a solvate, including a hydrate, a racemate, an enantiomer, an isomer, or an isotopically-labeled form thereof; and a polymer carrier. In one embodiment, the pharmaceutical composition further includes one or more additives such as disintegrants, lubricants, glidants, binders, and fillers.

Examples of suitable pharmaceutically acceptable lubricants and pharmaceutically acceptable glidants for use with the pharmaceutical composition include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose, glyceryl behenate, stearic acid, hydrogenated castor oil, glyceryl monostearate, and sodium stearyl fumarate.

Examples of suitable pharmaceutically acceptable binders for use with the pharmaceutical composition include, but are not limited to starches; celluloses and derivatives thereof, e.g., microcrystalline cellulose (e.g., AVICEL PH from FMC), hydroxypropyl cellulose, hydroxyethyl cellulose, and hydroxylpropylmethylcellulose (HPMC, e.g., METHOCEL from Dow Chemical); sucrose, dextrose, corn syrup; polysaccharides; and gelatin.

Examples of suitable pharmaceutically acceptable fillers and pharmaceutically acceptable diluents for use with the pharmaceutical composition include, but are not limited to, confectioner's sugar, compressible sugar, dextrates, dextrin, dextrose, lactose, mannitol, microcrystalline cellulose (MCC), powdered cellulose, sorbitol, sucrose, and talc.

In some embodiments, excipients may serve more than one function in the pharmaceutical composition. For example, fillers or binders may also be disintegrants, glidants, anti-adherents, lubricants, sweeteners and the like.

In some embodiments, the pharmaceutical compositions of the present invention may further include additives or ingredients, such as antioxidants (e.g., ascorbyl palmitate, butylated hydroxylanisole (BHA), butylated hydroxytoluene (BHT), □-tocopherols, propyl gallate, and fumaric acid), antimicrobial agents, enzyme inhibitors, stabilizers (e.g., malonic acid), and/or preserving agents.

Generally, the pharmaceutical compositions of the present invention may be formulated into any suitable solid dosage form. In some embodiments, the solid dispersions of the invention are compounded in unit dosage form, e.g., as a capsule, or tablet, or a multi-particulate system such as granules or granulates or a powder, for administration.

In one embodiment, a pharmaceutical compositions includes a solid dispersion of a thienotriazolodiazepine compound of Formula (1), according to the various embodiments of solid dispersions described herein, and hydroxypropylmethylcellulose acetate succinate (HPMCAS), wherein the thienotriazolodiazepine compound is amorphous in the solid dispersion and has a thienotriazolodiazepine compound to hydroxypropylmethylcellulose acetate succinate (HPMCAS), weight ratio of 1:3 to 1:1; 45-50 wt. % of lactose monohydrate; 35-40 wt. % of microcrystalline cellulose; 4-6 wt. % of croscarmellose sodium; 0.8-1.5 wt. % of colloidal silicon dioxide; and 0.8-1.5 wt. % of magnesium stearate.

VI. Dosage:

In one embodiment, the present invention provides a pharmaceutical composition that maybe formulated into any suitable solid dosage form. In one embodiment, a pharmaceutical composition in accordance with the present invention comprises one or more of the various embodiments of the thienotriazolodiazepine of Formula (1) as described herein in a dosage amount ranging from about 10 mg to about 100 mg. In one embodiment, the pharmaceutical composition of the present invention includes one or more of the various embodiments of the thienotriazolodiazepine of Formula (1) as described herein in a dosage amount selected from the group consisting of from about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, and about 10 mg to about 20 mg. In one embodiment, the pharmaceutical composition of the present invention includes one or more of the various embodiments of the thienotriazolodiazepine of Formula (1) as described herein in a dosage amount selected from the group consisting of about 10 mg, about 50 mg, about 75 mg, about 100 mg.

In one embodiment, the pharmaceutical composition of the present invention includes administering to a subject in need thereof one or more of the various embodiments of the thienotriazolodiazepine of Formula (I) as described herein in a dosage amount selected from the group consisting of about 1 mg, about 2 mg, about 2.5 mg, about 3 mg, about 4 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, and about 150 mg, and in a dosage form selected from the group consisting of once weekly, once daily every sixth day, once daily every fifth day, once daily every fourth day, once daily every third day, once daily every other day, once daily, twice daily, three times daily, four times daily, and five times daily. In another embodiment, any of the foregoing dosage amounts or dosage forms is decreased periodically or increased periodically. In one embodiment, the pharmaceutical composition of the present invention includes administering to a subject in need thereof a thienotriazolodiazepine selected from the group consisting of compounds (1-1), (1-2), (1-3), (1-4), (1-5), (1-6), (1-7), (1-8), (1-9), (1-10), (1-11), (1-12), (1-13), (1-14), (1-15), (1-16), (1-17), and (1-18), in a dosage amount selected from the group consisting of about 1 mg, about 2 mg, about 2.5 mg, about 3 mg, about 4 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, and about 150 mg, and in a dosage form selected from the group consisting of once weekly, once daily every sixth day, once daily every fifth day, once daily every fourth day, once daily every third day, once daily every other day, once daily, twice daily, three times daily, four times daily, and five times daily. In another embodiment, any of the foregoing dosage amounts or dosage forms is decreased periodically or increased periodically.

Such unit dosage forms are suitable for administration 1 to 5 times daily depending on the particular purpose of therapy, the phase of therapy, and the like. In one embodiment, the dosage form may be administered to a subject in need thereof at least once daily for at least two successive days. In one embodiment, the dosage form may be administered to a subject in need thereof at least once daily on alternative days. In one embodiment, the dosage form may be administered to a subject in need thereof at least weekly and divided into equal and/or unequal doses. In one embodiment, the dosage form may be administered to a subject in need thereof weekly, given either on three alternate days and/or 6 times per week. In one embodiment, the dosage form may be administered to a subject in need thereof in divided doses on alternate days, every third day, every fourth day, every fifth day, every sixth day and/or weekly. In one embodiment, the dosage form may be administered to a subject in need thereof two or more equally or unequally divided doses per month.

The dosage form used, e.g., in a capsule, tablet, mini-tablet, beads, beadlets, pellets, granules, granulates, or powder may be coated, for example using an enteric coating. Suitable coatings may comprise but are not limited to cellulose acetate phthalate, hydroxypropylmethylcellulose (HPMC), hydroxypropylmethylcellulose phthalate, a polymethylacrylic acid copolymer, or hydroxylpropylmethylcellulose acetate succinate (HPMCAS).

VII. Process:

The thienotriazolodiazepine compounds disclosed herein can exist as free base or as acid addition salt. They can be obtained according to the procedures described in US Patent Application Publication No. 2010/0286127, incorporated by reference in its entirety herein, or in the present application. Individual enantiomers and diastereomers of the thienotriazolodiazepine compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase gas chromatography or crystallizing the compound in a chiral solvent.

If desired, a particular enantiomer of the thienotriazolodiazepine compounds disclosed herein may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers, thus formed by fractional crystallization or chromatographic means well known in the art, and subsequent recovery of the pure enantiomers. Various methods well known in the art may be used to to prepare the thienotriazolodiazepine compounds of Formula (1) with an enantiomeric excess of generally more than about 80%. Advantageously, preferred enantiomeric excess is of more than 80%, preferably of more than 90%, more preferably of more than 95%, and most preferably of 99% and more.

The solid dispersions of the present invention can be prepared by a number of methods, including by melting and solvent evaporation. The solid dispersions of the present invention can also be prepared according to the procedures described in: Chiou W L, Riegelman S: "Pharmaceutical applications of solid dispersion systems", *J. Pharm. Sci.* 1971; 60:1281-1302; Serajuddin A T M: "Solid dispersion of poorly water-soluble drugs: early promises, subsequent problems, and recentbreakthroughs", *J. Pharm. Sci.* 1999; 88:1058-1066; Leuner C, Dressman J: "Improving drug solubility for oral delivery using solid dispersions", *Eur. J. Pharm. Biopharm.* 2000; 50:47-60; and Vasconcelos T, Sarmento B, Costa P: "Solid dispersions as strategy to improve oral bioavailability of poor water soluble drugs", *Drug Discovery Today* 2007; 12:1068-1075, all of which are incorporated herein by reference in their entireties.

In one embodiment, solid dispersions of the present invention are prepared by a melting process. In one embodiment, the melting process comprises melting one or more of the various embodiments of the thienotriazolodiazepine of Formula (1) within a carrier. In one embodiment, the melting process includes cooling a melted compound of the present invention and a carrier. In one embodiment, the melting process comprises pulverization of the melted compound and the carrier. In one embodiment, a melted compound of the present invention and a carrier are pulverized following the cooling step.

In some embodiments in which the thienotriazolodiazepine of Formula (1) or a pharmaceutically acceptable salt, a solvate, including a hydrate, a racemate, an enantiomer, an isomer, or an isotopically-labeled form thereof and the carrier are incompatible, a surfactant may be added during the melting step to prevent formation of two liquid phases or a suspension in the heated mixture. In some embodiments, one or more of the various embodiments of the thienotriazolodiazepine of Formula (1) is suspended in a previously melted carrier, instead of using both drug and carrier in the melted state, thereby reducing the process temperature. In one embodiment, melted drug and carrier mixture is cooled an ice bath agitation. In one embodiment, melted drug and carrier mixture is cooled and solidified by spray cooling (alternatively spray congealing).

In one embodiment, melted drug and carrier mixture is cooled and solidified by forming the melt into particles by spraying the melt into a cooling chamber through which ambient or cooled, low temperature air is passing. In one embodiment, melted drug and carrier mixture is cooled and solidified by atomization and re-solidification of the molten dispersion in a suitable fluid bed processor. In one embodiment, melted drug and carrier mixture is cooled and solidified by melt-granulation in a heatable high-shear mixer.

In some embodiments, hot-stage extrusion or melt agglomeration may be used to avoid melting limitations of the drug. Hot-stage extrusion consists of the extrusion, at high rotational speed, of the drug and carrier, previously mixed, at melting temperature for a short period of time; the resulting product is collected after cooling at room temperature and milled.

In one embodiment, one or more of the various embodiments of the thienotriazolodiazepine of Formula (1) is processed at a reduced processing temperature to avoid degradation of any thermally labile compound. In one embodiment, the reduced processing temperature is achieved by associating a hot-stage extrusion with a temporary plasticizer such as carbon dioxide. In one embodiment, melt agglomeration is used in the preparation of solid dispersions in accordance with the present invention in conventional high shear mixers or in a rotary processors. In one embodiment, the solid dispersion in accordance with the present invention is prepared by adding a molten carrier containing a thienotriazolodiazepine compound in accordance with the present invention to a heated excipient. In one embodiment, the solid dispersion in accordance with the present invention is prepared by adding by adding a molten carrier to a heated mixture of the thienotriazolodiazepine in accordance with the present invention and one or more excipients. In one embodiment, the solid dispersion in accordance with the present invention is prepared by heating a mixture of a thienotriazolodiazepine compound in accordance with the present invention, a carrier and one or more excipients to a temperature within or above the melting range of the carrier.

In some embodiments, a one or more of the various embodiments for the formulation of the thienotriazolodiazepine, according to Formula (1), is prepared by a solvent evaporation method. In one embodiment, the solvent evaporation method comprises solubilization of a thienotriazolodiazepine compound, according to Formula (1), and carrier in a volatile solvent that is subsequently evaporated. In one embodiment, the volatile solvent may one or more excipients. In one embodiment, the one or more excipients include, but are not limited to anti-sticking agents, inert fillers, surfactants wetting agents, pH modifiers and additives. In one embodiment, the excipients may dissolved or in suspended or swollen state in the volatile solvent.

In one embodiment, preparation of solid dispersions in accordance with the present invention includes drying one or more excipients suspended in a volatile solvent. In one embodiment, the drying includes vacuum drying, slow evaporation of the volatile solvent at low temperature, use of a rotary evaporator, spray-drying, spray granulation, freeze-drying, or use of supercritical fluids.

In one embodiment, spray drying preparation of a formulation for the thienotriazolodiazepine composition, according to Formula (1), is used which involves atomization of a suspension or a solution of the composition into small droplets, followed by rapid removal solvent from the formulation. In one embodiment, preparation of a formulation in accordance with the present invention involves spray granulation in which a solution or a suspension of the composition in a solvent is sprayed onto a suitable chemically and/or physically inert filler, such as lactose or mannitol. In one embodiment, spray granulation of the solution or the suspension of the composition is achieved via two-way or three-way nozzles.

In some embodiments, preparation of solid dispersions in accordance with the present invention includes use of supercritical fluids. The term "supercritical fluids" refers to substances existing as a single fluid phase above their critical temperature and critical pressure. In one embodiment, preparation of a formulation, in accordance with the present invention, includes use a supercritical carbon dioxide fluid. In one embodiment, preparation of a formulation, in accordance with the present invention, using the supercritical fluid technique comprises dissolving a thienotriazolodiazepine compound, according to Formula (1), and carrier in a common solvent that is introduced into a particle formation vessel through a nozzle, simultaneously with carbon dioxide; and spraying the solution to allow the solvent be rapidly extracted by the supercritical fluid, thereby resulting in the precipitation of solid dispersion particles on the walls of the vessel.

In some embodiments, preparation of solid dispersions in accordance with the present invention includes use of a co-precipitation method. In one embodiment, a non-solvent is added dropwise to a thienotriazolodiazepine composition, according to Formula (1), and a carrier solution, under constant stirring. In one embodiment, the thienotriazolodiazepine composition, according to Formula (1), and the carrier are co-precipitated to form microparticles during the addition of the non-solvent. In one embodiment, the resulting microparticles are filtered and dried to provide the desired solid dispersion.

The proportion of compound of Formula (1) and polymeric carrier(s) to be mixed is not particularly limited, as long as it can improve the bioavailability of the compound of Formula (1) and varies depending on the kind of polymer.

The invention is illustrated in the following non-limiting examples.

VIII. Examples:

Example 1

In Vitro Screening of Solid Dispersions of Compound (1-1)

Ten solid dispersions were prepared using compound (1-1) and one of five polymers, including hypromellose acetate succinate (HPMCAS-M), hypromellose phthalate (HPMCP-HP55), polyvinylpyrrolidone (PVP), PVP-vinyl acetate (PVP-VA), and Euragit L100-55, at both 25% and 50% of compound (1-1) loading, for each polymer. Solid dispersions were prepared by a solvent evaporation method, using spray-drying followed by secondary drying in a low-temperature convection oven. The performance of each solid dispersion was assessed via a non-sink dissolution performance test which measured both the total amount of drug and the amount of free drug present in solution over time. Non-sink dissolution was chosen because it best represents the in vivo situation for low soluble compounds. This test included a "gastric transfer" of dispersion from gastric pH (0.1N NaCl, pH 1.0) to intestinal pH (FaFSSIF, pH 6.5) approximately 30 to 40 minutes after the introduction of dispersion to the test medium, simulating in vivo conditions. [FaFSSIF is Fasted State Simulated Intestinal Fluid, comprised of 3 mM sodium taurocholate, 0.75 mM lechithin, 0.174 g NaOH pellets, 1.977 g $NaH_2PO_4.H_2O$, 3.093 g NaCl, and purified water qs 500 mL.] The amount of dissolved drug was quantified using a high-performance liquid chromatography (HPLC) method and an Agilent 1100 series HPLC. The dissolution profiles of the formulations (FIGS. 1A-1J) showed large increases in drug solubility in all dispersion candidates relative to the unformulated compound in the same media. Of the solid dispersions, the 25% compound (1-1) in PVP, 25% compound (1-1) in HPMCAS-M, and 50% compound (1-1) in HPMCAS-M dispersions provided enhanced oral absorption as compared to the unformulated compound, based on finding higher levels of free drug released at intestinal pH.

Example 2

In Vivo Screening of Solid Dispersions of Compound (1-1)

The solid dispersions of compound (1-1), namely the 25% compound (1-1) in PVP, 25% compound (1-1) in HPMCAS-MG, and 50% compound (1-1) in HPMCAS-M dispersions, were prepared at larger scale for in vivo studies. Each formulation was assessed in the in vitro dissolution test described in Example 1. To ensure that these dispersions were both amorphous and homogeneous, each dispersion was assessed by powder x-ray diffraction (PXRD) and modulated differential scanning calorimetry (mDSC). The x-ray diffractomer was a Bruker D-2 Phaser. Additionally, to understand the effect of water on the glass transition temperature (Tg) for each dispersion, mDSC was performed on samples first equilibrated at a set relative humidity (i.e., 25%, 50%, and 75% RH) for at least 18 hours. Water can act as a plasticizer for solid dispersions and the hygroscopicity of the system due to the active compound or polymer can affect the amount of water uptake by these systems.

Figure 2A:
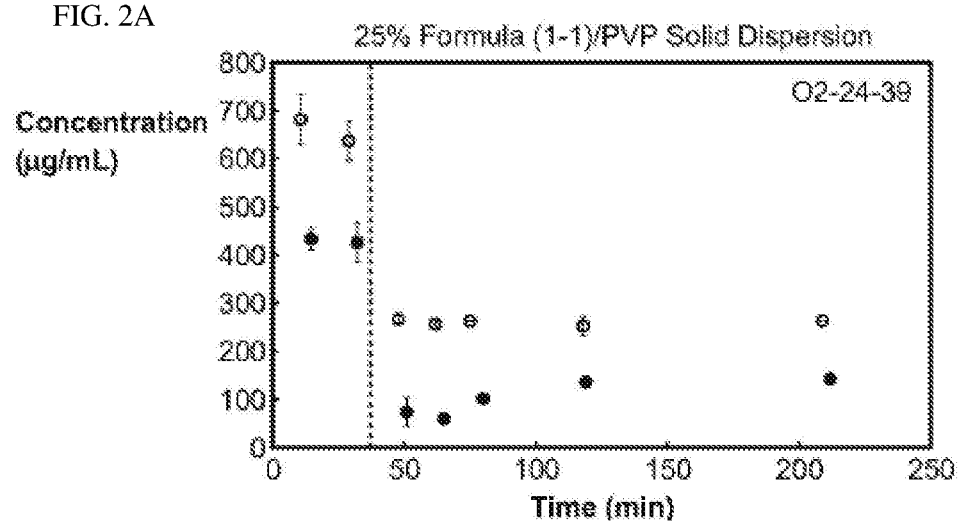
FIG. 2A illustrates results of in vivo screening of an exemplary formulation comprising a solid dispersion of 25% compound (1-1) and PVP.
Figure 2B:
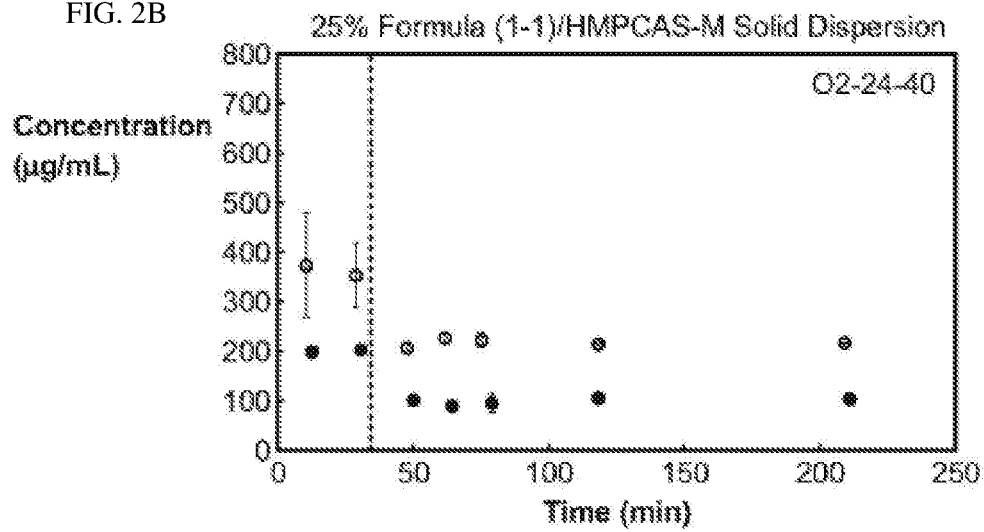
FIG. 2B illustrates results of an in vivo screening of an exemplary formulation comprising a solid dispersion of 25% compound (1-1) and HMPCAS-M.
Figure 2C:
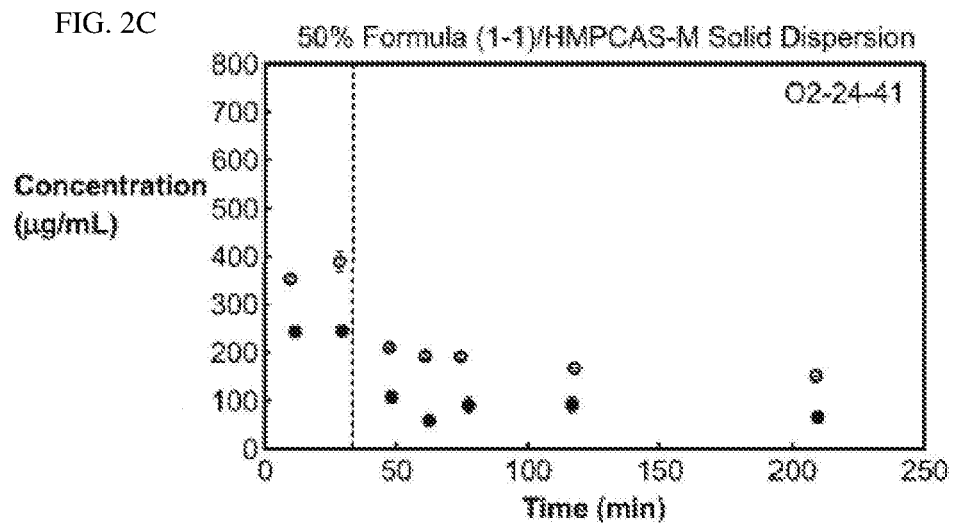
FIG. 2C illustrates results of an in vivo screening of an exemplary formulation comprising a solid dispersion of 50% compound (1-1) and HMPCAS-M.
Figure 3:
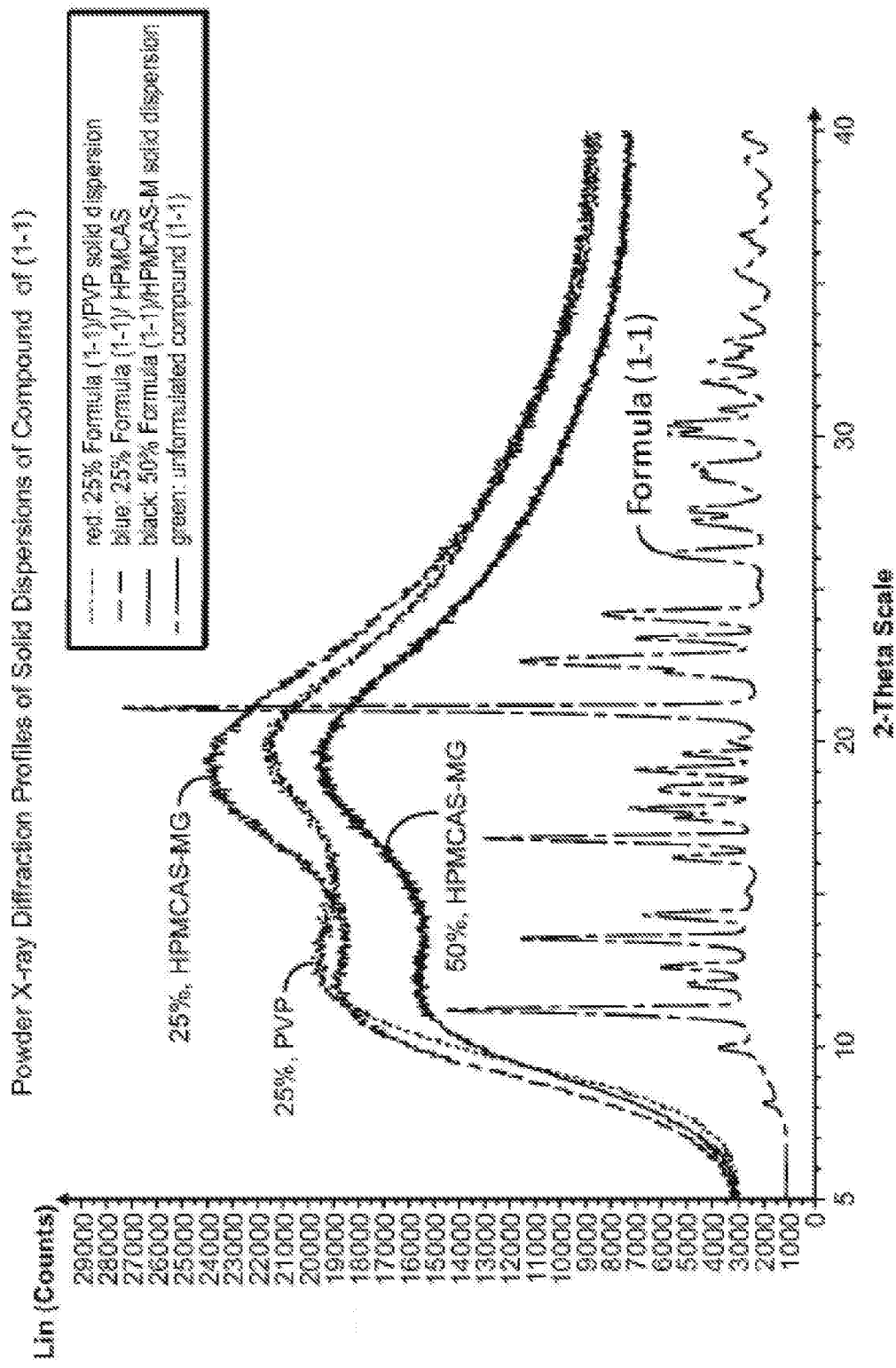
FIG. 3 illustrates powder X-ray diffraction profiles of solid dispersions of compound (1-1)
Figure 4A:
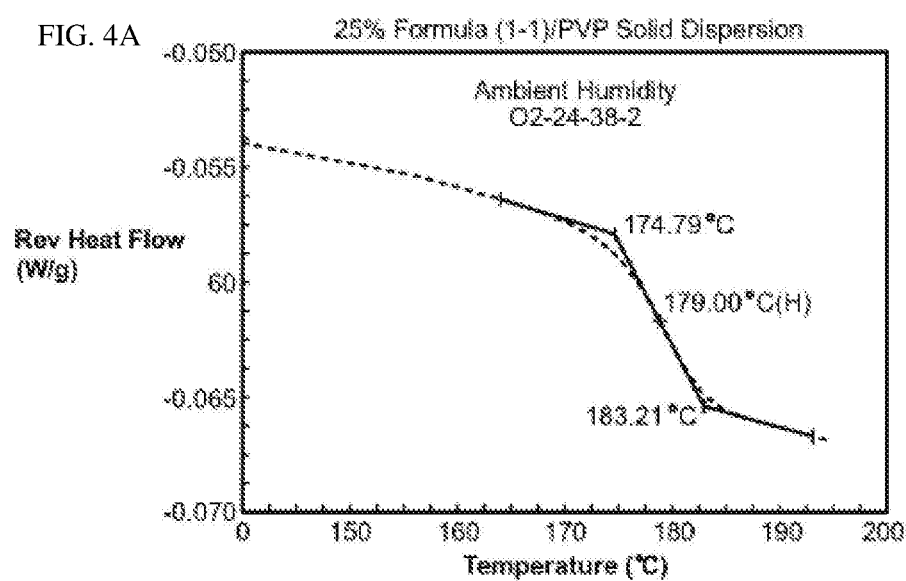
FIG. 4A illustrates modified differential scanning calorimetry trace for a solid dispersion of 25% compound (1-1) and PVP equilibrated under ambient conditions.
Figure 4B:
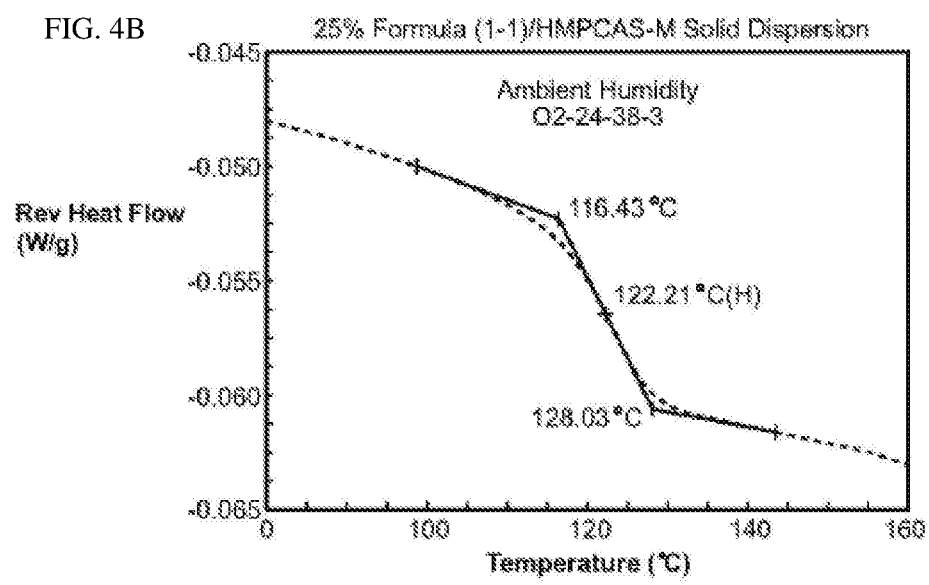
FIG. 4B illustrates modified differential scanning calorimetry trace for a solid dispersion of 25% compound (1-1) and HMPCAS-M equilibrated under ambient conditions.
Figure 4C:
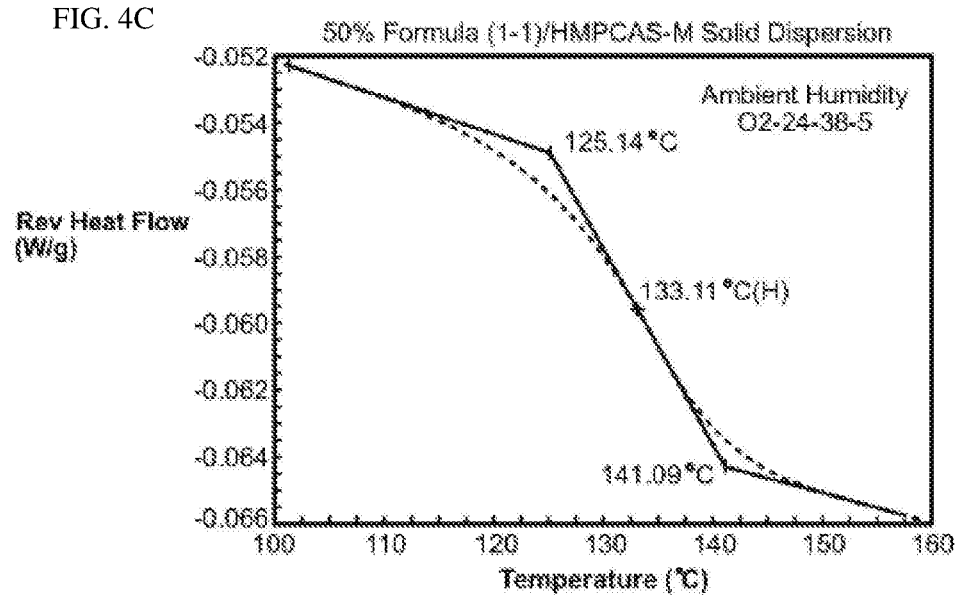
FIG. 4C illustrates modified differential scanning calorimetry trace for a solid dispersion of 50% compound (1-1) and HMPCAS-M equilibrated under ambient conditions.
Figure 5:
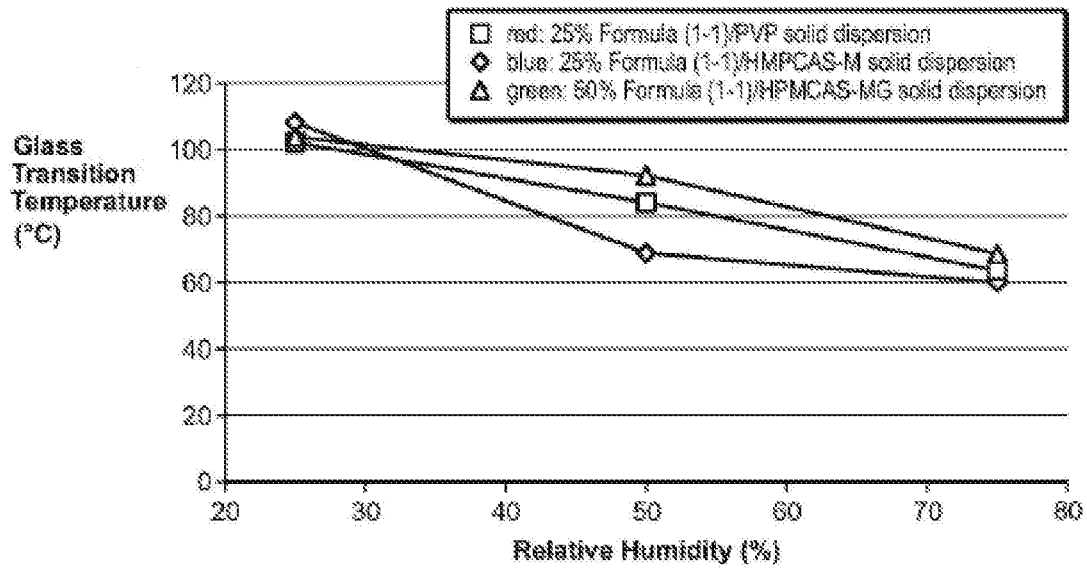
FIG. 5 illustrates plot of glass transition temperature (Tg) versus relative humidity (RH) for solid dispersions of 25% compound (1-1) and PVP or HMPCAS-M and 50% compound (1-1) and HPMCAS-MG.
Figure 6:
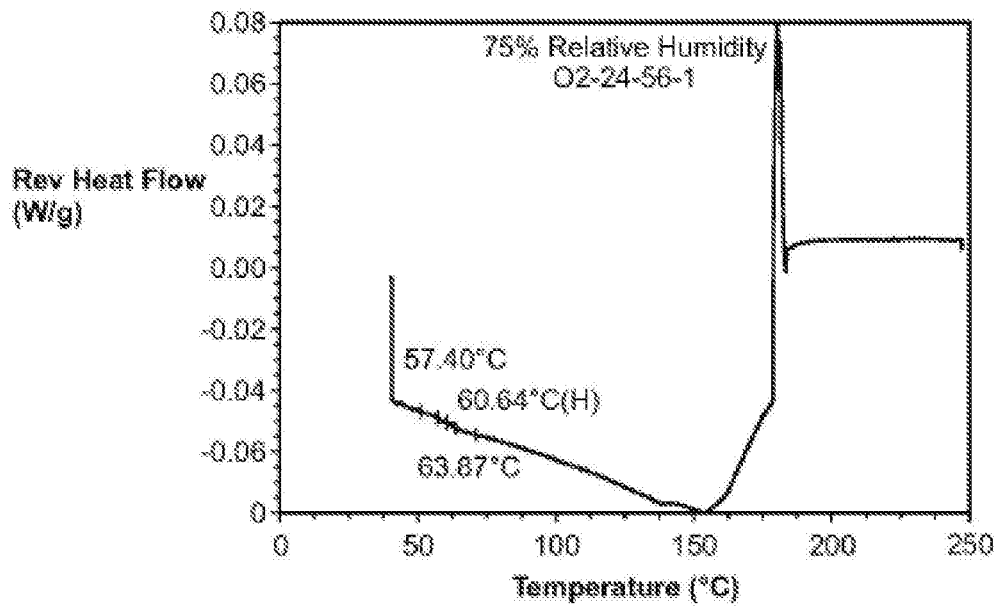
FIG. 6 illustrates modified differential scanning calorimetry trace for a solid dispersion of 25% compound (1-1) and PVP equilibrated under 75% relative humidity.

The non-sink dissolution results (FIGS. 2A-2C) were comparable to those found for the dispersions in Example 1. PXRD results (FIG. 3) showed no evidence of crystalline compound in any of the dispersions and mDSC results (FIGS. 4A-4C) showed a single glass transition temperature (Tg) for each dispersion, indicating that each dispersion was homogeneous. An inverse relationship between Tg and relative humidity was observed for each (FIG. 5). Notably, for the 25% compound (1-1) in PVP solid dispersion equilibrated at 75% RH, there appeared to be two Tgs, indicating that phase separation was occurring, and this dispersion also showed a melt event at 75% RH, suggesting that crystallization occurred during the RH equilibration (FIG. 6). This finding suggests that the 25% compound (1-1) in PVP dispersion may be less stable than the HPMCAS-M dispersions.

To assess the bioavailability of the three dispersions, groups of male beagle dogs (three per group) were given a 3 mg/kg dose of an aqueous suspension of solid dispersion of compound (1-1) administered by oral gavage or a 1 mg/kg dose of compound (1-1) dissolved in water:ethanol:polyethylene glycol (PEG) 400 (60:20:20) and administered as an intravenous bolus into the cephalic vein. Blood samples were collected from the jugular vein of each animal at 0 (pre-dose), 5, 15, and 30 minutes and 1, 2, 4, 8, 12, and 24 hours following intravenous administration and at 0 (pre-dose), 15 and 30 minutes and 1, 2, 4, 8, 12, and 24 hours following oral gavage administration. The amount of compound (1-1) present in each sample was detected using a qualified LC-MS/MS method with a lower limit of quantification of 0.5 ng/mL. The area under the plasma concentration-time curve (AUC) was determined by use of the linear trapezoidal rule up to the last measurable concentration without extrapolation of the terminal elimination phase to infinity. The elimination half-life ($t_{1/2}$) was calculated by least-squares regression analysis of the terminal linear part of the log concentration-ime curve. The maximum plasma concentration ($C_{max}$) and the time to $C_{max}$ ($t_{max}$) were derived directly from the plasma concentration data. The oral bioavailability (F) was calculated by dividing the dose normalized AUC after oral administration by the dose normalized AUC after intravenous administration and reported as percentages (%). Results, summarized in Table 1 below, gave mean oral bioavailabilities of the 25% compound (1-1) in PVP, 25% compound (1-1) in HPMCAS-M, and 50% compound (1-1) in HPMCAS-M solid dispersions of 58%, 49%, and 74%, respectively.

TABLE 1

Pharmacokinetic parameters of compound (1-1) after oral (po) and intravenous (iv) administrations to dogs (the values are averages from three dogs)

| Compound (1-1) formulation | Dose & Route | $C_{max}$ (ng/L) | $t_{max}$ (hr) | AUC (ng · min/mL) | $t_{1/2}$ (hr) | F (%) |
|---|---|---|---|---|---|---|
| Solution in water:ethanol:PEG400 (60:20:20) | 1 mg/kg IV | 769 | 0.083 | 53,312 | 1.5 | — |
| Aqueous suspension of 25% compound (1-1)/PVP solid dispersion | 3 mg/kg PO | 487 | 1.0 | 93,271 | 1.6 | 58 |
| Aqueous suspension of 25% compound (1-1)/HPMCAS-M solid dispersion | 3 mg/kg PO | 228 | 0.5 | 78,595 | 2.0 | 49 |
| Aqueous suspension of 50% compound (1-1)/HPMCAS-M solid dispersion | 3 mg/kg PO | 371 | 1.0 | 118,174 | 1.5 | 74 |

AUC: area under the plasma concentration-time curve;
$C_{max}$: maximum plasma concentration;
F: bioavailability;
HPMCAS: hypromellose acetate sodium;
IV: intravenous;
PEG: polyethylene glycon;
PO; per os, oral;
PVP: polyvinylpyrrolidone;
$t_{max}$: time of $C_{max}$;
$t_{1/2}$: plasma elimination half-life Example 3

Preparation and Clincial Use of Capsules Containing a Solid Dispersion of Compound (1-1)

A gelatin capsule of 10 mg strength was prepared for initial clinical studies in patients with hematologic malignancies. Based on results of in vitro and in vivo testing of solid dispersions of compound (1-1), as described in Examples 1 and 2, a 50% compound (1-1) in HPMCAS-M solid dispersion was selected for capsule development. Capsule development was initiated targeting a fill weight of 190 mg in a size 3 hard gelatin capsule, as this configuration would potentially allow increasing the capsule strength by filling a larger size capsule while maintaining the pharmaceutical composition. Based on experience, four capsule formulations were designed with different amounts of disintegrant and with and without wetting agent. Since all four formulations showed similar disintegration test and dissolution test results, the simplest formulation (without wetting agent and minimum disintegrant) was selected for manufacturing. Manufacturing process development and scale-up studies were performed to confirm the spray drying process and post-drying times for the solid dispersion; blending parameters; roller compaction and milling of the blend to achieve target bulk density of approximately 0.60 g/cc; and capsule filling conditions.

Crystalline compound (1-1) and the polymer hypromellose actate succinate (HPMCAS-M) were dissolved in acetone and spray-dried to produce solid dispersion intermediate (SDI) granules containing a 50% compound (1-1) loading. The SDI was shown by PXRD analysis to be amorphous and by mDSC analysis to be homogeneous (i.e., single Tg under ambient conditions). The 50% compound (1-1) in HPMCAS-M solid dispersion (1000 g) and excipients, including microcrystalline cellulose filler-binder (4428 g), croscarmellose sodium disintegrant (636 g), colloidal silicon dioxide dispersant/lubricant 156 g), magnesium stearate dispersant/lubricant (156 g), and lactose monohydrate filler (5364 g) were blended in stages in a V-blender. The blend was them compacted and granulated to obtain a bulk density of approximately 0.6 g/mL. The blend was dispensed into size 3 hard gelatin capsules (target fill weight: 190 mg) using an automated filling machine and finished capsules were polished using a capsule polisher machine.

Pharmacokinetic assessments were performed following oral dosing of 10 mg capsules containing the 50% compound (1-1) in HPMCAS solid dispersion and results were compared with pharmacokinetic assessments performed following oral dosing of administration of 4×10 mg capsules containing the Eudragit solid dispersion of compound (1-1) to healthy volunteers A comparison of the two pharmaceutical compositions is provided in Tables 2A and 2B below. The Eudragit formulation previously was described in Example 5 in US Patent Application 2009/0012064 A1, published Jan. 8, 2009. That application noted that the Eudragit solid dispersion formulation was made by dissolving and/or dispersing the thienotriazolodiazepine of formula (A) and coating excipients, including ammonio methacrylate copolymer type B (Eudragit RS), methacrylic acid copolymer type C (Eudragit L100-55), talc, and magnesium aluminosilicate, in a mixture of water and ethanol. This heterogeneous mixture then was applied to microcrystalline cellulose spheres (Nonpareil 101, Freund) using a centrifugal fluidizing bed granulator to produce granules that were dispensed into size 2 hydroxypropyl methylcellulose capsules.

In both clinical studies, blood levels of compound (1-1) were determined using validated LC-MS/MS methods and pharmacokinetic analyses were performed based on plasma concentrations of compound (1-1) measured at various time points over 24 hours after capsule administration. Results, summarized in Table 3 below, showed that the HPMCAS-M solid dispersion formulation had over 3-fold higher bioavailability in humans than the Eudragit solid dispersion formulation based on AUCs (924*4/1140, adjusting for difference in doses administered). Additionally, based on the observed $T_{max}$, the HPMCAS formulation is more rapidly absorbed than the Eudragit formulation ($T_{max}$ of 1 h vs 4-6 h). The marked improvement in systemic exposure with the HPMCAS-M solid dispersion formulation is unexpected.

TABLE 2A

Solid dispersion capsules of compound (1-1) for clinical use pharmaceutical composition containing 50% HPMCAS solid dispersion of compound (1-1): 10 mg strength, size 3 hard gelatin capsule

| Ingredient | Function | Capsule Content mg | Wt % |
|---|---|---|---|
| Compound of formula (II) | active agent | 10.0* | 5.56 |
| Hypromellose acetate succinate (HPMCAS-M) | carrier for solid dispersion | 10.0 | 5.56 |
| Lactose monohydrate | filler | 85.0 | 47.22 |
| Microcrystalline cellulose | filler-binder | 70.0 | 38.89 |
| Croscarmellose sodium | disintegrant | 10.0 | 5.56 |
| Collidal silicon dioxide | dispersant/lubricant | 2.5 | 1.39 |
| Magnesium stearate | dispersant/lubricant | | |
| Total | | 190.0 | 100.0 |

TABLE 2B

Pharmaceutical composition containing Eudragit L100-55 solid dispersion of compound (1-1): 10 mg strength, size 2 hard gelatin capsule

| Ingredient | Function | Capsule Content mg | Wt % |
|---|---|---|---|
| Compound (1-1) | active agent | 10.0* | 3.8 |
| Core: | | | |
| Microcrystalline cellulose spheres (Nonpareil 101, Freund, Inc) | vehicle | 100.0 | 38.5 |
| Compound/polymer layer: | | | |
| Ammonio methacrylate copolymer, type B (NF. PhEur) (Edragit RS, Evonik) | coating agent | 10.8 | 4.2 |
| Methacrylic acid copolymer, type C (NF)/Methacrylic acid-ethyl acrylate copolymer (1:1) type A (PhEur) (Eudragit L100-55, Evonik) | coating agent | 25.2 | 9.7 |
| Talc | coating agent | 88.2 | 33.9 |
| Magnesium aluminometasilicate (Neuslin, Fuji Chemical) | coating agent | 20.0 | 7.7 |
| Triethyl citrate | plasticizer | 5.0 | 1.9 |
| Silicon dioxide | fluidizing agent | 0.8 | 0.3 |
| | | 260.0 | 100.0 |

*as anhydrate

TABLE 3

Pharmacokinetic parameters following oral administration of solid dispersions of compound (1-1) to humans

| Compound (1-1) formulation | # Patients | Dose and Route | $C_{max}$ (ng/mL) | $T_{max}$ (hr) | $AUC_{0-24\,h}$ (ng · h/mL) |
|---|---|---|---|---|---|
| Eudragit solid dispersion formulation | 7 | 40 mg PO | 83 | 4 to 6 | 1140 |
| 50% HMPCAS-M solid dispersion formulation | 7 | 10 mg PO | 286 | 1 | 925 |

$AUC_{0-24\,h}$: area under the compound (1-1) plasma concentration vs. time curve over 24 hours
$C_{max}$: maximum concentration in plasma
hr: hour
HPMCAS: hypromellose acetate succinate
mL: milliliter
ng: nanogram
PO: per os, oral
$T_{max}$: time of $C_{max}$ Example 4

Oral Exposure in the Rat

The oral bioavailability of three formulations of solid dispersions of compound (1-1) was determined in rats. The three dispersions chosen were the 25% dispersion of compound (1-1) in PVP, the 25% dispersion of compound (1-1) in HPMCAS-MG, and the 50% dispersion of compound (1-1) in HPMCAS-MG. The animals used in the study were Specific Pathogen Free (SPF) Hsd:Sprague Dawley rats obtained from the Central Animal Laboratory at the University of Turku, Finland. The rats were originally purchased from Harlan, The Netherlands. The rats were female and were ten weeks of age, and 12 rats were used in the study. The animals were housed in polycarbonate Makrolon II cages (three animals per cage), the animal room temperature was 21+/−3° C., the animal room relative humidity was 55+/−15%, and the animal room lighting was artificial and was cycled for 12 hour light and dark periods (with the dark period between 18:00 and 06:00 hours). Aspen chips (Tapvei Oy, Estonia) were used for bedding, and bedding was changed at least once per week. Food and water was provided prior to dosing the animals but was removed during the first two hours after dosing.

The oral dosing solutions containing the 25% dispersion of compound (1-1) in PVP, the 25% dispersion of compound (1-1) in HPMCAS-MG, and the 50% dispersion of compound (1-1) in HPMCAS-MG were prepared by adding a pre-calculated amount of sterile water for injection to containers holding the dispersion using appropriate quantities to obtain a concentration of 0.75 mg/mL of compound (1-1). The oral dosing solutions were subjected to vortex mixing for 20 seconds prior to each dose. The dosing solution for intravenous administration contained 0.25 mg/mL of compound (1-1) and was prepared by dissolving 5 mg of compound (1-1) in a mixture containing 4 mL of polyethylene glycol with an average molecular weight of 400 Da (PEG400), 4 mL of ethanol (96% purity), and 12 mL of sterile water for injection. The dosing solution containing the 25% dispersion of compound (1-1) in PVP was used within 30 minutes after the addition of water. The dosing solutions containing the 25% dispersion of compound (1-1) in HPMCAS-MG and the 50% dispersion of compound (1-1) in HPMCAS-MG were used within 60 minutes of after the addition of water. A dosing volume of 4 mL/kg was used to give dose levels of compound (1-1) of 1 mg/kg for intravenous administration and 3 mg/kg for oral administration. The dosing scheme is given in Table 4.

TABLE 4

Dosing scheme for rat oral exposure study.

| Rat | Weight | Dose (mL) | Test Item | Route |
|---|---|---|---|---|
| 1 | 236.5 | 0.95 | Compound (1-1) | intravenous |
| 2 | 221 | 0.88 | Compound (1-1) | intravenous |
| 3 | 237.5 | 0.95 | Compound (1-1) | intravenous |
| 4 | 255.5 | 1.02 | 25% dispersion of compound (1-1) in PVP | oral |
| 5 | 224.2 | 0.90 | 25% dispersion of compound (1-1) in PVP | oral |
| 6 | 219.2 | 0.88 | 25% dispersion of compound (1-1) in PVP | oral |
| 7 | 251.6 | 1.01 | 25% dispersion of compound (1-1) in HPMCAS-MG | oral |
| 8 | 240.4 | 0.96 | 25% dispersion of compound (1-1) in HPMCAS-MG | oral |
| 9 | 238 | 0.95 | 25% dispersion of compound (1-1) in HPMCAS-MG | oral |
| 10 | 226.6 | 0.91 | 50% dispersion of compound (1-1) in HPMCAS-MG | oral |
| 11 | 228.4 | 0.91 | 50% dispersion of compound (1-1) in HPMCAS-MG | oral |
| 12 | 228.5 | 0.91 | 50% dispersion of compound (1-1) in HPMCAS-MG | oral |

Blood samples of approximately 50 µL were collected into Eppendorf tubes containing 5 µL of ethylenediaminetetraacetic acid (EDTA) solution at time points of 0.25, 0.5, 1, 2, 4, 8, 12, and 24 hours after dosing, with each sample collected within a window of 5 minutes from the prescribed time point. From each sample, 20 µL of plasma was obtained and stored at dry ice temperatures for analysis. Analysis of each sample for the concentration of compound (1-1) was performed using a validated liquid chromatography tandem mass spectrometry (LC-MS/MS) method with a lower limit of quantitation of 0.5 ng/mL.

Pharmacokinetic parameters were calculated with the Phoenix WinNonlin software package (version 6.2.1, Pharsight Corp., CA, USA) with standard noncompartmental methods. The elimination phase half-life ($t_{1/2}$) was calculated by least-squares regression analysis of the terminal linear part of the log concentration-time curve. The area under the plasma concentration-time curve (AUC) was determined by use of the linear trapezoidal rule up to the last measurable concentration and thereafter by extrapolation of the terminal elimination phase to infinity. The mean residence time (MRT), representing the average amount of time a compound remains in a compartment or system, was calculated by extrapolating the drug concentration profile to infinity. The maximum plasma concentration ($C_{max}$) and the time to $C_{max}$ ($t_{max}$) were derived directly from the plasma concentration data. The tentative oral bioavailability (F) was calculated by dividing the dose normalised AUC after oral administration by the dose normalised AUC after intravenous administration, i.e. F=(AUC(oral)/Dose(oral))/(AUC(intravenous)/Dose(intravenous))] and is reported as percentage (%).

Figure 7:
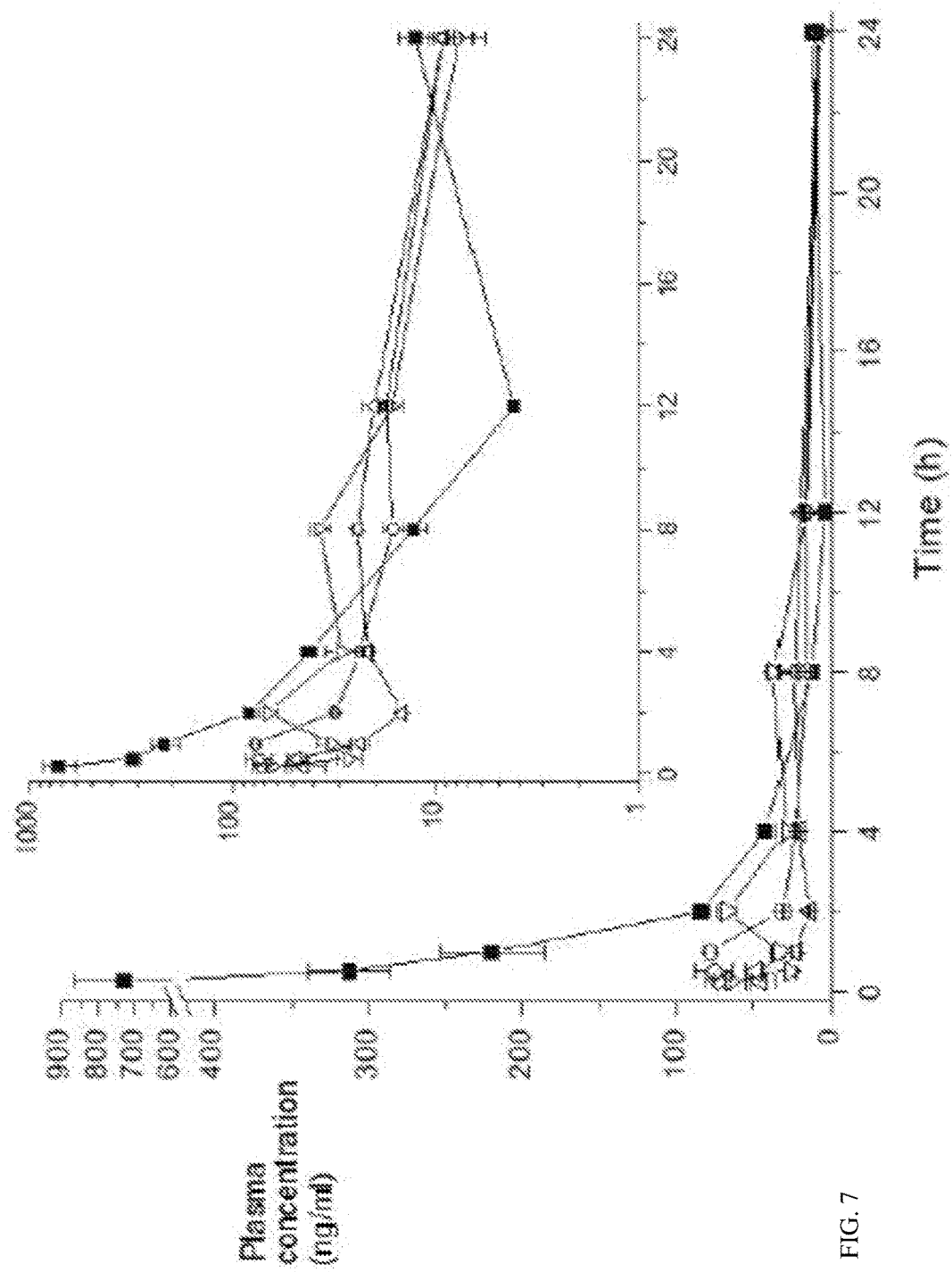
FIG. 7 illustrates plasma concentration versus time curves for Compound (1-1) after 1 mg/kg intravenous dosing (solid rectangles) and 3 mg/kg oral dosing as 25% Compound (1-1):PVP (open circles), 25% Compound (1-1):HPMCAS-MG (open triangles), and 50% Compound (1-1):HPMCAS-MG (open inverted triangles). The inset depicts the same data plotted on a semilogarithmic scale.
Figure 8:
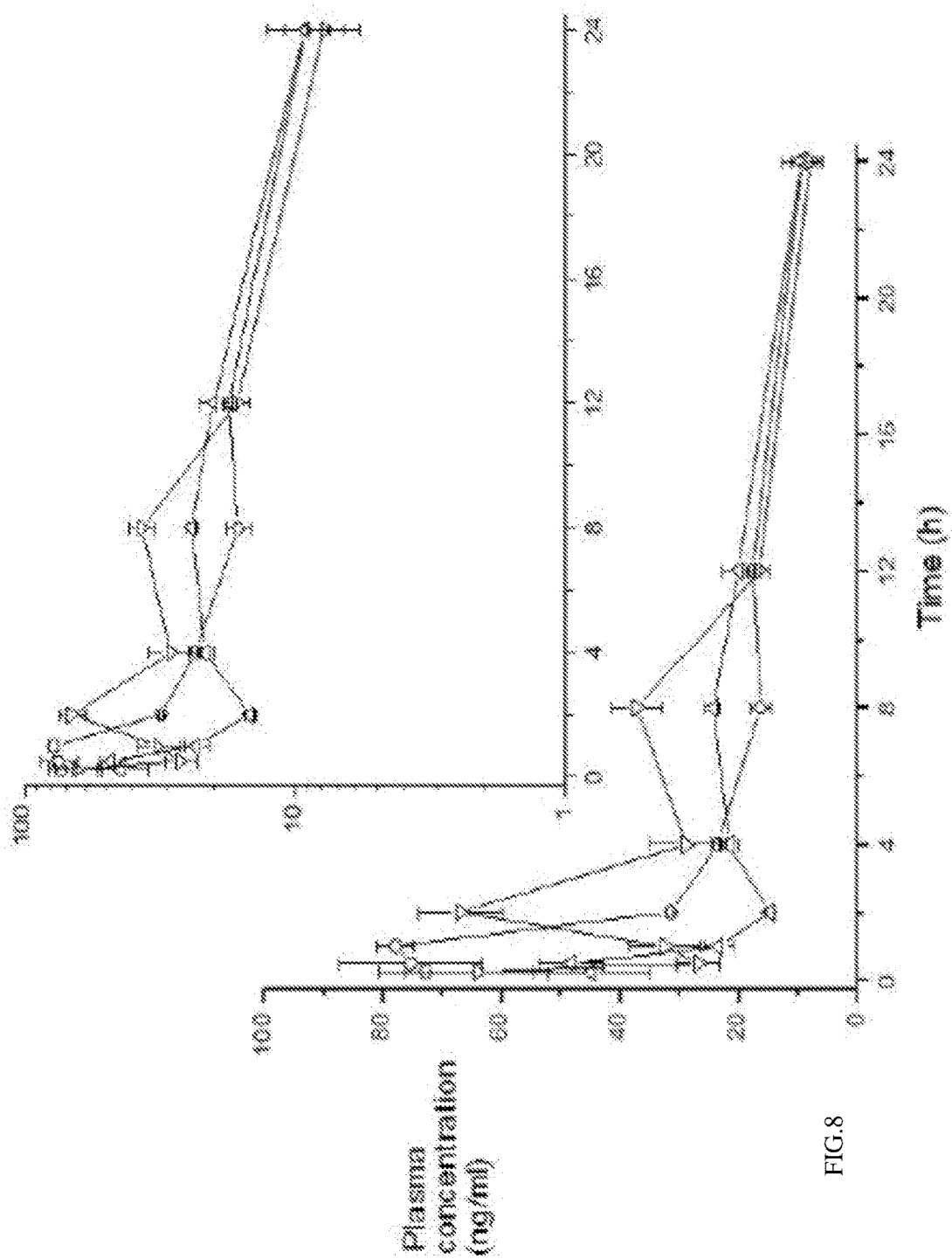
FIG. 8 illustrates plasma concentration versus time curves for Compound (1-1) after 3 mg/kg oral dosing as 25% Compound (1-1):PVP (open circles), 25% Compound (1-1):HPMCAS-MG (open triangles), and 50% Compound (1-1):HPMCAS-MG (open inverted triangles). The inset depicts the same data plotted on a semi-logarithmic scale.

The pharmacokinetic parameters are given in Table 5, and the plasma concentration versus time plots are shown in FIGS. 7 and 8.

TABLE 5

Pharmacokinetic parameters of compound (1-1) after oral and intravenous administrations. The values are an average from three animals.

| Compound | Parameter | 1 mg/kg intravenous | 3 mg/kg oral | F(%) |
|---|---|---|---|---|
| Compound (1-1) water:ethanol:PEG 400 (60:20:20) | AUC (min*ng/ml) | 74698 | | |
| | $C_{max}$ (ng/ml) | 730 | | |
| | $T_{max}$ (hr) | 0.25 | | |
| | $t_{1/2}$ (hr) 8.5 | 8.5 | | |
| | Cl/F (ml/min/kg) | 13.4 | | |
| | MRT (hr) | 7.4 | | |
| 25% dispersion of compound (1-1) in PVP | AUC (min*ng/ml) | | 39920 | 18 |
| | $C_{max}$ (ng/ml) | | 77.9 | |
| | $T_{max}$ (hr) | | 1 | |
| | $t_{1/2}$ (hr) 8.5 | | 13.8 | |
| | Cl/F (ml/min/kg) | | 75.2 | |
| | MRT (hr) | | 18.0 | |
| 25% dispersion of compound (1-1) in HPMCAS-MG | AUC (min*ng/ml) | | 35306 | 16 |
| | $C_{max}$ (ng/ml) | | 48.3 | |
| | $T_{max}$ (hr) | | 0.5 | |
| | $t_{1/2}$ (hr) 8.5 | | 11.0 | |
| | Cl/F (ml/min/kg) | | 85.0 | |
| | MRT (hr) | | 17.1 | |
| 50% dispersion of compound (1-1) in HPMCAS-MG | AUC (min*ng/ml) | | 40238 | 18 |
| | $C_{max}$ (ng/ml) | | 67.0 | |
| | $T_{max}$ (hr) | | 2 | |
| | $t_{1/2}$ (hr) 8.5 | | 9.5 | |
| | Cl/F (ml/min/kg) | | 74.6 | |
| | MRT (hr) | | 12.8 | |

Example 5

Preparation of Spray Dried Dispersions

Spray dried dispersions of compound (1-1) were prepared using five selected polymers: HPMCAS-MG (Shin Etsu Chemical Co., Ltd.), HPMCP-HP55 (Shin Etsu Chemical Co., Ltd.), PVP (ISP, a division of Ashland, Inc.), PVP-VA (BASF Corp.), and Eudragit L100-55 (Evonik Industries AG). All spray dried solutions were prepared at 25% and 50% by weight with each polymer. All solutions were prepared in acetone, with the exception of the PVP solutions, which were prepared in ethanol. For each solution, 1.0 g of solids (polymer and compound (1-1)) were prepared in 10 g of solvent. The solutions were spray dried using a Büchi B-290, PE-024 spray dryer with a 1.5 mm nozzle and a Büchi B-295, P-002 condenser. The spray dryer nozzle pressure was set to 80 psi, the target outlet temperature was set to 40° C., the chiller temperature was set to −20° C., the pump speed was set to 100%, and the aspirator setting was 100%. After spray drying, the solid dispersions were collected and dried overnight in a low temperature convection oven to remove residual solvents.

Example 6

Stability with Humidity and Temperature

TABLE 6

| Test | Procedure | Acceptance Criteria | T = 0 (Initial) | T = 1 month (storage at 40° C./75% RH) | T = 2 month (storage at 40° C./75% RH) | T = 3 month (storage at 40° C./75% RH) |
|---|---|---|---|---|---|---|
| Appearance | AM-0002 | White to off-white powder | Test Date/Ref: 06Aug2012/02-41-2 White Powder | Test Date/Ref: 24Sep2012/02-41-59 White Powder | Test Date/Ref: 24Oct2012/02-37-106 White Powder | Test Date/Ref: 17Dec2012/02-37-119 White Powder |

TABLE 6-continued

Figure 9:
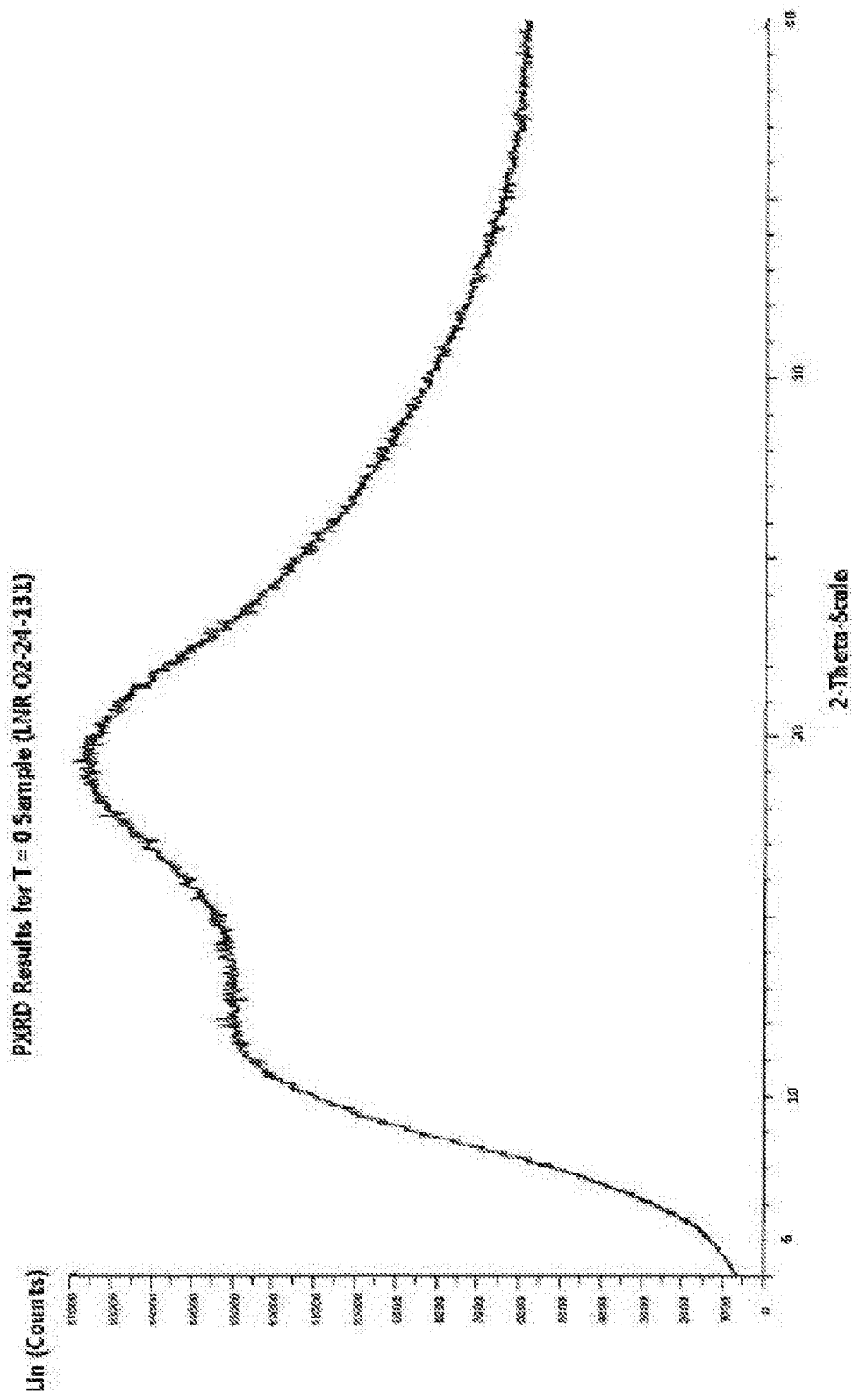
FIG. 9 illustrates a powder X-ray diffraction profile of solid dispersions of compound (1-1) in HPMCAS-MG at time zero of a stability test.
Figure 10:
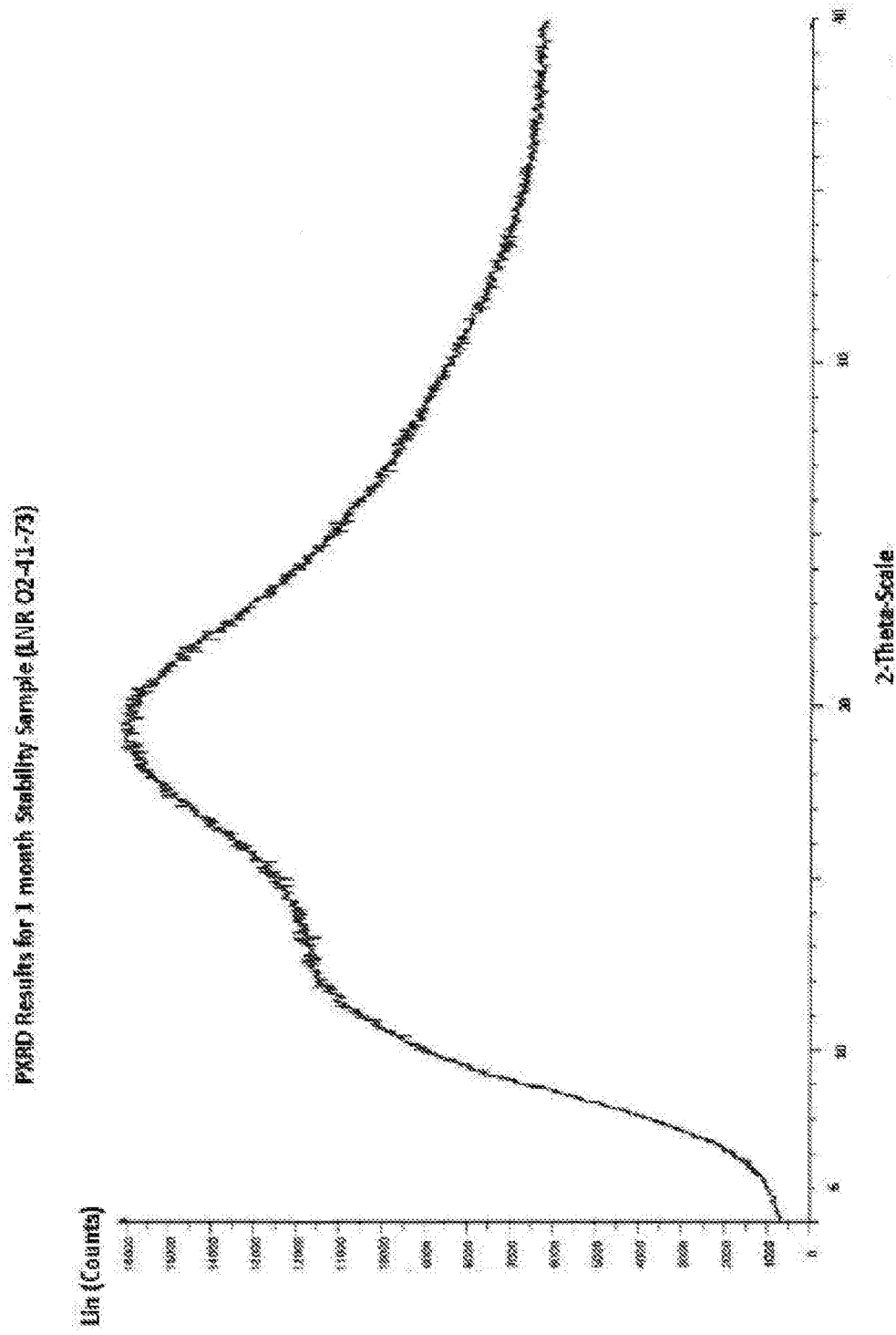
FIG. 10 illustrates a powder X-ray diffraction profile of solid dispersions of compound (1-1) in HPMCAS-MG after 1 month at 40° C. and 75% relative humidity.
Figure 11:
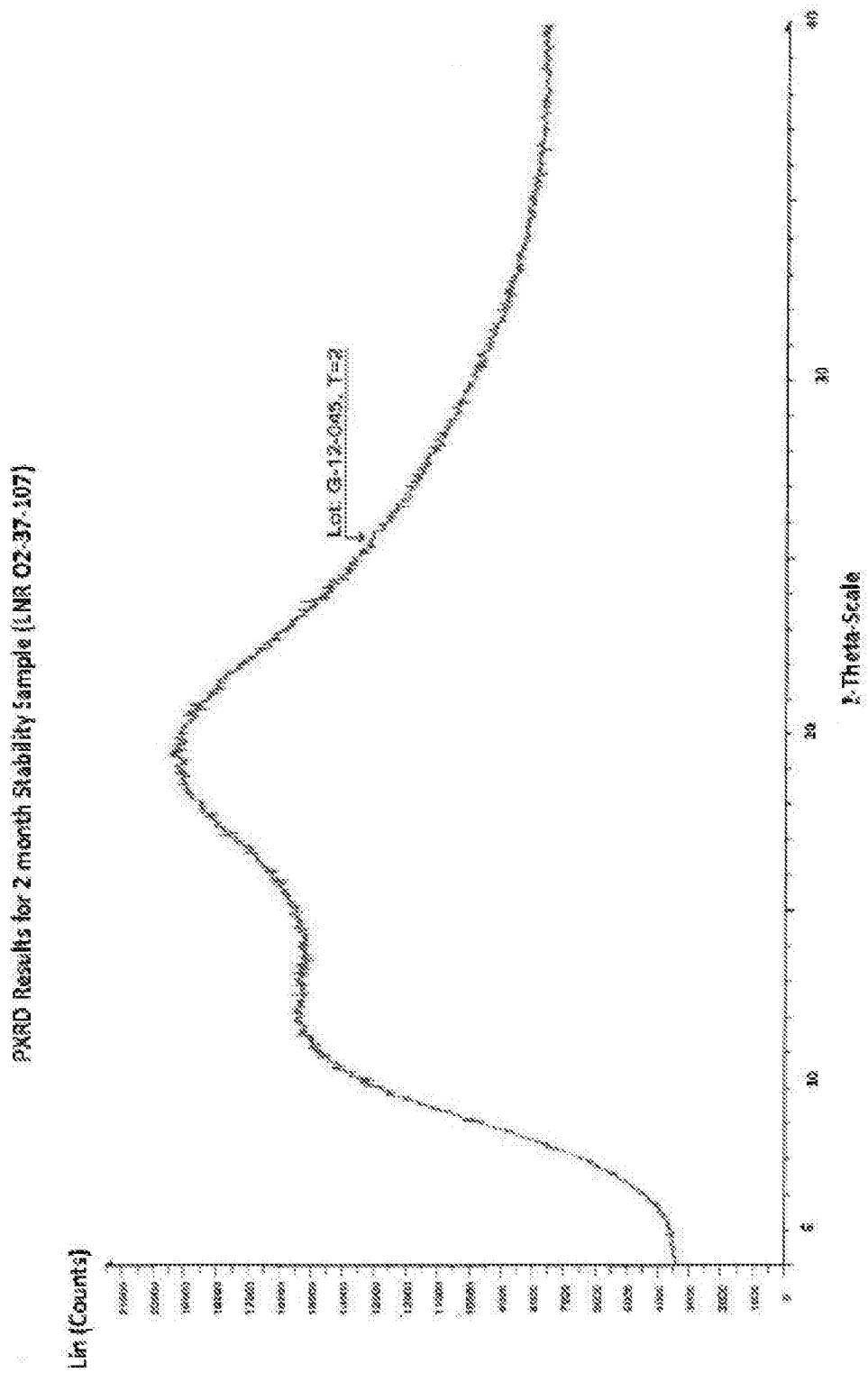
FIG. 11 illustrates a powder X-ray diffraction profile of solid dispersions of compound (1-1) in HPMCAS-MG after 2 months at 40° C. and 75% relative humidity.
Figure 12:
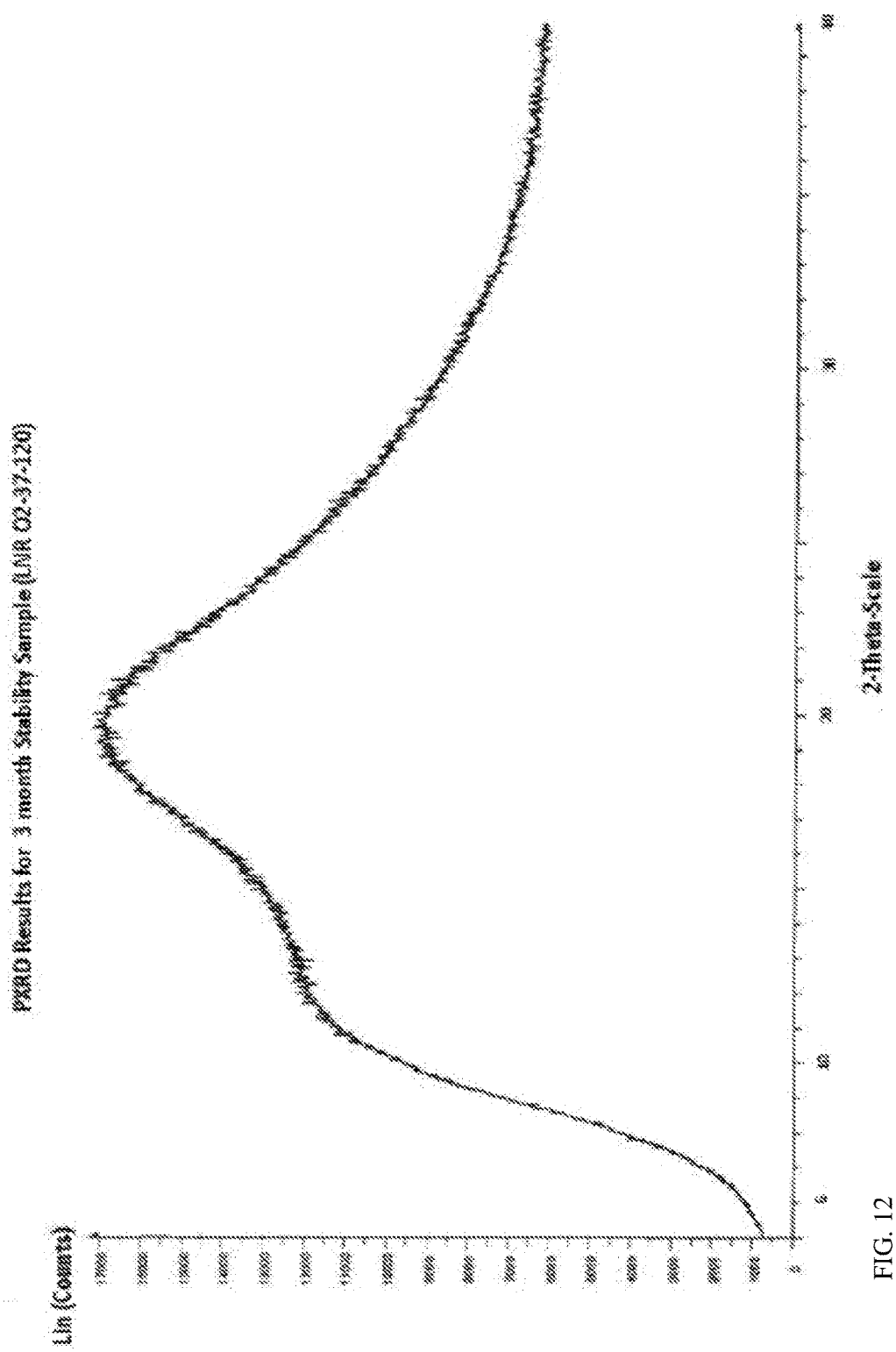
FIG. 12 illustrates a powder X-ray diffraction profile of solid dispersions of compound (1-1) in HPMCAS-MG after 3 months at 40° C. and 75% relative humidity.

| Test | Procedure | Acceptance Criteria | T = 0 (Initial) | T = 1 month (storage at 40° C./75% RH) | T = 2 month (storage at 40° C./75% RH) | T = 3 month (storage at 40° C./75% RH) |
| --- | --- | --- | --- | --- | --- | --- |
| Potency (HPLC) | AM-0028 | 45.0 - 55.0 wt % | Test Date/Ref: 25Jul2012/02-37-21 50.0 | Test Date/Ref: 25Sep2012/02-4H10 49.4 | Test Date/Ref: 24Oct2012/02-37-105 49.8 | Test Date/Ref: 29Nov2012/02-34-107 49.2 |
| Individual Related Substances (HPLC) | AM-0029 | Report resets | Test Date/Ref: 25Jul2012/02-34-49 RRT    % Area No reportable related substances | Test Date/Ref: 26Sep2012/02-41-64 RRT    % Area No reportable related substances | Test Date/Ref: 24Oct2012/02-37-105 RRT    % Area 0.68    0.06 0.77    0.06 | Test Date/Ref: 29Nov2012/02-34-107 RRT    % Area 0.68    0.07 0.77    0.09 |
| Total Related Substances (HPLC) | AM-0029 | Report result | Test Date/Ref: 25Jul2012/02-34-49 No reportable related substances | Test Date/Ref: 26Sep2012/02-41-64 No reportable related substances | Test Date/Ref: 24Oct2012/02-37-105 0.12% | Test Date/Ref: 29Nov2012/02-34-107 0.16% |
| Water Content (KF) | AM-0030 USP <921> | Report results (wt %) | Test Date/Ref: 02Aug2012/02-41-1 1.52 | Test Date/Ref: 27Sep2012/02-37-99 2.53 | Test Date/Ref: 25Oct2012102-37-110 2.70 | Test Date/Ref: 29Nov2012/02-37-116 3.43 |
| X-Ray Powder Diffraction (XRPD) | US <941> | Consistent with an amorphous form | Test Date/Ref: 24Jul2012/02-24-131 Consistent with an amorphous form See FIG. 9 | Test Date/Ref: 01Oct2012/02-41-73 Consistent with an amorphous form See FIG. 10 | Test Date/Ref: 24Oct2012/02-37-107 Consistent with an amorphous form See FIG. 11 | Test Date/Ref: 17Dec2012/02-37-120 Consistent with an amorphous form See FIG. 12 |
| Modulated Differential Scanning Calorimetry (mDSC) | USP <891> (n = 2 replicates) | Report individual and average glass transition temperatures (Tg, ° C.) | Test Date/Ref: 24Jul2012/02-24-130 Replicate 1 = 134.30° C., Replicate 2 = 134.23° C., Replicate 3 = 135.28° C., Average = 134.60° C. | Test Date/Ref: 26Sep2012/02-37-98 Replicate 1 = 134.65° C., Replicate 2 = 134.43° C., Average = 134.54° C. | Test Date/Ref: 24Oct2012/02-37-108 Replicate 1 = 135.35° C., Replicate 2 = 134.93° C., Average = 135.14° C. | Test Date/Ref: 17Dec2012/02-37-121 Replicate 1 = 134.36° C., Replicate 2 = 137.16° C., Average = 135.76° C. |

Spray dried dispersions of compound (1-1) in HPMCAS-MG were assessed for stability by exposure to moisture at elevated temperature. The glass transition temperature (Tg) as a function of relative humidity was determined at 75% relative humidity, 40° C. for 1, 2 and 3 months. The spray dried dispersion was stored in an LDPE bag inside a HDPE bottle to simulate bulk product packaging. The results are summarized in Table 6. At time zero, the Tg was 134° C., at 1 month the Tg was 134° C., at 2 months the Tg was 135° C. and at 3 months the Tg was 134° C. and only a single inflection point was observed for each measurement. X-ray diffraction patterns were also obtained for each sample. FIG. 9 illustrates a powder X-ray diffraction profile of solid dispersions of compound (1-1) in HPMCAS-MG at time zero of a stability test. FIGS. 10, 11, and 12 illustrate a powder X-ray diffraction profile of solid dispersions of compound (1-1) in HPMCAS-MG after 1-, 2-, and 3-months, respectively, at 40° C. and 75% relative humidity. The patterns did not show any diffraction lines associated with compound (1-1).

Example 7

In Vitro Treatment of NSCLC Cell Lines

Five established NSCLC cell lines (i.e. H2228, H3122, A549, HOP62 and HOP92) were exposed to increasing doses of compound (1-1) (OncoEthix SA, Switzerland). Effect on cell viability was determined by the MTT assay after 72 h exposure. The growth inhibition (GI) 50% values were determined by GraphPad Prism 5.0 software. And protein levels were analyzed by Western Blot using commercial antibodies. RNA was extracted with the Qiagen RNAEasy kit and reverse-transcribed using the Superscript First-Strand Synthesis System for RT-PCR kit following manufacturer's instructions. RT-PCR was performed using Fast SYBR Green Master Mix on a StepOnePlus Real-Time PCR System.

Compound (1-1) displayed anti-proliferative effects in both EML4-ALK-positive NSCLC cells after 72-h exposure with GI50 values of 629 and 627 nM in H2228 and H3122 cells, respectively. Interestingly, compound (1-1) was active in the EML4-ALK-negative (A549) cell line with GI50 of 432 nM. The expression of BRD4/3/2, c-MYC, BCL-2, p21 and CyclinD1 was characterized at the protein and mRNA levels in all cell lines. Both compound (1-1)-sensitive and -resistant lines exhibited similar basal expression levels for the aforementioned proteins. EML4-ALK variants 1 and 3 were identified in H3122 and H2228 cells, respectively. Cell signaling pathways assessment of the anti-proliferative activity showed that compound (1-1) induced a transient upregulation of STAT3 with a subsequent down-regulation after 24 h and up to 72 h exposure, this pathway being the key downstream effector of ALK frequently up-regulated in the crizotinib resistant cell lines. Interestingly, C-MYC protein and mRNA levels appeared not altered by compound (1-1). The EML4-ALK-positive H3122 cells showed down-regulation ofN-MYC mRNA levels after compound (1-1) treatment.

These results indicate that NSCLC cell lines with genomic ALK alterations are sensitive to BET-BRD inhibition by compound (1-1), with evident anti-proliferative effects seen alongside inhibition of downstream signaling pathways suggesting its clinical development as anticancer agents in ALK positive NSCLC patients.

Example 8

In Vitro Treatment of NSCLC Cell Lines

Compound (1-1) growth inhibition 50% (GI50) values were determined with MTT assay after 72-h exposure in 5 established NSCLC cell lines (H2228, H3122, A549, HOP62, HOP92). Protein levels were analyzed by Western Blot with commercial antibodies; RT-PCR was done with Fast SYBR Green Master Mix on a StepOnePlus Real-Time PCR System at baseline, 4 and 24 h post-treatment. For cell cycle analysis cells were stained with propidium iodide and DNA content analyzed with a FACScan flow cytometer. Compound (1-1) was combined with the targeted agents everolimus and crizotinib and the combination index (CI) determined by the Chou-Talalay method.

Compound (1-1) had antiproliferative effects in 4 of 5 NSCLC cell lines (two harboring the fusion protein EML4-ALK+) with GI50 values from 110 to 940 nM. In A549 cells, concurrent mutations in KRAS and LKB1 genes abrogate OTX015 effects, as described for JQ1, an compound (1-1) analog, while HOP92 and HOP62 are LKB1 wild-type. Percent cells in the S phase were reduced by 40%, 42% and 52% in HOP92, H2226 and H3122, respectively after 24 h exposure at 500 nM. Compound (1-1) combined with the ALK+-inhibitor crizotinib had additive effects (CI=0.98) after 48 h concomitant exposure in H2228 cells and additive/synergistic effects with everolimus in HOP62, HOP92, A549 and H2228. Compound (1-1)-sensitive and -resistant lines had similar basal mRNA and protein expression of BRD2/3/4, HEXIM BCL-2 and P21, CMYC and NMYC were overexpressed in HOP92 and H3122, respectively. Following 24 h compound (1-1) (500 nM), CMYC protein and mRNA were downregulated in HOP92 cells and NMYC downregulated in H3122 and HOP62 cells, while HEXIM mRNA was upregulated in compound (1-1)-sensitive cell lines.

NSCLC cell lines are sensitive to compound (1-1) BET inhibition, downregulating MYC family members and upregulating HEXIM, including NSCLC cells with the EML4-ALK fusion gene or KRAS mutation, suggesting its therapeutic potential in NSCLC.

Example 9

NSCLC with Oncogenic Mutations

Materials and Methods. Five established NSCLC cell lines, HOP62, HOP92, A549, H2228, and H3122 harboring different oncogenic mutations for KRAS, LKB I, TP53 and ALK (FIG. 13) were exposed to increasing doses of compound (1-1) (OncoEthix SA, Switzerland) for 72 h and cell proliferation was evaluated by MTT assays. Results represent the mean±95% CI of at least 3 independent experiments performed in triplicate. Protein levels were analyzed by Western blot using commercial antibodies. For cell cycle analysis cells were stained with PI and analyzed using a FACScan flow cytometer after 24 h of treatment. RT-PCR was performed using Fast SYBR Green Master Mix on a StepOnePlus Real-Time PCR System. Results represent the mean±SD of at least 2 5 independent experiments, where *p<0.05 versus control cells (0.1% DMSO), employing Anova followed by Dunnett's Multiple Comparison Test. Concomitant compound (1-1) combination studies were performed in cell lines exposed for 48 h to increasing doses of compound (1-1) alone or in combination with everolimus or crizotinib, and assessed using the Chou & Talalay method. Combination Index (CI) was determined by median effect plot analysis using CalcuSyn software. CI<1 synergy, CI=1 additivity and CI>1 antagonist effects. Results represent the median and range of 3 independent experiments performed in triplicate.

In vivo studies: $5\times10^6$ H3122 cells were injected in the flank of male athymic NMRI nude mice, and mice were randomized to 3 groups (8 mice/group) when tumor volume reach 100 mm³; vehicle (PBS, once daily, oral continuous), Compound (1-1) (50 mg/kg/bidaily, gavage, continuous), or crizotinib (25 mg/kg/daily, gavage, continuous).

Figure 14:
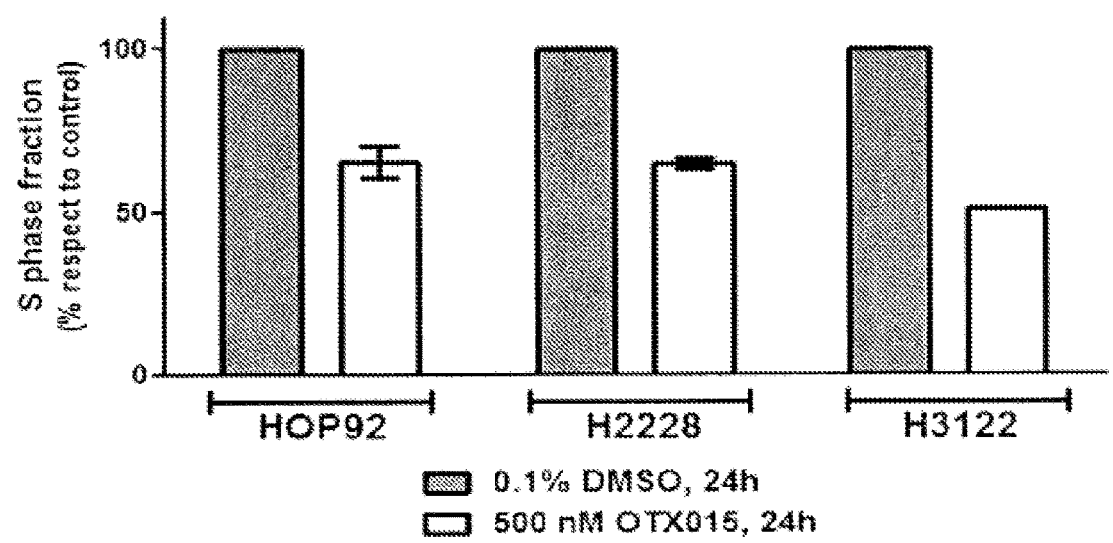
FIG. 14 illustrates the reduction of the S phase cell fraction after 24 h exposure to compound (1-1)
Figure 15A:
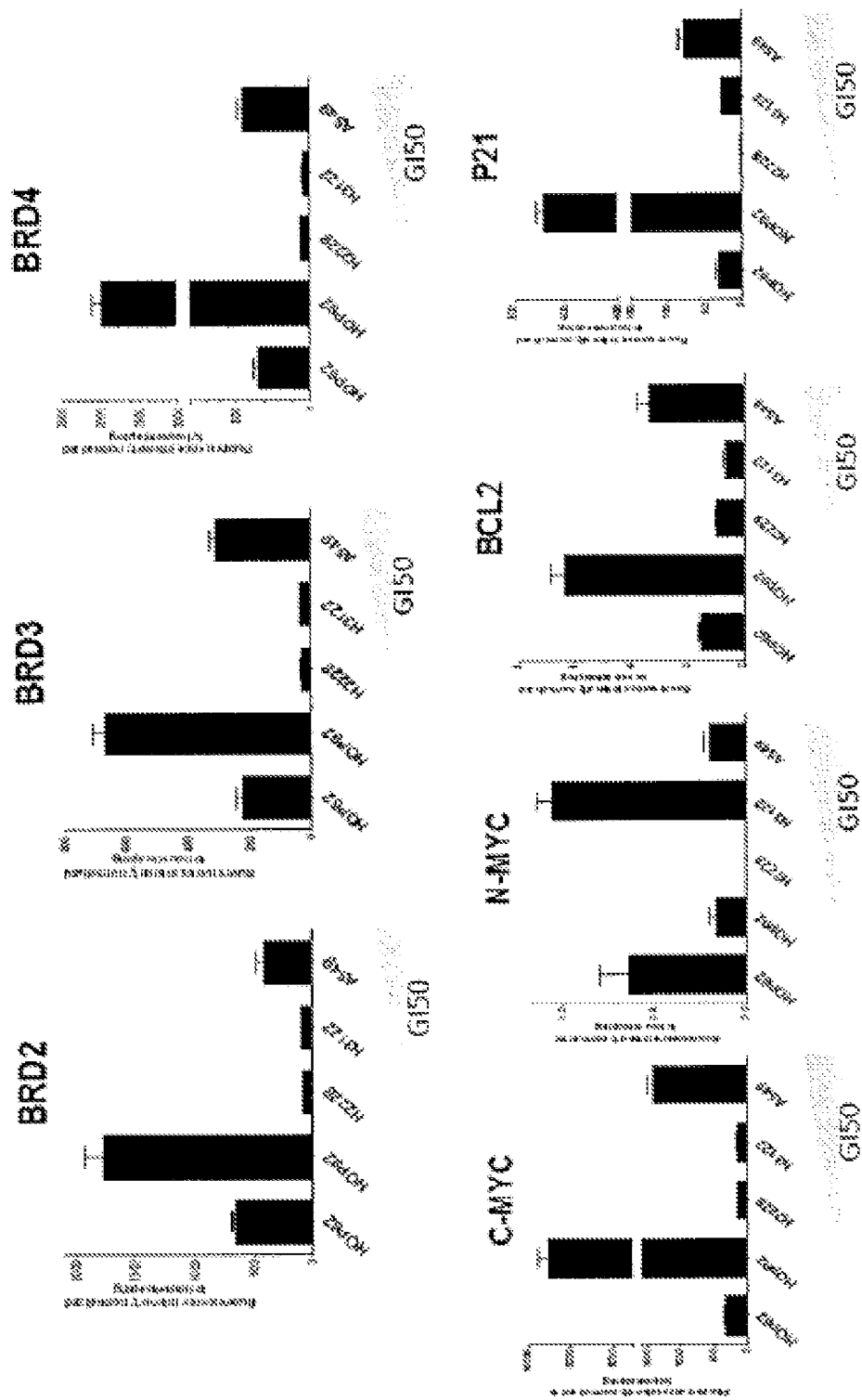
FIG. 15A illustrates BRDs, C-MYC, N-MYC, BCL2 and P21 mRNA levels in NSCLC cells classified in order of compound (1-1) sensitivity ($GI_{50}$ values)
Figure 15B:
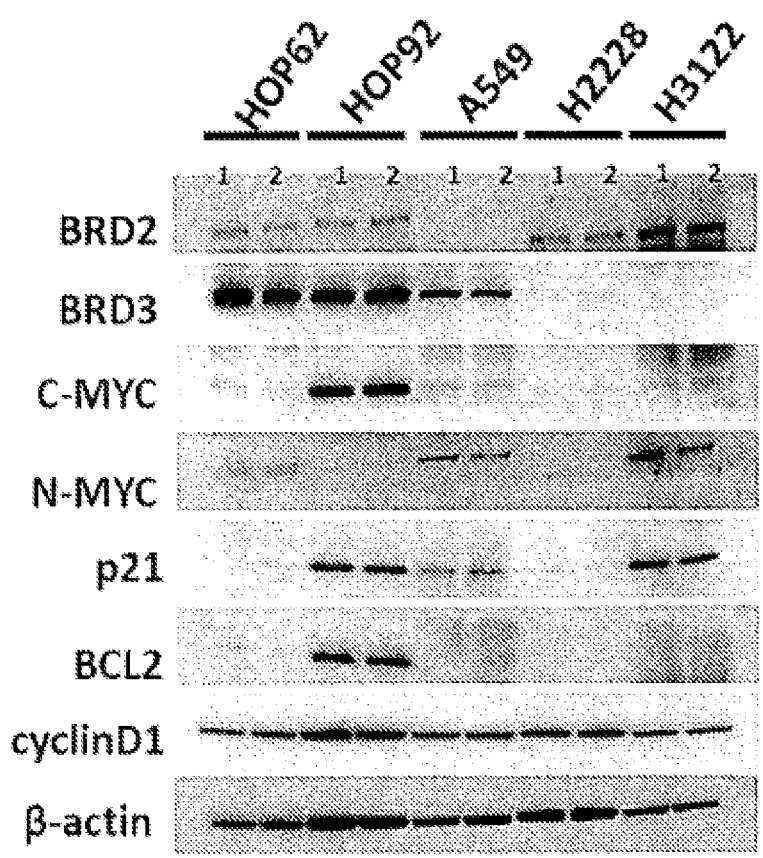
FIG. 15B illustrates basal protein expression of BRD2, BRD3, C-MYC, N-MYC, P21, BCL2 and cyclin D1 in NSCLC cells.
Figure 16A:
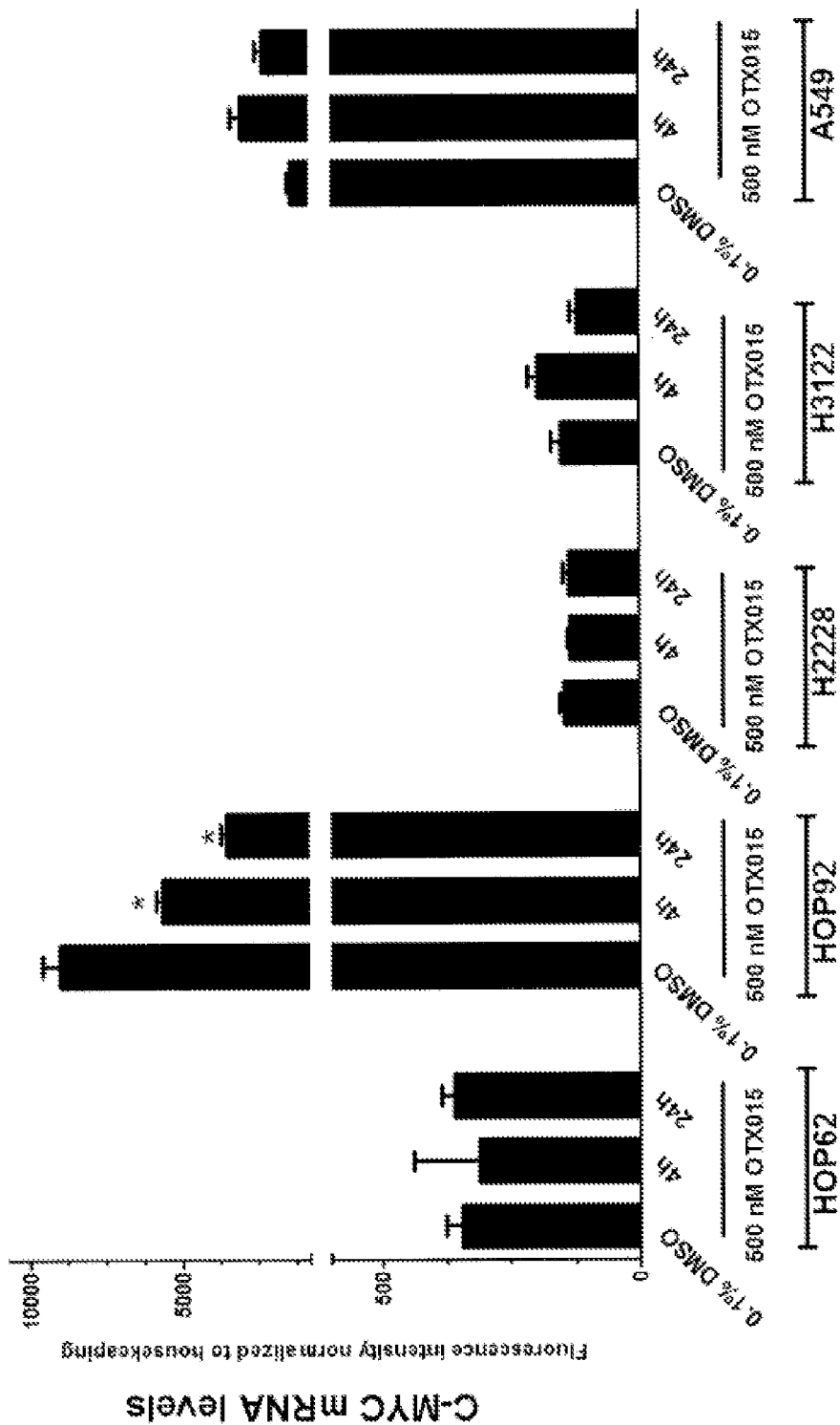
FIG. 16A illustrates C-MYC mRNA levels in HOP62, HOP92, H2228, H3122, and A549 cells after exposure to 500 nM of compound (1-1)
Figure 16B:
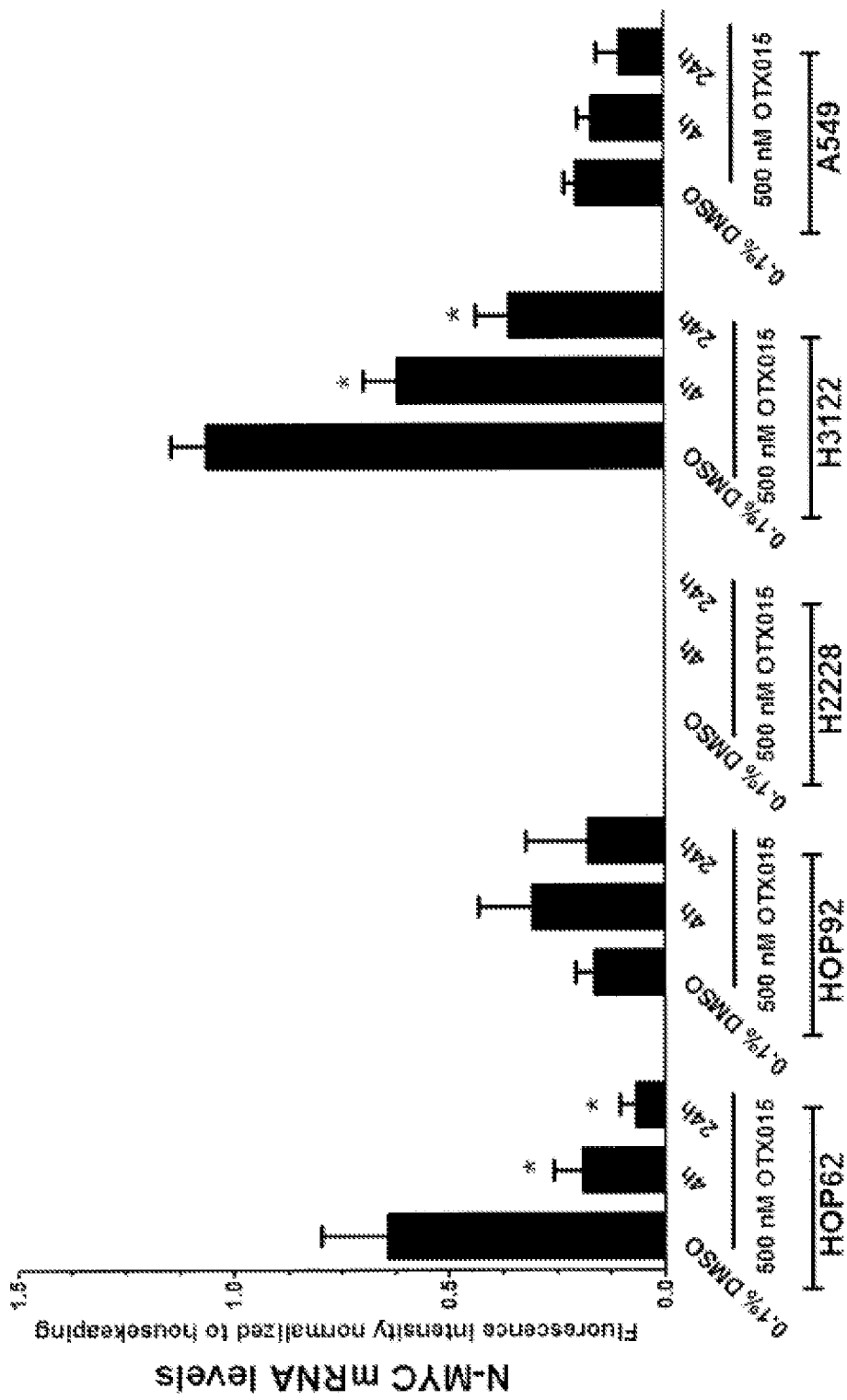
FIG. 16B illustrates N-MYC mRNA levels in HOP62, HOP92, H2228, H3122, and A549 cells after after exposure to 500 nM of compound (1-1)
Figure 16C:
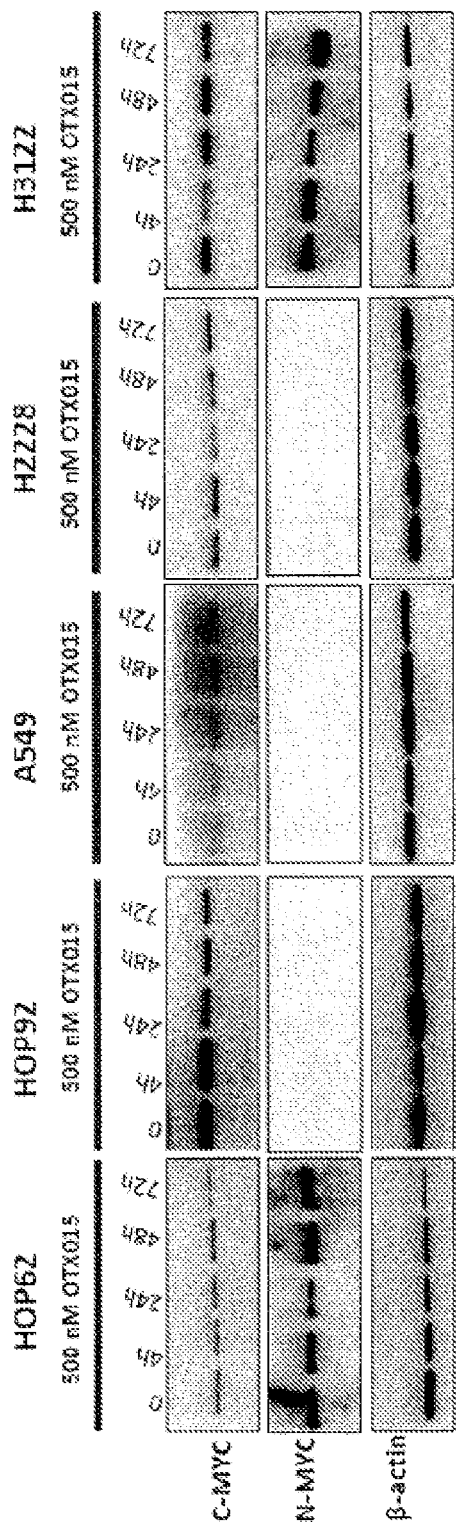
FIG. 16C illustrates regulation of C-MYC protein and N-MYC protein in HOP62, HOP92, H2228, H3122, and A549 cells after exposure to 500 nM of compound (1-1)
Figure 17:
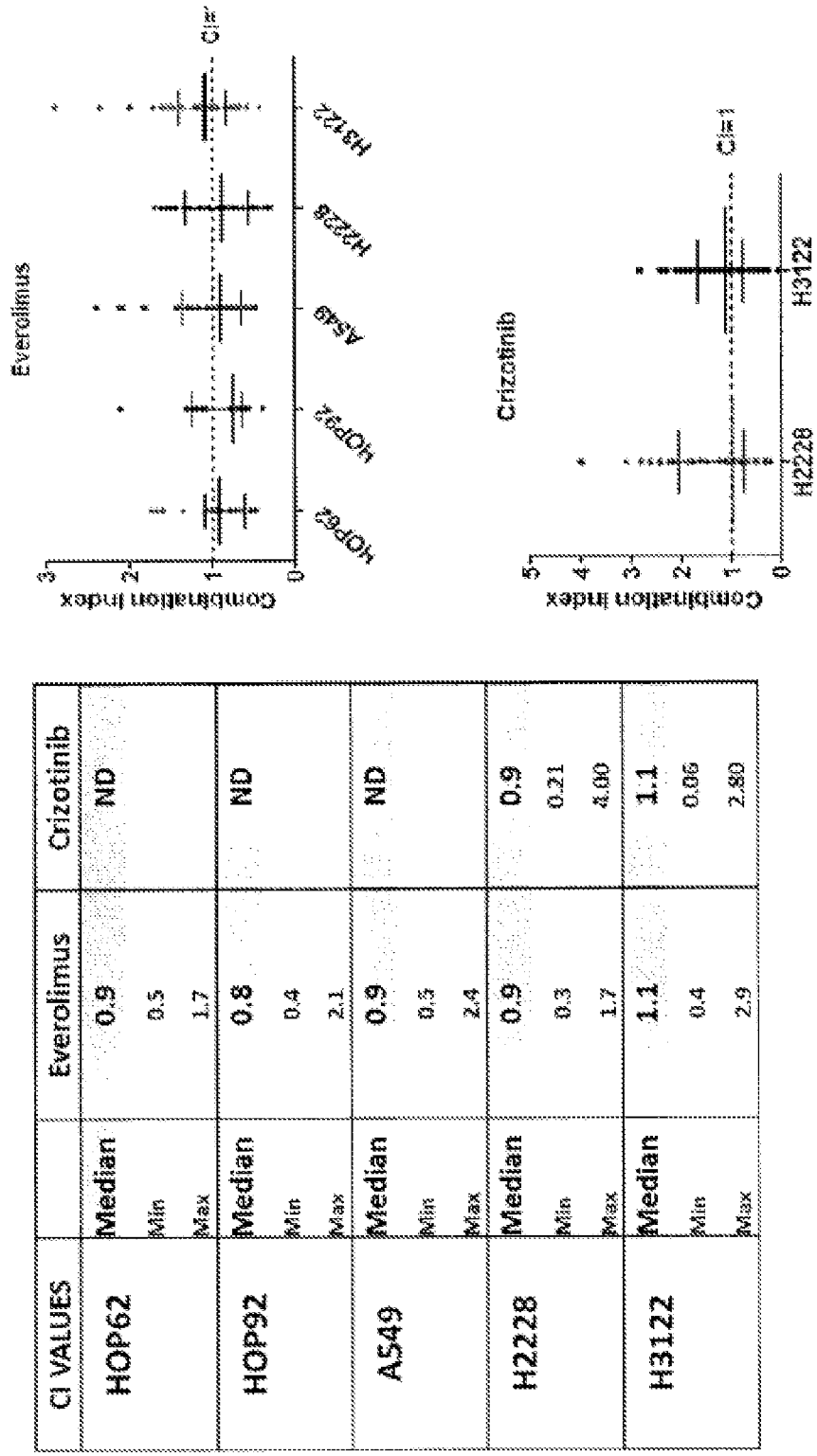
FIG. 17 illustrates the effects of compound (1-1) in concomitant combination with everolimus or critzotinib in NSCLC cell lines.
Figure 18A:
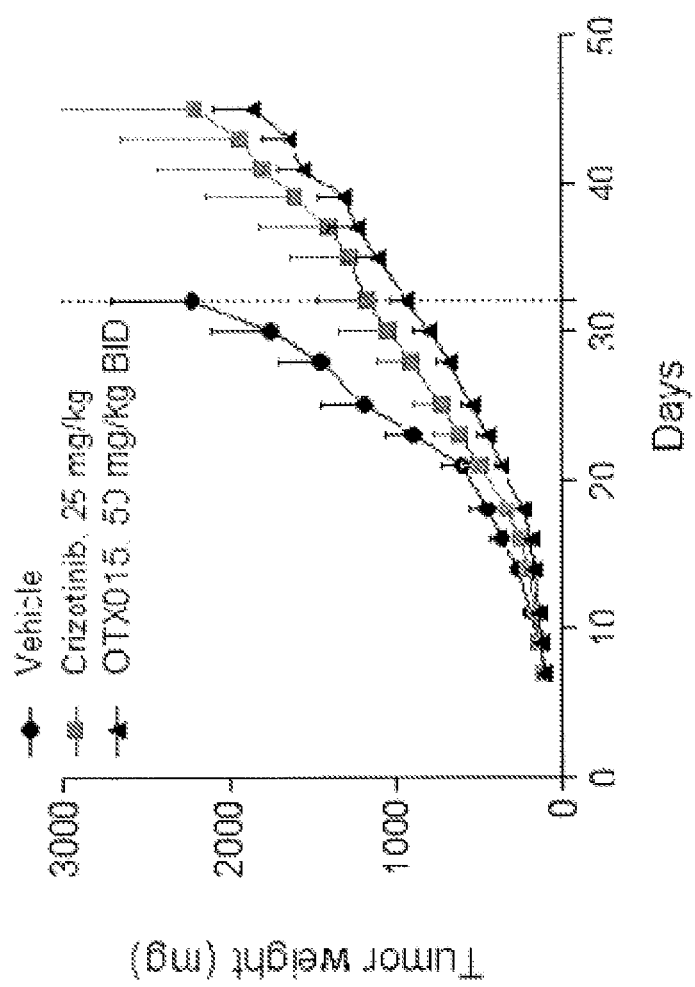
FIG. 18A illustrates that compound (1-1) slowed tumor progression in H3122 tumorbearing mice compared to vehicle control treated mice, crizotinib.
Figure 18B:
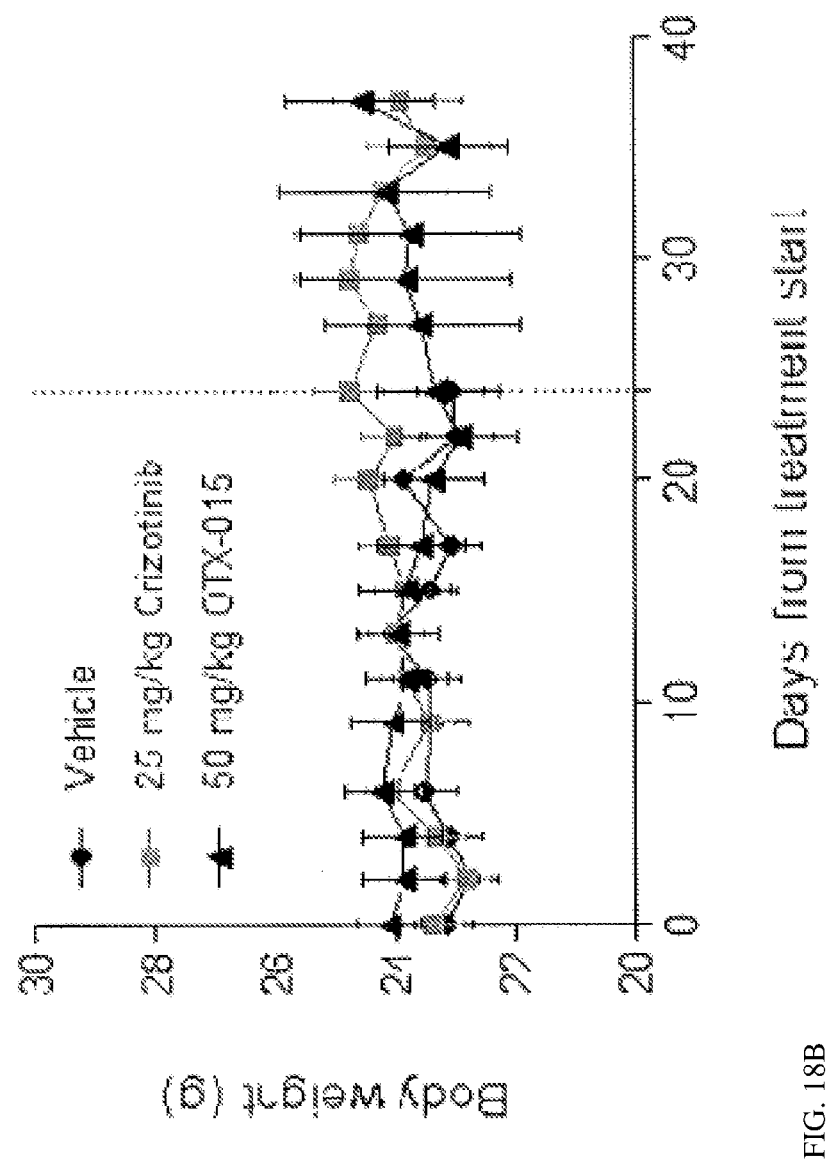
FIG. 18B illustrates that no weight loss was observed during the 3 weeks of compound (1-1) treatment.

Results. Compound (1-1) displays cytostatic effects in 4 out of 5 NSCLC cell lines, two of which harbor the fusion protein EML4-ALK+. In A549 cells, the concurrent mutations in KRAS and LKB1 genes abrogate compound (1-1) effects. In our cell line panel, GI50 values after 72 h exposure to compound (1-1) ranged between 0.1-0.7 µM, showing compound (1-1) is broadly active in NSCLC cells (FIG. 13). Compound (1-1) treatment also resulted in a reduction in the percentage of cells in S phase (FIG. 14). In NSCLC cell lines, characterization of the expression of BRD2/3/4, C-MYC, N-MYC, BCL-2 or P21 and cyclinD1 at the protein and mRNA levels did not show any correlations between basal levels of these proteins and compound (1-1) sensitivity (FIGS. 15A and 15B). That is, compound (1-1) sensitivity does not correlate with basal levels of BRDs, C-MYC, N-25 MYC, BCL2 or P21 in NSCLC cells. In compound (1-1)-sensistive cell lines, we observed a rapid downregulation of C-MYC mRNA and protein levels in HOP92 cells and of N-MYC mRNA levels in HOP62 and H3122 cells after 4 hours, which is maintained after 24 hours (FIGS. 16A-16C). Compound (1-1) combined with the ALK+-inhibitor crizotinib had additive effects (CI=0.9) after 48 h concomitant exposure in H2228 cells and additive/synergistic effects with everolimus in HOP62, HOP92, A549 and H2228 cell lines (FIG. 17). In H3122 tumor bearing-mice, compound (1-1) inhibited tumor growth to a similar extent as crizotinib, an EML4-ALK inhibitor (FIGS. 18A-B). Our data indicate that NSCLC cell lines, including those harboring the EML4-ALK fusion gene or KRAS mutation, are sensitive in vitro and in vivoto compound (1-1) BET inhibition.

Example 10

In Vitro Studies in SCLC Cell Lines

Compound (1-1) growth inhibition 50% (GI50) values were determined with the MTT assay after 72 h exposure in four established SCLC cell lines (H82, H69, DMS79, DMS114). Protein levels were analyzed by Western Blot using commercial antibodies and RT-PCR was performed with Fast SYBR Green Master Mix on a StepOnePlus Real-Time PCR System at baseline, then 4 and 24 h post-treatment. For cell cycle analysis, cells were stained with propidium iodide and analyzed for DNA content with a FACScan flow cytometer.

DMS114 cells showed dose-dependent sensitivity to compound (1-1) [GI50=120 (84-172) nM], while H82, H69, DMS79 cells were resistant [GI50>6 µM], although they overexpressed CMYC and/or NMYC proteins. While all four SCLC cell lines are KRAS wild-type and TP53 mutated, compound (1-1)-resistant SCLC cell lines harbor a homozygous mutation in RB1, while DMS144 cells express RB1 wild-type. All cell lines exhibited similar basal mRNA levels of BRD2/3/4, CMYC, NMYC, HEXIM, BCL-2 and p21. Following compound (1-1) treatment at 500 nM, CMYC and NMYC mRNA levels were unchanged, while mRNA levels of HEXIM and genes coding for histones (HIST1H2BK, HIST2H2BJ) were upregulated in all four cell lines. In DMS114 cells, compound (1-1) caused cell cycle arrest in G1 in a time-dependent manner, which, without being bound by theory, may be explained by an upregulation at the protein level of the cell cycle inhibitor p27.

Without being bound by a particular theory, the MYC family does not mediate compound (1-1) antitumor effects in SCLC cell lines. The presence of functional RB1 protein, controlling cell progression at G1, may explain the cytostatic effects of compound (1-1).

Example 11

In Vitro Studies in SCLC Cell Lines

Four established SCLC cell lines, NCI-H69, NCI-H82, DMS79, and DMS114 harboring different oncogenic mutations for KRAS, PI3KCA, TP53 and RB1, and having different expression levels of C-MYC and N-MYC, Table 7, were selected to evaluate compound (1-1).

Cell lines were exposed to increasing doses of compound (1-1) for 72 hours, and cell proliferation was evaluated with the MTT assay. GI50 and Emax values were calculated with the equation for sigmoidal dose response using Prism 5.00 for Windows. Results represent the mean±95% CI of at least 3 independent experiments performed in triplicate.

Protein levels were analyzed by Western Blot using commercial antibodies. For cell cycle analysis, cells were stained with PI and analyzed using a FACScan flow cytometer after 72 hours exposure. RT-qPCR was performed using Fast SYBR Green Master Mix on a StepOnePlus Real-Time PCR System. Cell cycle results represent the mean±SD of at least 3 independent experiments. RT-qPCR results are expressed as fluorescence intensity, normalized to two housekeeping genes, and represent the mean±SD of one experiment performed in duplicate or triplicate.

Compound (1-1) showed cytostatic effects in 1 out of the 4 SCLC cell lines. DMS114 cells showed dose-dependent sensitivity to compound (1-1) [GI50=120 (84-172) nM], while H82, H69, DMS79 cells were resistant [GI50>6 μM], FIG. 19. While all four SCLC cell lines are KRAS wild-type and TP53 mutated, compound (1-1)-resistant SCLC cell lines harbor a homozygous mutation in RB1, while DMS144 cells express RB1 wild-type.

Figure 20A:
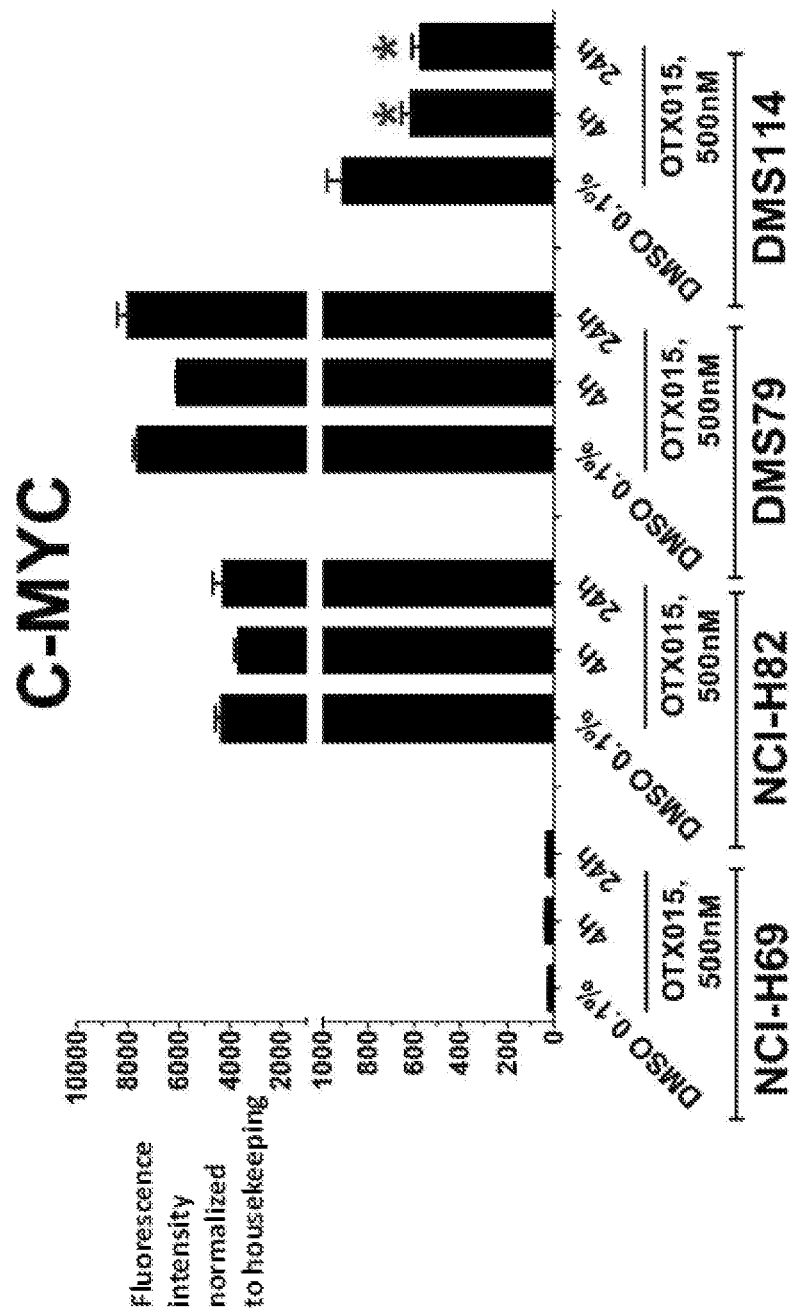
FIG. 20A illustrates the fluorescence intensity associated with C-MYC observed when NCI-H69, NCI-H82, DMS79 and DMS114 cell lines were treated with compound (1-1) for 4 and 24 hours.
Figure 20B:
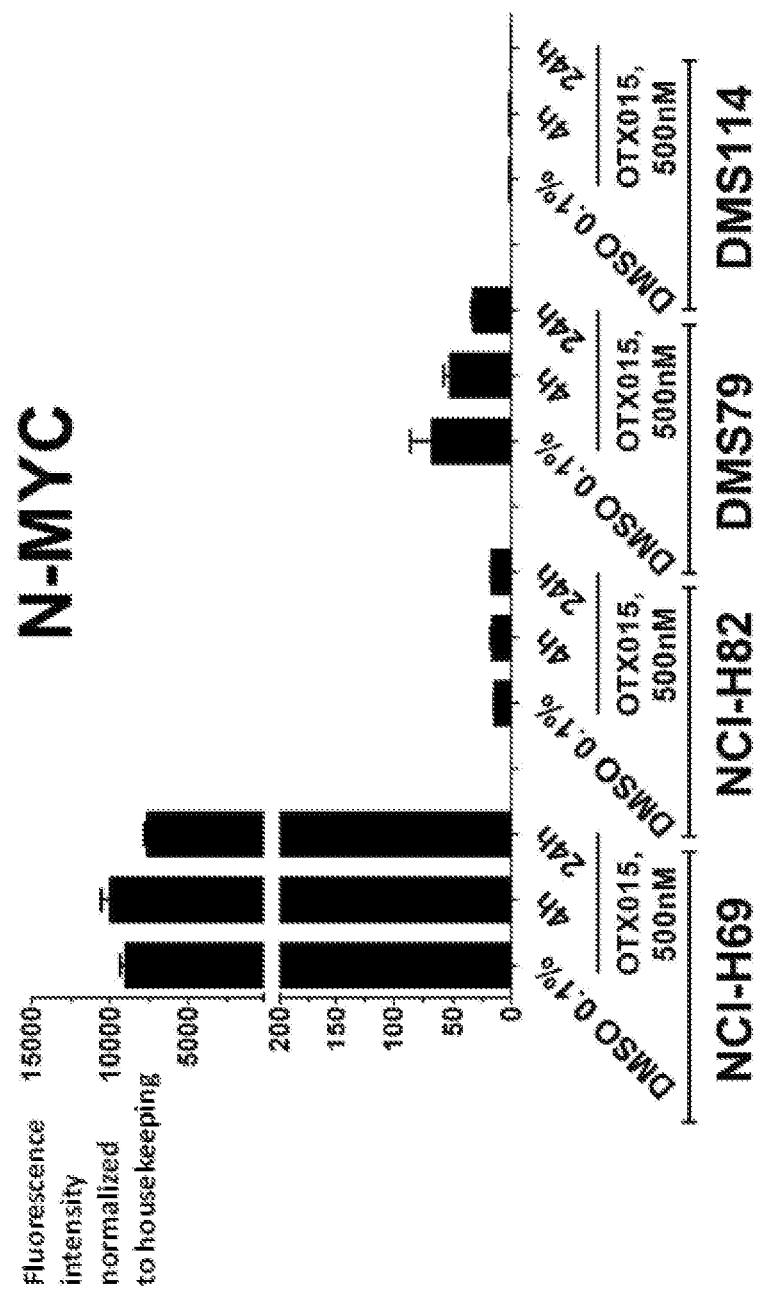
FIG. 20B illustrates the fluorescence intensity associated with N-MYC observed when NCI-H69, NCI-H82, DMS79 and DMS114 cell lines were treated with compound (1-1) for 4 and 24 hours.

Compound (1-1) induced a down regulation of C-MYC expression and an upregulation of HEXIM1 and genes encoding for histones. FIG. 20A illustrates the fluorescence intensity associated with C-MYC observed when NCI-H69, NCI-H82, DMS79 and DMS114 cell lines were treated with compound (1-1), at 500 nM, for 4 and 24 hours. In the compound (1-1) sensitive cell line DMS114, a rapid downregulation of C-MYC mRNA. FIG. 20B illustrates the fluorescence intensity associated with N-MYC observed when NCI-H69, NCI-H82, DMS79 and DMS114 cell lines were treated with compound (1-1), at 500 nM, for 4 and 24 hours.

Figure 20C:
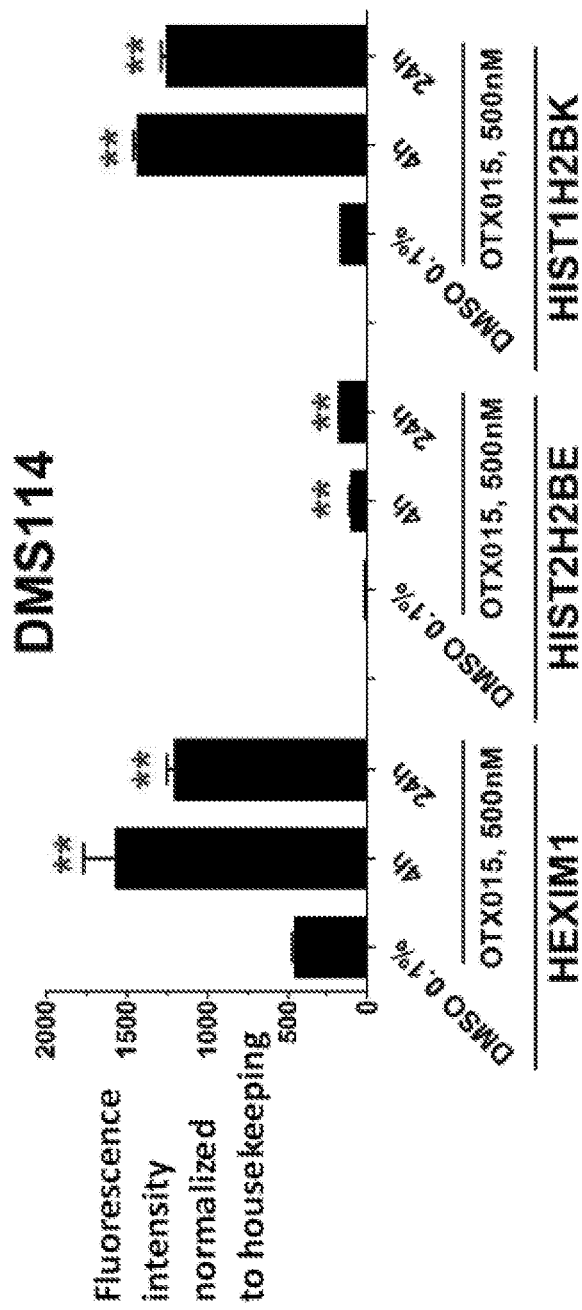
FIG. 20C illustrates the fluorescence intensity associated with HEXM1, HIST2H2BE AND HIST1H2BK observed with DMS114 cell line was treated with compound (1-1) for 4 and 24 hours.

FIG. 20C illustrates the fluorescence intensity associated with HEXM1, HIST2H2BE and HIST1H2BK observed with DMS114 cell line was treated with compound (1-1), at 500 nM, for 4 and 24 hours. An upregulation of mRNA levels of HEXIM1 and genes coding for histones (HIST2H2BE, HIST1H2BK) in the DMS114 cell line.

Figure 20D:
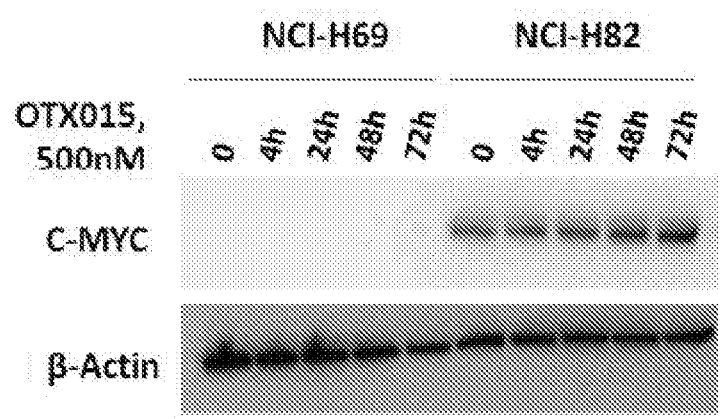
FIG. 20D illustrates the Western blot results for C-MYC and β-actin levels when treated with compound (1-1) for 0, 4, 24, 48 and 72 hours in NCI-H69, NCI-H82 cell lines.
Figure 20E:
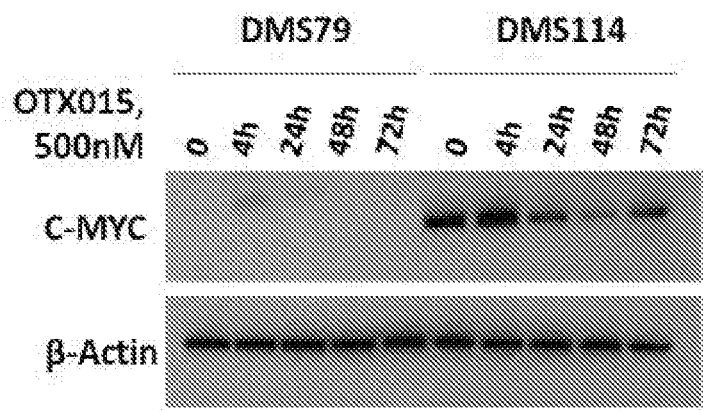
FIG. 20E illustrates the Western blot results for C-MYC and β-actin levels when treated with compound (1-1) for 0, 4, 24, 48 and 72 hours in DMS79 and DMS114 cell lines.

FIG. 20D illustrates the Western blot results for C-MYC and β-actin levels when treated with compound (1-1), at 500 nM, for 0, 4, 24, 48 and 72 hours in NCI-H69, NCI-H82 cell lines. FIG. 20E illustrates the Western blot results for C-MYC and β-actin levels when treated with compound (1-1), at 500 nM, for 0, 4, 24, 48 and 72 hours in DMS79 and DMS114 cell lines. C-MYC protein downregulation is observed in DMS114 cells after 24 hours exposure.

Figure 21A:
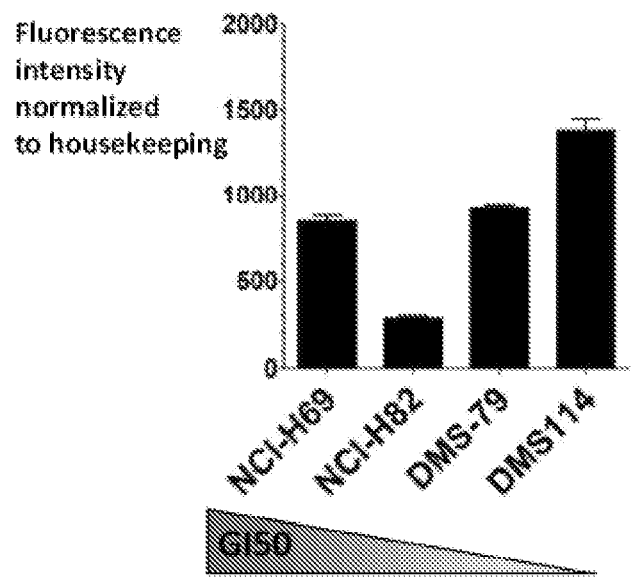
FIG. 21A illustrates the fluorescence intensity for BRD2 levels in NCI-H69, NCI-H82, DMS79 and DMS114 cell lines treated with compound (1-1) for 72 hours.
Figure 21B:
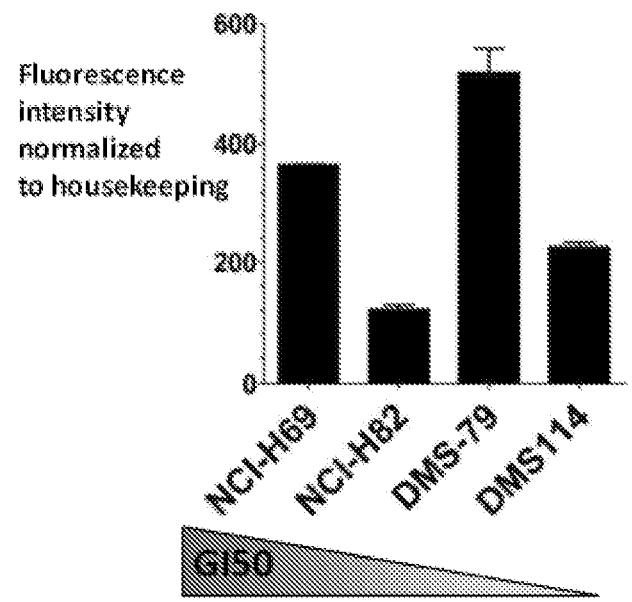
FIG. 21B illustrates the fluorescence intensity for BRD3 levels in NCI-H69, NCI-H82, DMS79 and DMS114 cell lines treated with compound (1-1) for 72 hours.
Figure 21C:
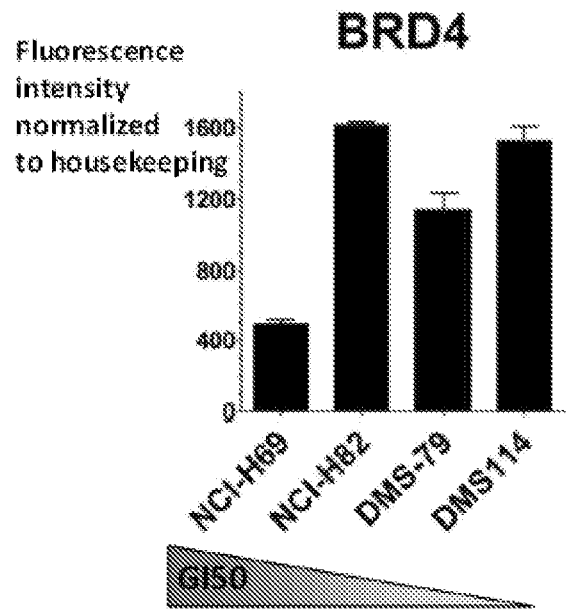
FIG. 21C illustrates the fluorescence intensity for BRD4 levels in NCI-H69, NCI-H82, DMS79 and DMS114 cell lines treated with compound (1-1) for 72 hours.
Figure 21D:
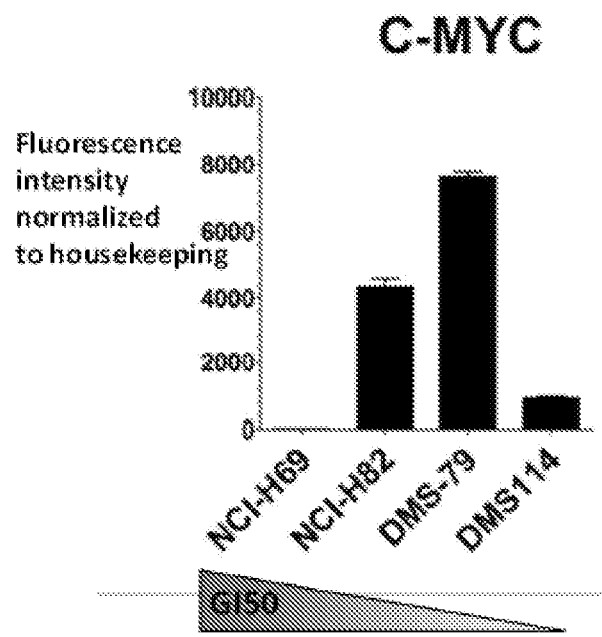
FIG. 21D illustrates the fluorescence intensity for C-MYC levels in NCI-H69, NCI-H82, DMS79 and DMS114 cell lines treated with compound (1-1) for 72 hours.
Figure 21E:
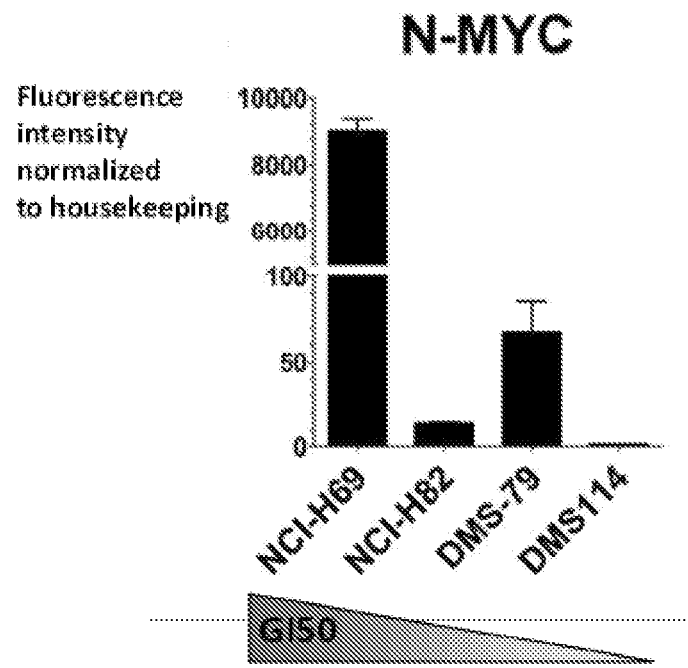
FIG. 21E illustrates the fluorescence intensity for N-MYC levels in NCI-H69, NCI-H82, DMS79 and DMS114 cell lines treated with compound (1-1) for 72 hours.
Figure 21F:
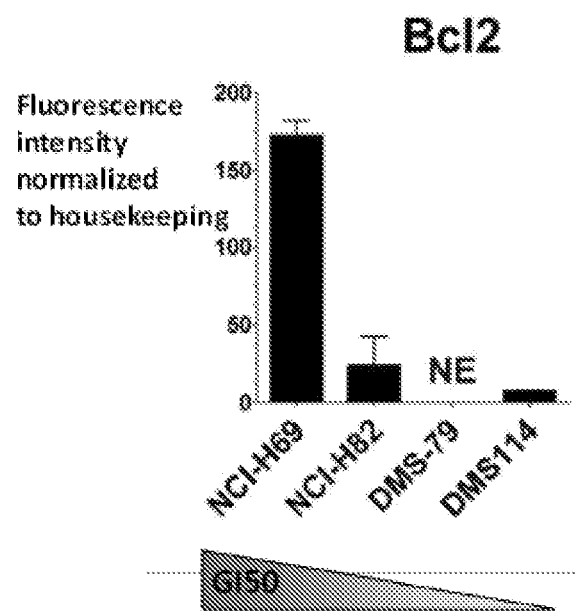
FIG. 21F illustrates the fluorescence intensity for Bcl2 levels in NCI-H69, NCI-H82, DMS79 and DMS114 cell lines treated with compound (1-1) for 72 hours.
Figure 21G:
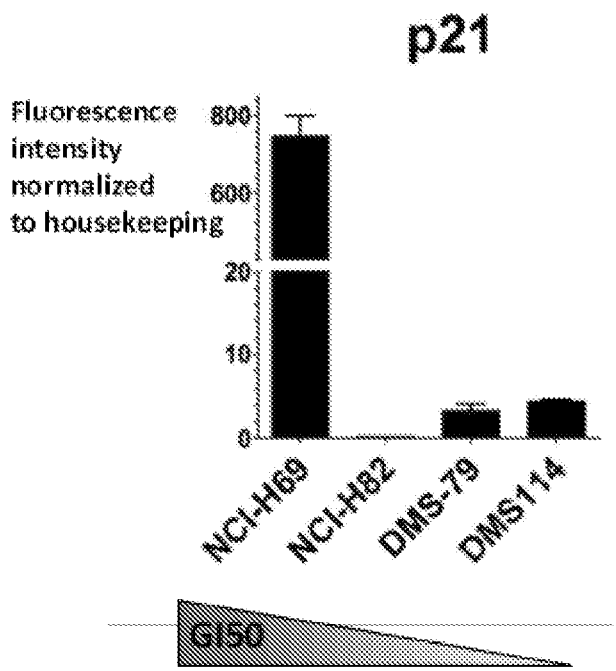
FIG. 21G illustrates the fluorescence intensity for p21 levels in NCI-H69, NCI-H82, DMS79 and DMS114 cell lines treated with compound (1-1) for 72 hours.
Figure 21H:
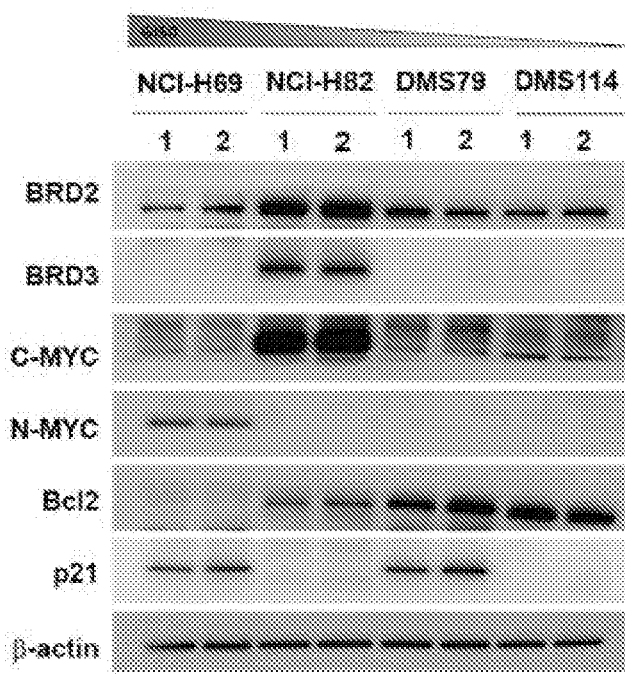
FIG. 21H illustrates the Western blot results for BRD2, BRD3, C-MYC, N-MYC, Bcl2, p21 and β-actin levels in NCI-H69, NCI-H82, DMS79 and DMS114 cell lines treated with compound (1-1) for 4 and 24 hours.

No correlations were seen in any of the four SCLC cell lines between compound (1-1), at 500 nM, sensitivity and basal mRNA levels of BRD2/3/4, C-MYC, N-MYC, HEXIM1, Bcl-2 and p21. FIGS. 21A-21G illustrate the fluorescence intensity for BRD2, BRD3, BRD4, C-MYC, N-MYC, Bcl2, and p21 levels, respectively, in NCI-H69, NCI-H82, DMS79 and DMS114 cell lines treated with compound (1-1) for 72 hours, ordered according to GI50 values. FIG. 21H illustrates the Western blot results for Basal protein expression of BRD2, BRD3, C-MYC, N-MYC, Bcl2, p21 and β-actin levels in NCI-H69, NCI-H82, DMS79 and DMS114 cell lines treated with compound (1-1) for 4 and 24 hours.

Figure 22A:
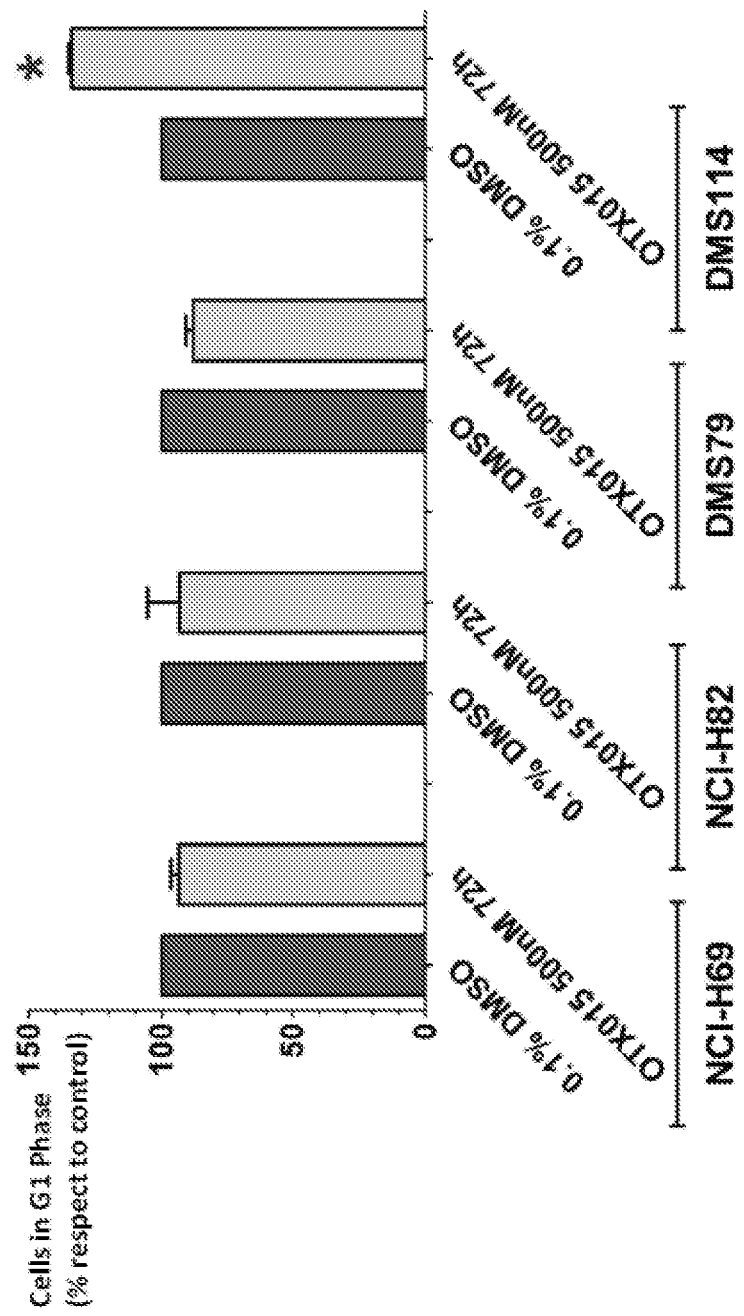
FIG. 22A illustrates the number of cells in the G1 phase for NCI-H69, NCI-H82, DMS79 and DMS114 cell lines treated with compound (1-1) for 72 hours and a control.
Figure 22B:
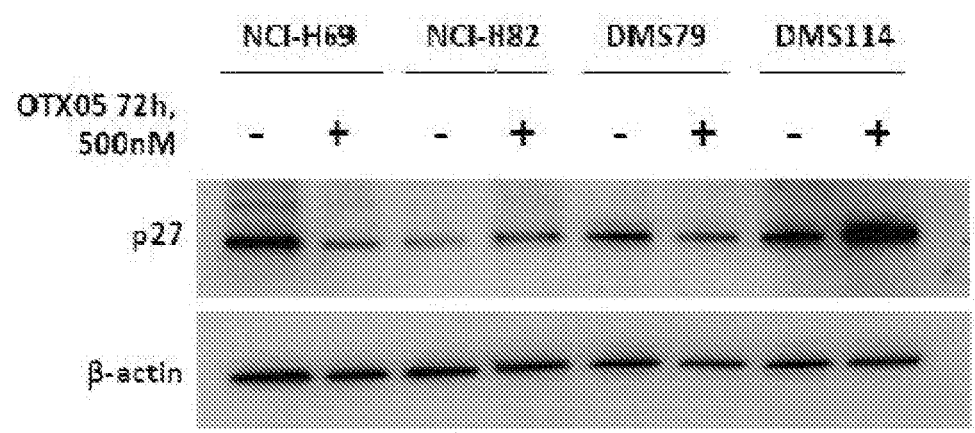
FIG. 22B illustrates the Western blot of p27 and β-actin levels for NCI-H69, NCI-H82, DMS79 and DMS114 cell lines treated with compound (1-1) for 72 hours and a control.

In DMS114 cells, compound (1-1) caused cell cycle arrest in G1 in a time-dependent manner, which, without being bound by theory, may be explained by an upregulation at the protein level of the cell cycle inhibitor p27. FIG. 22A illustrates the number of cells in the G1 phase for NCI-H69, NCI-H82, DMS79 and DMS114 cell lines treated with compound (1-1) for 72 hours and a control. Compound (1-1) significantly increased the G1 phase cell fraction in DMS114 cells after 72 h exposure. FIG. 22B illustrates the Western blot of p27 and β-actin levels for NCI-H69, NCI-H82, DMS79 and DMS114 cell lines treated with compound (1-1) for 72 hours and a control Without being bound by a particular theory, the MYC family does not mediate compound (1-1) antitumor effects in SCLC cell lines. The presence of functional RB1 protein, controlling cell progression at G1, may explain the cytostatic effects of compound (1-1). In the sensitive cell line, harboring wild-type RB1, compound (1-1) decreased C-MYC mRNA and protein expression, and induced G1 phase cell cycle arrest. These findings suggest that the MYC family plays a role in mediating OTX015 cytostatic effects in SCLC cells expressing non-mutated RB1 protein, which occurs in 10% of SCLC patients.

Example 12

Compound (1-1) in Preclinical Models of NSCLC and SCLC

Compound (1-1) (OncoEthix SA, Switzerland), growth inhibition 50% (GI50) values were determined with the MTT assay after 72 h exposure in 5 NSCLC cell lines (H2228, H3122, A549, HOP62, HOP92) and 4 SCLC cell lines (H82, H69, DMS79, DMS114). For cell cycle analysis, cells were stained with propidium iodide and analyzed with a FACScan flow cytometer. RNA was isolated after treatment with DMSO or OTX015 (500 nM) for 2, 4, 8 or 12 and 24 h and gene expression profiles (GEP) were obtained in all NSCLC and 2 SCLC (H82 and DMS114) cell lines with Illumina HumanHT-12 Expression BeadChips. Data mining was done with LIMMA, GSEA, Metacore.

Compound (1-1) displayed antiproliferative effects in 4 of the 5 NSCLC cell lines with GI50 values from 110 to 940 nM, whereas A549 cells (harboring mutations in KRAS and LKB1 genes) were resistant to compound (1-1), as described for JQ1. Among SLCL models, DMS114 cells showed dose-dependent sensitivity to compound (1-1) [GI50=120 nM], while H82, H69, and DMS79 cells were resistant [GI50>6 μM], despite overexpressing CMYC and/or NMYC. In sensitive-NSCLC models we observed an increase in cells in the S phase after compound (1-1) treatment, whereas an increase in the G1 phase was observed in the sensitive DMS114 cell line. To determine transcriptional changes following compound (1-1) treatment in SCLC cells, GEP analysis to identify transcripts differentially expressed in the sensitive or resistant cell line was performed, overall and at early (2-8 h) or late (12-24 h) time periods. This showed that EFR3B and genes related to RNA biogenesis correlated with reduced sensitivity to compound (1-1). On the other hand, genes related to histones and chromatin structure were the most differentially expressed after compound (1-1) exposure in both sensitive and resistant cell lines. In NSCLC models, EFR3B, IRF7 and FOS genes correlated with higher compound (1-1) sensitivity, with EFR3B and FOS gene upregulation together with IL7R and IL6-related gene downregulation observed after compound (1-1) treatment. Transcripts associated with compound (1-1) resistance were the transcription factor FOXD1 and genes related to RNA processing, inflammation and chromatin structure in NSCLC cells.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

The invention claimed is:

1. A method of treating non-small cell lung cancer or small cell lung cancer in a mammal comprising the step of administering to a patient a pharmaceutically acceptable amount of a compound which is (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide dihydrate wherein (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl) dihydrate is formed as a solid dispersion which comprises amorphous (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl) dihydrate and hydroxypropylmethylcellulose acetate succinate.

2. The method according to claim 1, wherein the (S)-2-[4-(4-chlorophenyl)-2,3,9-trimethyl-6H-thieno [3,2-f][1,2,4]triazolo-8 4,3-a][1,4]diazepin-6-yl]-N-(4-hydroxyphenyl) dihydrate to hydroxypropylmethylcellulose acetate succinate weight ratio is 1:3 to 1:1.

3. The method according to claim 1, wherein the solid dispersion exhibits an X-ray powder diffraction pattern substantially free of diffraction lines associated with crystalline (S)-2-[4-(4-chlorophenyl)-2,3,9-trimethyl-6H-thieno [3,2-f][1,2,4]triazolo-[4,3-a][1,4]diazepin-6-yl]-N-(4-hydroxyphenyl) dihydrate.

4. The method according to claim 1, wherein the solid dispersion exhibits a single glass transition temperature (Tg) inflection point ranging from about 130° C. to about 140°.

* * * * *